US008282967B2

(12) United States Patent
Schoenfisch et al.

(10) Patent No.: US 8,282,967 B2
(45) Date of Patent: Oct. 9, 2012

(54) NITRIC OXIDE-RELEASING PARTICLES FOR NITRIC OXIDE THERAPEUTICS AND BIOMEDICAL APPLICATIONS

(75) Inventors: Mark H. Schoenfisch, Chapel Hill, NC (US); Jae Ho Shin, Chapel Hill, NC (US); Nathan Stasko, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/168,597

(22) Filed: Jun. 24, 2011

(65) Prior Publication Data
US 2012/0021055 A1   Jan. 26, 2012

Related U.S. Application Data

(63) Continuation of application No. 13/157,036, filed on Jun. 9, 2011, which is a continuation of application No. 11/887,041, filed as application No. PCT/US2006/020781 on May 30, 2006, now abandoned.

(60) Provisional application No. 60/685,578, filed on May 27, 2005.

(51) Int. Cl.
*A61K 33/00* (2006.01)
*A61K 9/14* (2006.01)
(52) U.S. Cl. .................................... 424/718; 424/484
(58) Field of Classification Search .................. None
See application file for complete search history.

(56) References Cited

U.S. PATENT DOCUMENTS

| | | | |
|---|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 4,985,023 A | 1/1991 | Blank et al. |
| 4,990,338 A | 2/1991 | Blank et al. |
| 5,035,892 A | 7/1991 | Blank et al. |
| 5,045,322 A | 9/1991 | Blank et al. |
| 5,061,487 A | 10/1991 | Blank et al. |
| 5,079,004 A | 1/1992 | Blank et al. |
| 5,380,758 A | 1/1995 | Stamler et al. |
| 5,405,919 A | 4/1995 | Keefer et al. |
| 5,418,301 A | 5/1995 | Hult et al. |
| 5,428,070 A | 6/1995 | Cooke et al. |
| 5,504,117 A | 4/1996 | Gorfine |
| 5,519,020 A | 5/1996 | Smith et al. |
| 5,525,357 A | 6/1996 | Keefer et al. |
| 5,574,068 A | 11/1996 | Stamler et al. |
| 5,593,876 A | 1/1997 | Stamler et al. |
| 5,599,984 A | 2/1997 | Bianchi et al. |
| 5,629,322 A | 5/1997 | Guthikonda et al. |
| 5,632,981 A | 5/1997 | Saavedra et al. |
| 5,650,442 A | 7/1997 | Mitchell et al. |
| 5,650,447 A | 7/1997 | Keefer et al. |
| 5,665,077 A | 9/1997 | Rosen et al. |
| 5,676,963 A | 10/1997 | Keefer et al. |
| 5,691,423 A | 11/1997 | Smith et al. |
| 5,693,676 A | 12/1997 | Gorfine |
| 5,700,830 A | 12/1997 | Korthuis et al. |
| 5,718,892 A | 2/1998 | Keefer et al. |
| 5,726,156 A | 3/1998 | Girten et al. |
| 5,750,573 A | 5/1998 | Bianchi et al. |
| 5,753,684 A | 5/1998 | Bianchi et al. |
| 5,760,001 A | 6/1998 | Girten et al. |
| 5,770,645 A | 6/1998 | Stamler et al. |
| 5,786,332 A | 7/1998 | Girten et al. |
| 5,789,447 A | 8/1998 | Wink, Jr. et al. |
| 5,797,887 A | 8/1998 | Rosen et al. |
| 5,810,010 A | 9/1998 | Anbar |
| 5,814,666 A | 9/1998 | Green et al. |
| 5,814,667 A | 9/1998 | Mitchell et al. |
| 5,821,261 A | 10/1998 | Durette et al. |
| 5,837,736 A | 11/1998 | Mitchell et al. |
| 5,840,759 A | 11/1998 | Mitchell et al. |
| 5,849,794 A | 12/1998 | Bianchi et al. |
| 5,852,058 A | 12/1998 | Cooke et al. |
| 5,854,289 A | 12/1998 | Bianchi et al. |
| 5,859,062 A | 1/1999 | Bianchi et al. |
| 5,861,168 A | 1/1999 | Cooke et al. |
| 5,863,890 A | 1/1999 | Stamler et al. |
| 5,891,459 A | 4/1999 | Cooke et al. |
| 5,891,472 A | 4/1999 | Russell |

(Continued)

FOREIGN PATENT DOCUMENTS
EP    0805678 B1    10/2003
(Continued)

OTHER PUBLICATIONS

Barraud, N., et al., "Involvement of Nitric Oxide in Biofilm Dispersal of *Pseudomonas aeruginosa*," *Journal of Bacteriology*, 2006, vol. 188(21), pp. 7344-7353.

Coban, A., et al., "The Effect of Nitric Oxide Combined with Fluoroquinolones against *Salmonella enterica* Serovar Typhimurium in Vitro," *Mem Inst Oswaldo Cruz*, Rio de Janeiro, 2003, vol. 98(3), pp. 419-423.

Gupta, R., et al., "Bioactive materials for biomedical applications using sol-gel technology," *Biomed Mater.*, 2008, vol. 3, pp. 1-15.

McElhaney-Feser, G., et al., "Synergy of Nitric Oxide and Azoles against *Candida* Species In Vitro," *Antimicrobial Agents and Chemotherapy*, 1998, vol. 42(9), pp. 2342-2346.

Stasko, N., et al., "Dendrimers as a Scaffold for Nitric Oxide Release," *J. Am. Chem. Soc.*, 2006, vol. 128, pp. 8265-8271.

(Continued)

*Primary Examiner* — Robert A Wax
*Assistant Examiner* — H. Sarah Park
(74) *Attorney, Agent, or Firm* — Alston & Bird LLP

(57) ABSTRACT

The presently disclosed subject matter relates to nitric oxide-releasing particles for delivering nitric oxide, and their use in biomedical and pharmaceutical applications.

11 Claims, 40 Drawing Sheets

U.S. PATENT DOCUMENTS

| | | |
|---|---|---|
| 5,910,316 A | 6/1999 | Keefer et al. |
| 5,932,538 A | 8/1999 | Garvey et al. |
| 5,958,427 A | 9/1999 | Salzman et al. |
| 5,961,466 A | 10/1999 | Anbar |
| 5,962,520 A | 10/1999 | Smith et al. |
| 5,994,294 A | 11/1999 | Garvey et al. |
| 5,994,444 A | 11/1999 | Trescony et al. |
| 5,999,843 A | 12/1999 | Anbar |
| 6,008,255 A | 12/1999 | Bianchi et al. |
| 6,022,900 A | 2/2000 | Bianchi et al. |
| 6,035,225 A | 3/2000 | Anbar |
| 6,043,358 A | 3/2000 | Caldwell et al. |
| 6,045,827 A | 4/2000 | Russell |
| 6,070,928 A | 6/2000 | Campbell |
| 6,087,479 A | 7/2000 | Stamler et al. |
| 6,103,275 A | 8/2000 | Seitz et al. |
| 6,110,453 A | 8/2000 | Keefer et al. |
| 6,143,037 A | 11/2000 | Goldstein et al. |
| 6,147,068 A | 11/2000 | Smith et al. |
| 6,151,522 A | 11/2000 | Alfano et al. |
| 6,160,021 A | 12/2000 | Lerner et al. |
| 6,171,232 B1 | 1/2001 | Papandreou et al. |
| 6,174,539 B1 | 1/2001 | Stamler et al. |
| 6,180,082 B1 | 1/2001 | Woltering et al. |
| 6,180,676 B1 | 1/2001 | Bianchi et al. |
| 6,190,704 B1 | 2/2001 | Murrell |
| 6,200,558 B1 | 3/2001 | Saavedra et al. |
| 6,207,855 B1 | 3/2001 | Toone et al. |
| 6,218,016 B1 | 4/2001 | Tedeschi et al. |
| 6,232,336 B1 | 5/2001 | Hrabie et al. |
| 6,232,434 B1 | 5/2001 | Stamler et al. |
| 6,238,683 B1 | 5/2001 | Burnett et al. |
| 6,248,787 B1 | 6/2001 | Bianchi et al. |
| 6,255,277 B1 | 7/2001 | Stamler et al. |
| 6,261,594 B1 | 7/2001 | Smith et al. |
| 6,270,779 B1 | 8/2001 | Fitzhugh et al. |
| 6,287,601 B1 | 9/2001 | Russell |
| 6,290,981 B1 | 9/2001 | Keefer et al. |
| 6,291,424 B1 | 9/2001 | Stamler et al. |
| 6,294,517 B1 | 9/2001 | Garvey et al. |
| 6,299,980 B1 | 10/2001 | Shah et al. |
| 6,323,211 B1 | 11/2001 | Garvey et al. |
| 6,350,467 B1 | 2/2002 | Demopolos et al. |
| 6,352,709 B1 | 3/2002 | Stamler et al. |
| 6,358,536 B1 | 3/2002 | Thomas |
| 6,359,167 B2 | 3/2002 | Toone et al. |
| 6,359,182 B1 | 3/2002 | Stamler et al. |
| 6,369,071 B1 | 4/2002 | Haj-Yehia |
| 6,372,733 B1 | 4/2002 | Caldwell et al. |
| 6,377,321 B1 | 4/2002 | Khan et al. |
| 6,379,660 B1 | 4/2002 | Saavedra et al. |
| 6,379,691 B1 | 4/2002 | Tedeschi et al. |
| 6,391,895 B1 | 5/2002 | Towart et al. |
| 6,403,759 B2 | 6/2002 | Stamler et al. |
| 6,410,622 B1 | 6/2002 | Endres |
| 6,417,162 B1 | 7/2002 | Garvey et al. |
| 6,432,077 B1 | 8/2002 | Stenzler |
| 6,433,182 B1 | 8/2002 | Garvey et al. |
| 6,436,975 B1 | 8/2002 | Del Soldato |
| 6,441,254 B1 | 8/2002 | Dobert |
| 6,448,267 B1 | 9/2002 | Anggard et al. |
| 6,451,337 B1 | 9/2002 | Smith et al. |
| 6,455,542 B1 | 9/2002 | Anggard et al. |
| 6,469,065 B1 | 10/2002 | Garvey et al. |
| 6,471,968 B1 | 10/2002 | Baker, Jr. et al. |
| 6,471,978 B1 | 10/2002 | Stamler et al. |
| 6,472,390 B1 | 10/2002 | Stamler et al. |
| 6,488,951 B2 | 12/2002 | Toone et al. |
| 6,492,405 B2 | 12/2002 | Haj-Yehia |
| 6,511,991 B2 | 1/2003 | Hrabie et al. |
| 6,514,934 B1 | 2/2003 | Garvey et al. |
| 6,538,033 B2 | 3/2003 | Bing |
| 6,560,478 B1 | 5/2003 | Alfano et al. |
| 6,562,344 B1 | 5/2003 | Stamler et al. |
| 6,562,785 B1 | 5/2003 | Shapiro |
| 6,583,113 B2 | 6/2003 | Stamler et al. |
| 6,583,311 B2 | 6/2003 | Toone et al. |
| 6,605,447 B2 | 8/2003 | Weiss et al. |
| 6,610,660 B1 | 8/2003 | Saavedra et al. |
| 6,627,602 B2 | 9/2003 | Stamler et al. |
| 6,642,208 B2 | 11/2003 | Cooke et al. |
| 6,642,260 B2 | 11/2003 | Haj-Yehia |
| 6,645,518 B2 | 11/2003 | Tedeschi et al. |
| 6,646,006 B2 | 11/2003 | Cooke et al. |
| 6,656,217 B1 | 12/2003 | Herzog, Jr. et al. |
| 6,673,338 B1 | 1/2004 | Arnold et al. |
| 6,673,891 B2 | 1/2004 | Stamler et al. |
| 6,699,846 B2 | 3/2004 | Elliott et al. |
| 6,703,046 B2 | 3/2004 | Fitzhugh et al. |
| 6,706,274 B2 | 3/2004 | Herrmann et al. |
| 6,709,681 B2 | 3/2004 | Benjamin et al. |
| 6,723,703 B2 | 4/2004 | Gaston et al. |
| 6,737,447 B1 | 5/2004 | Smith et al. |
| 6,747,062 B2 | 6/2004 | Murrell |
| 6,750,254 B2 | 6/2004 | Hrabie et al. |
| 6,758,214 B2 | 7/2004 | Fine et al. |
| 6,759,430 B2 | 7/2004 | Anggard et al. |
| 6,780,849 B2 | 8/2004 | Herrmann et al. |
| 6,793,644 B2 | 9/2004 | Stenzler |
| 6,796,966 B2 | 9/2004 | Thomas |
| 6,841,166 B1 | 1/2005 | Zhang et al. |
| 6,855,366 B2 | 2/2005 | Smith et al. |
| 6,875,840 B2 | 4/2005 | Stamler et al. |
| 6,887,485 B2 | 5/2005 | Fitzhugh et al. |
| 6,887,994 B2 | 5/2005 | Stamler et al. |
| 6,894,073 B2 | 5/2005 | Lee et al. |
| 6,896,899 B2 | 5/2005 | Demopolos et al. |
| 6,897,218 B2 | 5/2005 | Casella et al. |
| 6,911,433 B2 | 6/2005 | Saavedra et al. |
| 6,911,478 B2 | 6/2005 | Hrabie et al. |
| 6,946,484 B2 | 9/2005 | Adams et al. |
| 6,949,530 B2 | 9/2005 | Hrabie et al. |
| 6,951,902 B2 | 10/2005 | McDonald et al. |
| 6,964,984 B2 | 11/2005 | Stamler et al. |
| 6,974,801 B2 | 12/2005 | Honda et al. |
| 7,012,098 B2 | 3/2006 | Manning et al. |
| 7,015,347 B2 | 3/2006 | Toone et al. |
| 7,025,869 B2 | 4/2006 | Fine et al. |
| 7,030,238 B2 | 4/2006 | Stamler et al. |
| 7,033,999 B2 | 4/2006 | Stamler et al. |
| 7,040,313 B2 | 5/2006 | Fine et al. |
| 7,048,951 B1 | 5/2006 | Seitz et al. |
| 7,049,308 B2 | 5/2006 | Stamler et al. |
| 7,052,711 B2 | 5/2006 | West et al. |
| 7,070,798 B1 | 7/2006 | Michal et al. |
| 7,081,524 B2 | 7/2006 | Saavedra et al. |
| 7,087,588 B2 | 8/2006 | Del Soldato |
| 7,087,709 B2 | 8/2006 | Stamler et al. |
| 7,122,018 B2 | 10/2006 | Stenzler et al. |
| 7,122,027 B2 | 10/2006 | Trescony et al. |
| 7,122,529 B2 | 10/2006 | Ruane et al. |
| 7,128,904 B2 | 10/2006 | Batchelor et al. |
| 7,135,189 B2 | 11/2006 | Knapp |
| 7,135,498 B1 | 11/2006 | Chopp et al. |
| 7,157,500 B2 | 1/2007 | Stamler et al. |
| 7,169,809 B2 | 1/2007 | Berthelette et al. |
| 7,176,237 B2 | 2/2007 | Honda et al. |
| 7,179,475 B1 | 2/2007 | Burnett et al. |
| 7,189,761 B2 | 3/2007 | Gorfine |
| 7,199,154 B2 | 4/2007 | Berthelette et al. |
| 7,204,980 B2 | 4/2007 | Clark |
| 7,226,586 B2 | 6/2007 | Fitzhugh et al. |
| 7,259,250 B2 | 8/2007 | Stamler et al. |
| 7,279,176 B1 | 10/2007 | West et al. |
| 7,282,519 B2 | 10/2007 | Garvey et al. |
| 7,314,857 B2 | 1/2008 | Madhyastha |
| 7,335,383 B2 | 2/2008 | Meyerhoff et al. |
| 7,345,053 B2 | 3/2008 | Garvey |
| 7,348,319 B2 | 3/2008 | Hrabie et al. |
| 7,364,585 B2 | 4/2008 | Weber |
| 7,396,829 B2 | 7/2008 | Garvey et al. |
| 7,417,109 B2 | 8/2008 | Stamler et al. |
| 7,425,218 B2 | 9/2008 | Keefer et al. |
| 7,432,301 B2 | 10/2008 | Gaston et al. |
| 7,452,916 B2 | 11/2008 | Cooke |
| 7,468,435 B2 | 12/2008 | Waterhouse et al. |
| 7,485,324 B2 | 2/2009 | Miller et al. |

| Patent Number | Date | Inventor |
|---|---|---|
| 7,520,866 B2 | 4/2009 | Stenzler et al. |
| 7,531,164 B2 | 5/2009 | Daaka et al. |
| 7,569,559 B2 | 8/2009 | Arnold et al. |
| 7,582,623 B2 | 9/2009 | Mascharak |
| 7,595,313 B2 | 9/2009 | Garvey et al. |
| 7,622,501 B2 | 11/2009 | Dufresne et al. |
| 7,622,502 B2 | 11/2009 | Berthelette et al. |
| 7,645,748 B2 | 1/2010 | Orchansky et al. |
| 7,645,749 B2 | 1/2010 | Orchansky et al. |
| 7,651,697 B2 | 1/2010 | West et al. |
| 7,655,423 B2 | 2/2010 | Chopp et al. |
| 7,678,391 B2 | 3/2010 | Graham et al. |
| 7,678,830 B2 | 3/2010 | Honda et al. |
| 7,696,247 B2 | 4/2010 | Herrmann et al. |
| 7,745,656 B2 | 6/2010 | Toone et al. |
| 7,763,283 B2 | 7/2010 | Batchelor et al. |
| 7,785,616 B2 | 8/2010 | Stamler et al. |
| 7,795,286 B2 | 9/2010 | Lucet-Levannier |
| 7,799,335 B2 | 9/2010 | Herrmann et al. |
| 7,807,716 B2 | 10/2010 | Farber |
| 7,811,600 B2 | 10/2010 | Cheng et al. |
| 7,820,284 B2 | 10/2010 | Terry |
| 7,829,553 B2 | 11/2010 | Arnold et al. |
| 7,838,023 B2 | 11/2010 | Garvey et al. |
| 7,846,400 B2 | 12/2010 | Hyde et al. |
| 7,862,598 B2 | 1/2011 | Hyde et al. |
| 7,892,198 B2 | 2/2011 | Stenzler |
| 7,897,399 B2 | 3/2011 | Hyde et al. |
| 7,928,079 B2 | 4/2011 | Hrabie et al. |
| 7,928,096 B2 | 4/2011 | Waterhouse et al. |
| 7,947,299 B2 | 5/2011 | Knapp |
| 7,972,137 B2 | 7/2011 | Rosen |
| 2001/0012851 A1 | 8/2001 | Lundy et al. |
| 2001/0025057 A1 | 9/2001 | Gorfine |
| 2001/0038832 A1 | 11/2001 | Bonavida et al. |
| 2001/0053772 A1 | 12/2001 | Bonavida et al. |
| 2002/0028851 A1 | 3/2002 | Bianchi et al. |
| 2002/0049157 A1 | 4/2002 | Wu et al. |
| 2002/0061879 A1 | 5/2002 | Garvey et al. |
| 2002/0068365 A1 | 6/2002 | Kuhrts |
| 2002/0077502 A1 | 6/2002 | Dobert et al. |
| 2002/0090401 A1 | 7/2002 | Tucker et al. |
| 2002/0115586 A1 | 8/2002 | Enikolopov |
| 2002/0132234 A1 | 9/2002 | Moskowitz |
| 2002/0136763 A1 | 9/2002 | Demopoulos et al. |
| 2002/0138051 A1 | 9/2002 | Hole et al. |
| 2002/0143007 A1 | 10/2002 | Garvey et al. |
| 2002/0143062 A1 | 10/2002 | Lopez-Berestein et al. |
| 2002/0155174 A1 | 10/2002 | Benjamin et al. |
| 2002/0161042 A1 | 10/2002 | Gorfine |
| 2003/0009127 A1 | 1/2003 | Trescony et al. |
| 2003/0026849 A1 | 2/2003 | Thomas |
| 2003/0027844 A1 | 2/2003 | Soldato |
| 2003/0032681 A1 | 2/2003 | Coronado et al. |
| 2003/0039697 A1 | 2/2003 | Zhao et al. |
| 2003/0050305 A1 | 3/2003 | Tejada |
| 2003/0072783 A1 | 4/2003 | Stamler et al. |
| 2003/0093143 A1 | 5/2003 | Zhao et al. |
| 2003/0134779 A1 | 7/2003 | Diarra et al. |
| 2003/0170674 A1 | 9/2003 | Moskowitz |
| 2003/0203915 A1 | 10/2003 | Fang et al. |
| 2004/0009238 A1 | 1/2004 | Miller et al. |
| 2004/0013747 A1 | 1/2004 | Tucker et al. |
| 2004/0033480 A1 | 2/2004 | Wong |
| 2004/0037836 A1 | 2/2004 | Stamler et al. |
| 2004/0037897 A1 | 2/2004 | Benjamin et al. |
| 2004/0043068 A1 | 3/2004 | Tedeschi et al. |
| 2004/0076582 A1 | 4/2004 | Dimatteo et al. |
| 2004/0082659 A1 | 4/2004 | Cooke et al. |
| 2004/0105898 A1 | 6/2004 | Benjamin et al. |
| 2004/0110691 A1 | 6/2004 | Stamler |
| 2004/0131703 A1 | 7/2004 | Bach et al. |
| 2004/0143010 A1 | 7/2004 | Esteve-Soler et al. |
| 2004/0147598 A1 | 7/2004 | Haj-Yehia |
| 2004/0157936 A1 | 8/2004 | Burnett et al. |
| 2004/0158048 A1 | 8/2004 | Ruane et al. |
| 2004/0228889 A1 | 11/2004 | Cals-Grierson |
| 2004/0254419 A1 | 12/2004 | Wang et al. |
| 2005/0022046 A1 | 1/2005 | Cheng et al. |
| 2005/0036949 A1 | 2/2005 | Tucker et al. |
| 2005/0037050 A1 | 2/2005 | Weber |
| 2005/0037093 A1 | 2/2005 | Benjamin |
| 2005/0054714 A1 | 3/2005 | Munoz et al. |
| 2005/0065161 A1 | 3/2005 | Garvey et al. |
| 2005/0069595 A1 | 3/2005 | Chen et al. |
| 2005/0074506 A1 | 4/2005 | Natan et al. |
| 2005/0080021 A1 | 4/2005 | Tucker et al. |
| 2005/0080024 A1 | 4/2005 | Tucker et al. |
| 2005/0131064 A1 | 6/2005 | Gaston et al. |
| 2005/0142217 A1 | 6/2005 | Adams et al. |
| 2005/0142218 A1 | 6/2005 | Tucker et al. |
| 2005/0152891 A1 | 7/2005 | Toone et al. |
| 2005/0165452 A1 | 7/2005 | Sigg et al. |
| 2005/0171066 A1 | 8/2005 | Shami |
| 2005/0171199 A1 | 8/2005 | Murrell |
| 2005/0187222 A1 | 8/2005 | Garvey et al. |
| 2005/0220838 A1 | 10/2005 | Zhao et al. |
| 2005/0249818 A1 | 11/2005 | Sawan et al. |
| 2005/0265958 A1 | 12/2005 | West et al. |
| 2005/0281867 A1 | 12/2005 | Kahn et al. |
| 2006/0008529 A1 | 1/2006 | Meyerhoff et al. |
| 2006/0009431 A1 | 1/2006 | Earl et al. |
| 2006/0034169 A1 | 2/2006 | Hong |
| 2006/0035854 A1 | 2/2006 | Goldstein et al. |
| 2006/0039950 A1 | 2/2006 | Zhou et al. |
| 2006/0058363 A1 | 3/2006 | Wang et al. |
| 2006/0067909 A1 | 3/2006 | West et al. |
| 2006/0095120 A1 | 5/2006 | Hermann |
| 2006/0100159 A1 | 5/2006 | Stamler et al. |
| 2006/0142183 A1 | 6/2006 | Diarra et al. |
| 2006/0147553 A1 | 7/2006 | Miller et al. |
| 2006/0147904 A1 | 7/2006 | Wong |
| 2006/0159726 A1 | 7/2006 | Shell |
| 2006/0172018 A1 | 8/2006 | Fine et al. |
| 2006/0198831 A1 | 9/2006 | Stamler et al. |
| 2006/0211601 A1 | 9/2006 | Stamler et al. |
| 2006/0269620 A1 | 11/2006 | Morris et al. |
| 2006/0286158 A1 | 12/2006 | Calvert Murrell et al. |
| 2006/0286159 A1 | 12/2006 | Calvert Murrell et al. |
| 2007/0003538 A1 | 1/2007 | Madhyastha |
| 2007/0014686 A1 | 1/2007 | Arnold et al. |
| 2007/0014733 A1 | 1/2007 | O'Donnell et al. |
| 2007/0014828 A1 | 1/2007 | Fitzhugh et al. |
| 2007/0037821 A1 | 2/2007 | Garvey et al. |
| 2007/0048344 A1 | 3/2007 | Yahiaoui et al. |
| 2007/0053952 A1 | 3/2007 | Chen et al. |
| 2007/0053955 A1 | 3/2007 | Larson et al. |
| 2007/0053966 A1 | 3/2007 | Ang et al. |
| 2007/0059351 A1 | 3/2007 | Murrell et al. |
| 2007/0086954 A1 | 4/2007 | Miller |
| 2007/0087025 A1 | 4/2007 | Fitzhugh et al. |
| 2007/0088345 A1 | 4/2007 | Larson et al. |
| 2007/0089739 A1 | 4/2007 | Fine et al. |
| 2007/0116785 A1 | 5/2007 | Miller |
| 2007/0129690 A1 | 6/2007 | Rosenblatt et al. |
| 2007/0148136 A1 | 6/2007 | Whitlock |
| 2007/0154570 A1 | 7/2007 | Miller et al. |
| 2007/0166227 A1 | 7/2007 | Liu et al. |
| 2007/0172469 A1 | 7/2007 | Clark |
| 2007/0191377 A1 | 8/2007 | Worcel |
| 2007/0196327 A1 | 8/2007 | Kalivretenos et al. |
| 2007/0197543 A1 | 8/2007 | Esteve-Soler et al. |
| 2007/0202155 A1 | 8/2007 | Ang et al. |
| 2007/0203242 A1 | 8/2007 | Calton |
| 2007/0207179 A1 | 9/2007 | Andersen et al. |
| 2007/0219208 A1 | 9/2007 | Kalyanaraman et al. |
| 2007/0225250 A1 | 9/2007 | Brown |
| 2007/0239107 A1 | 10/2007 | Lundberg et al. |
| 2007/0243262 A1 | 10/2007 | Hurley et al. |
| 2007/0248676 A1 | 10/2007 | Stamler et al. |
| 2007/0264225 A1 | 11/2007 | Cheng et al. |
| 2007/0270348 A1 | 11/2007 | Kahn et al. |
| 2007/0275100 A1 | 11/2007 | Miller |
| 2007/0292471 A1 | 12/2007 | Hrabie et al. |
| 2008/0025972 A1 | 1/2008 | Daaka et al. |
| 2008/0039521 A1 | 2/2008 | Yasuda et al. |
| 2008/0045909 A1 | 2/2008 | Fossel |
| 2008/0069848 A1 | 3/2008 | Peters |

| | | |
|---|---|---|
| 2008/0069863 A1 | 3/2008 | Peters |
| 2008/0069905 A1 | 3/2008 | Peters |
| 2008/0071206 A1 | 3/2008 | Peters |
| 2008/0089956 A1 | 4/2008 | Da et al. |
| 2008/0139450 A1 | 6/2008 | Madhyastha et al. |
| 2008/0145449 A1 | 6/2008 | Stamler |
| 2008/0171021 A1 | 7/2008 | Bach et al. |
| 2008/0171351 A1 | 7/2008 | Smith |
| 2008/0175881 A1 | 7/2008 | Ippoliti et al. |
| 2008/0182797 A1 | 7/2008 | Nudler et al. |
| 2008/0193385 A1 | 8/2008 | Maibach |
| 2008/0193566 A1 | 8/2008 | Miller et al. |
| 2008/0207491 A1 | 8/2008 | Diarra et al. |
| 2008/0207713 A1 | 8/2008 | Wang et al. |
| 2008/0214646 A1 | 9/2008 | Knaus et al. |
| 2008/0220048 A1 | 9/2008 | Chen et al. |
| 2008/0226686 A1 | 9/2008 | Meyerhoff et al. |
| 2008/0226751 A1 | 9/2008 | Tucker et al. |
| 2008/0241208 A1 | 10/2008 | Shanley et al. |
| 2008/0255101 A1 | 10/2008 | Garvey et al. |
| 2008/0275093 A1 | 11/2008 | Garvey et al. |
| 2008/0280984 A1 | 11/2008 | Fossel |
| 2008/0286321 A1 | 11/2008 | Reneker et al. |
| 2008/0287861 A1 | 11/2008 | Stenzler et al. |
| 2008/0311163 A1 | 12/2008 | Peters |
| 2008/0317626 A1 | 12/2008 | Arnold et al. |
| 2008/0317679 A1 | 12/2008 | Tamarkin et al. |
| 2009/0004298 A1 | 1/2009 | Gaston et al. |
| 2009/0010989 A1 | 1/2009 | Peters |
| 2009/0018091 A1 | 1/2009 | Ellis et al. |
| 2009/0028966 A1 | 1/2009 | Chen et al. |
| 2009/0036491 A1 | 2/2009 | Tucker et al. |
| 2009/0042819 A1 | 2/2009 | Ellis et al. |
| 2009/0048219 A1 | 2/2009 | Garvey |
| 2009/0069449 A1 | 3/2009 | Smith et al. |
| 2009/0081279 A1 | 3/2009 | Jezek et al. |
| 2009/0088411 A1 | 4/2009 | Renzi et al. |
| 2009/0093510 A1 | 4/2009 | Clementi et al. |
| 2009/0098187 A1 | 4/2009 | Peters et al. |
| 2009/0107512 A1 | 4/2009 | Hyde et al. |
| 2009/0108777 A1 | 4/2009 | Hyde et al. |
| 2009/0110612 A1 | 4/2009 | Hyde et al. |
| 2009/0110712 A1 | 4/2009 | Hyde et al. |
| 2009/0110933 A1 | 4/2009 | Hyde et al. |
| 2009/0110958 A1 | 4/2009 | Hyde et al. |
| 2009/0112055 A1 | 4/2009 | Hyde et al. |
| 2009/0112193 A1 | 4/2009 | Hyde et al. |
| 2009/0112197 A1 | 4/2009 | Hyde et al. |
| 2009/0118819 A1 | 5/2009 | Merz et al. |
| 2009/0123528 A1 | 5/2009 | Fossel |
| 2009/0131342 A1 | 5/2009 | Ellis |
| 2009/0131883 A1 | 5/2009 | Av-Gay et al. |
| 2009/0136410 A1 | 5/2009 | Smith |
| 2009/0137683 A1 | 5/2009 | Yasuda et al. |
| 2009/0143417 A1 | 6/2009 | Smith et al. |
| 2009/0148482 A1 | 6/2009 | Peters |
| 2009/0186859 A1 | 7/2009 | Velázquez et al. |
| 2009/0191284 A1 | 7/2009 | Conoci et al. |
| 2009/0196930 A1 | 8/2009 | Surber et al. |
| 2009/0197964 A1 | 8/2009 | Summar et al. |
| 2009/0203653 A1 | 8/2009 | Garvey |
| 2009/0214618 A1 | 8/2009 | Schoenfisch et al. |
| 2009/0214624 A1 | 8/2009 | Smith et al. |
| 2009/0214674 A1 | 8/2009 | Barraud et al. |
| 2009/0215838 A1 | 8/2009 | Garvey et al. |
| 2009/0221536 A1 | 9/2009 | Fossel |
| 2009/0222088 A1 | 9/2009 | Chen et al. |
| 2009/0226504 A1 | 9/2009 | Peters |
| 2009/0232863 A1 | 9/2009 | Cheng et al. |
| 2009/0232868 A1 | 9/2009 | Chen et al. |
| 2009/0255536 A1 | 10/2009 | Av-Gay et al. |
| 2009/0263416 A1 | 10/2009 | Dawson et al. |
| 2009/0264398 A1 | 10/2009 | Bauer |
| 2009/0270509 A1 | 10/2009 | Arnold et al. |
| 2009/0287072 A1 | 11/2009 | Meyerhoff et al. |
| 2009/0297634 A1 | 12/2009 | Friedman et al. |
| 2009/0304815 A1 | 12/2009 | Cossu et al. |
| 2009/0317885 A1 | 12/2009 | Mascharak |
| 2010/0003338 A1 | 1/2010 | Hubbell et al. |
| 2010/0015253 A1 | 1/2010 | Benjamin |
| 2010/0016790 A1 | 1/2010 | Peters |
| 2010/0021506 A1 | 1/2010 | Jones |
| 2010/0040703 A1 | 2/2010 | Miller et al. |
| 2010/0062055 A1 | 3/2010 | Herrmann et al. |
| 2010/0076162 A1 | 3/2010 | Ameer et al. |
| 2010/0086530 A1 | 4/2010 | Martinov |
| 2010/0087370 A1 | 4/2010 | Jain et al. |
| 2010/0099729 A1 | 4/2010 | Almirante et al. |
| 2010/0112033 A1 | 5/2010 | Ganzarolli de Oliveira et al. |
| 2010/0112095 A1 | 5/2010 | Morris et al. |
| 2010/0129474 A1 | 5/2010 | Benjamin et al. |
| 2010/0152683 A1 | 6/2010 | Lindgren et al. |
| 2010/0159119 A1 | 6/2010 | Chen et al. |
| 2010/0166603 A1 | 7/2010 | Opie |
| 2010/0178319 A1 | 7/2010 | Lindgren et al. |
| 2010/0184992 A1 | 7/2010 | Toone et al. |
| 2010/0196517 A1 | 8/2010 | Fossel |
| 2010/0197702 A1 | 8/2010 | Hellberg et al. |
| 2010/0197802 A1 | 8/2010 | Jezek et al. |
| 2010/0209469 A1 | 8/2010 | Bezwada |
| 2010/0221308 A1 | 9/2010 | Madhyastha et al. |
| 2010/0233304 A1 | 9/2010 | Pan |
| 2010/0239512 A1 | 9/2010 | Morris et al. |
| 2010/0247611 A1 | 9/2010 | Balkus, Jr. et al. |
| 2010/0247680 A1 | 9/2010 | Szabo |
| 2010/0249189 A1 | 9/2010 | Almirante et al. |
| 2010/0255062 A1 | 10/2010 | Kalivretenos et al. |
| 2010/0256755 A1 | 10/2010 | Chen et al. |
| 2010/0261930 A1 | 10/2010 | Honda et al. |
| 2010/0262238 A1 | 10/2010 | Chen et al. |
| 2010/0268149 A1 | 10/2010 | Av-Gay et al. |
| 2010/0276284 A1 | 11/2010 | Meyerhoff et al. |
| 2010/0280122 A1 | 11/2010 | Fossel |
| 2010/0285100 A1 | 11/2010 | Balkus, Jr. et al. |
| 2010/0303891 A1 | 12/2010 | Lee et al. |
| 2010/0311780 A1 | 12/2010 | Farber |
| 2010/0323036 A1 | 12/2010 | Fine |
| 2010/0324107 A1 | 12/2010 | Dos Santos et al. |
| 2010/0331542 A1 | 12/2010 | Smith |
| 2010/0331968 A1 | 12/2010 | Morris et al. |
| 2011/0008815 A1 | 1/2011 | Stamler et al. |
| 2011/0033437 A1 | 2/2011 | Smith et al. |
| 2011/0046182 A1 | 2/2011 | Gilmer et al. |
| 2011/0059036 A1 | 3/2011 | Arnold et al. |
| 2011/0059189 A1 | 3/2011 | Cisneros |
| 2011/0065783 A1 | 3/2011 | O'Donnell et al. |
| 2011/0070318 A1 | 3/2011 | Jezek et al. |
| 2011/0071168 A1 | 3/2011 | Chopp et al. |
| 2011/0076313 A1 | 3/2011 | Av-Gay et al. |
| 2011/0104240 A1 | 5/2011 | Jones et al. |
| 2011/0106000 A1 | 5/2011 | Jones et al. |

FOREIGN PATENT DOCUMENTS

| | | |
|---|---|---|
| EP | 0 746 327 B1 | 4/2004 |
| EP | 0 724 436 B1 | 7/2004 |
| EP | 1 411 908 B1 | 5/2005 |
| EP | 1 163 528 B1 | 11/2005 |
| EP | 1 681 068 A1 | 7/2006 |
| EP | 1 690 532 A1 | 8/2006 |
| EP | 1 690 554 A1 | 8/2006 |
| EP | 1 690 557 A1 | 8/2006 |
| EP | 1 690 558 A1 | 8/2006 |
| EP | 1 700 611 A1 | 9/2006 |
| EP | 1 704 876 A1 | 9/2006 |
| EP | 1 704 877 A1 | 9/2006 |
| EP | 1 704 879 A1 | 9/2006 |
| EP | 1 707 224 A1 | 10/2006 |
| EP | 1 728 438 A1 | 12/2006 |
| EP | I731 176 A1 | 12/2006 |
| EP | 1 757 278 A1 | 2/2007 |
| EP | 1 764 119 A1 | 3/2007 |
| EP | 1 790 335 A1 | 5/2007 |
| EP | 1 861 130 B1 | 9/2008 |
| EP | 1 343 547 B1 | 4/2009 |
| EP | 1 871 433 B1 | 4/2009 |
| EP | 1 161 248 B1 | 5/2009 |
| EP | 1 846 058 B1 | 7/2009 |
| WO | WO 95/07691 A1 | 3/1995 |

| | | |  | | | |
|---|---|---|---|---|---|---|
| WO | WO 95/10267 | A1 | 4/1995 | WO | WO 03/004097 A1 | 1/2003 |
| WO | WO 95/12394 | A1 | 5/1995 | WO | WO 03/006427 A1 | 1/2003 |
| WO | WO 95/19767 | A1 | 7/1995 | WO | WO 03/015605 A2 | 2/2003 |
| WO | WO 95/22335 | A1 | 8/1995 | WO | WO 03/015605 A3 | 2/2003 |
| WO | WO 95/32715 | A1 | 12/1995 | WO | WO 03/017989 A1 | 3/2003 |
| WO | WO 96/08966 | A1 | 3/1996 | WO | WO 03/026717 A1 | 4/2003 |
| WO | WO 96/13164 | A1 | 5/1996 | WO | WO 03/030659 A1 | 4/2003 |
| WO | WO 96/14844 | A1 | 5/1996 | WO | WO 03/041713 A1 | 5/2003 |
| WO | WO 96/15781 | A1 | 5/1996 | WO | WO 03/047636 A2 | 6/2003 |
| WO | WO 96/15797 | A1 | 5/1996 | WO | WO 03/047636 A3 | 6/2003 |
| WO | WO 96/27386 | A1 | 9/1996 | WO | WO 03/080039 A1 | 10/2003 |
| WO | WO 96/32118 | A1 | 10/1996 | WO | WO 03/092763 A1 | 11/2003 |
| WO | WO 96/32136 | A1 | 10/1996 | WO | WO 03/095398 A2 | 11/2003 |
| WO | WO 96/33757 | A1 | 10/1996 | WO | WO 03/095398 A3 | 11/2003 |
| WO | WO 96/35416 | A1 | 11/1996 | WO | WO 2004/009066 A1 | 1/2004 |
| WO | WO 97/16983 | A1 | 5/1997 | WO | WO 2004009253 A1 | 1/2004 |
| WO | WO 97/31654 | A1 | 9/1997 | WO | WO 2004/011421 A1 | 2/2004 |
| WO | WO 97/34014 | A1 | 9/1997 | WO | WO 2004/012874 A1 | 2/2004 |
| WO | WO 97/047254 | A1 | 12/1997 | WO | WO 2004/037798 A1 | 5/2004 |
| WO | WO 98/05689 | A1 | 2/1998 | WO | WO 2004/039313 A2 | 5/2004 |
| WO | WO 98/06389 | A1 | 2/1998 | WO | WO 2004/039313 A3 | 5/2004 |
| WO | WO 98/08482 | A2 | 3/1998 | WO | WO 2004/060283 A2 | 7/2004 |
| WO | WO 98/08482 | A3 | 3/1998 | WO | WO 2004/064767 A2 | 8/2004 |
| WO | WO 98/08496 | A1 | 3/1998 | WO | WO 2004/064767 A3 | 8/2004 |
| WO | WO 98/13358 | A1 | 4/1998 | WO | WO 2004/087212 A | 10/2004 |
| WO | WO 98/19996 | A1 | 5/1998 | WO | WO 2004/098538 A2 | 11/2004 |
| WO | WO 98/20015 | A1 | 5/1998 | WO | WO 2004/098538 A3 | 11/2004 |
| WO | WO 98/22090 | A1 | 5/1998 | WO | WO 2005/003032 A1 | 1/2005 |
| WO | WO 98/29101 | A1 | 7/1998 | WO | WO 2005/011575 A2 | 2/2005 |
| WO | WO 98/42661 | A1 | 10/1998 | WO | WO 2005/011575 A3 | 2/2005 |
| WO | WO 99/00070 | A1 | 1/1999 | WO | WO 2005/030118 A2 | 4/2005 |
| WO | WO 99/01427 | A2 | 1/1999 | WO | WO 2005/030118 A3 | 4/2005 |
| WO | WO 99/18949 | A1 | 4/1999 | WO | WO 2005/030135 A2 | 4/2005 |
| WO | WO 99/22729 | A1 | 5/1999 | WO | WO 2005/030135 A3 | 4/2005 |
| WO | WO 99/33823 | A1 | 7/1999 | WO | WO 2005/030147 A2 | 4/2005 |
| WO | WO 99/37616 | A1 | 7/1999 | WO | WO 2005/030147 A3 | 4/2005 |
| WO | WO 99/44595 | A2 | 9/1999 | WO | WO 2005/034860 A2 | 4/2005 |
| WO | WO 99/44595 | A3 | 9/1999 | WO | WO 2005/034860 A3 | 4/2005 |
| WO | WO 99/51221 | A1 | 10/1999 | WO | WO 2005/039664 A2 | 5/2005 |
| WO | WO 99/67210 | A1 | 12/1999 | WO | WO 2005/039664 A3 | 5/2005 |
| WO | WO 99/67296 | A1 | 12/1999 | WO | WO 2005/067986 A1 | 7/2005 |
| WO | WO 00/03640 | A1 | 1/2000 | WO | WO 2005/070006 A2 | 8/2005 |
| WO | WO 00/06151 | A1 | 2/2000 | WO | WO 2005/070006 A3 | 8/2005 |
| WO | WO 00/30658 | A1 | 6/2000 | WO | WO 2005/070008 A2 | 8/2005 |
| WO | WO 00/33877 | A1 | 6/2000 | WO | WO 2005/070008 A3 | 8/2005 |
| WO | WO 00/56333 | A1 | 9/2000 | WO | WO 2005/070874 A1 | 8/2005 |
| WO | WO 00/59304 | A1 | 10/2000 | WO | WO 2005/070883 A1 | 8/2005 |
| WO | WO 00/76318 | A1 | 12/2000 | WO | WO 2005/072819 A1 | 8/2005 |
| WO | WO 01/12067 | A1 | 2/2001 | WO | WO 2005/077962 A2 | 8/2005 |
| WO | WO 01/15738 | A2 | 3/2001 | WO | WO 2005/077962 A3 | 8/2005 |
| WO | WO 01/15738 | A3 | 3/2001 | WO | WO 2005/081752 A2 | 9/2005 |
| WO | WO 01/26702 | A2 | 4/2001 | WO | WO 2005/081752 A3 | 9/2005 |
| WO | WO 01/26702 | A3 | 4/2001 | WO | WO 2005/081964 A2 | 9/2005 |
| WO | WO 01/45732 | A2 | 6/2001 | WO | WO 2005/094913 A1 | 10/2005 |
| WO | WO 01/45732 | A3 | 6/2001 | WO | WO 2005/102282 A1 | 11/2005 |
| WO | WO 01/70199 | A1 | 9/2001 | WO | WO 2005/107384 A2 | 11/2005 |
| WO | WO 01/85227 | A2 | 11/2001 | WO | WO 2005/107384 A3 | 11/2005 |
| WO | WO 01/85227 | A3 | 11/2001 | WO | WO 2005/112954 A1 | 12/2005 |
| WO | WO 01/89572 | A1 | 11/2001 | WO | WO 2005/115440 A2 | 12/2005 |
| WO | WO 02/17880 | A2 | 3/2002 | WO | WO 2005/115440 A3 | 12/2005 |
| WO | WO 02/17880 | A3 | 3/2002 | WO | WO 2005/120493 A1 | 12/2005 |
| WO | WO 02/17881 | A2 | 3/2002 | WO | WO 2006/023693 A2 | 3/2006 |
| WO | WO 02/17881 | A3 | 3/2002 | WO | WO 2006/023693 A3 | 3/2006 |
| WO | WO 02/20026 | A2 | 3/2002 | WO | WO 2006/037105 A2 | 4/2006 |
| WO | WO 02/20026 | A3 | 3/2002 | WO | WO 2006/037105 A3 | 4/2006 |
| WO | WO 02/32418 | A1 | 4/2002 | WO | WO 2006/041855 A2 | 4/2006 |
| WO | WO 02/34705 | A2 | 5/2002 | WO | WO 2006/041855 A3 | 4/2006 |
| WO | WO 02/43786 | A2 | 6/2002 | WO | WO 2006/045639 A1 | 5/2006 |
| WO | WO 02/43786 | A3 | 6/2002 | WO | WO 2006/055542 A2 | 5/2006 |
| WO | WO 02/47675 | A1 | 6/2002 | WO | WO 2006/055542 A3 | 5/2006 |
| WO | WO 02/051353 | A2 | 7/2002 | WO | WO 2006/058318 A2 | 6/2006 |
| WO | WO 02/051353 | A3 | 7/2002 | WO | WO 2006/064056 A2 | 6/2006 |
| WO | WO 02/056864 | A2 | 7/2002 | WO | WO 2006/066362 A1 | 6/2006 |
| WO | WO 02/056864 | A3 | 7/2002 | WO | WO 2006/084909 A1 | 8/2006 |
| WO | WO 02/056874 | A2 | 7/2002 | WO | WO 2006/084910 A1 | 8/2006 |
| WO | WO 02/056904 | A1 | 7/2002 | WO | WO 2006/084911 A2 | 8/2006 |
| WO | WO 02/070496 | A1 | 9/2002 | WO | WO 2006/084912 A1 | 8/2006 |
| WO | WO 02/076395 | A2 | 10/2002 | WO | WO 2006/084913 A2 | 8/2006 |
| WO | WO 02/076395 | A3 | 10/2002 | WO | WO 2006/084914 A2 | 8/2006 |

| | | |
|---|---|---|
| WO | WO 2006/100155 AI | 8/2006 |
| WO | WO 2006/095193 A2 | 9/2006 |
| WO | WO 2006/095193 A3 | 9/2006 |
| WO | WO 2006/096572 A1 | 9/2006 |
| WO | WO 2006/097348 A1 | 9/2006 |
| WO | WO 2006/099058 A2 | 9/2006 |
| WO | WO 2006/099058 A3 | 9/2006 |
| WO | WO 2006/100154 A1 | 9/2006 |
| WO | WO 2006/100156 A2 | 9/2006 |
| WO | WO 2006/100156 A3 | 9/2006 |
| WO | WO 2006/122960 A1 | 11/2006 |
| WO | WO 2006/122961 A1 | 11/2006 |
| WO | WO 2006/125016 A1 | 11/2006 |
| WO | WO 2006/125262 A1 | 11/2006 |
| WO | WO 2006/127591 A2 | 11/2006 |
| WO | WO 2006/127591 A3 | 11/2006 |
| WO | WO 2006/128121 A2 | 11/2006 |
| WO | WO 2006/128742 A2 | 12/2006 |
| WO | WO 2006/128742 A3 | 12/2006 |
| WO | WO 2006/128743 A1 | 12/2006 |
| WO | WO 2006/130982 A1 | 12/2006 |
| WO | WO 2007/003028 A1 | 1/2007 |
| WO | WO 2007/005910 A2 | 1/2007 |
| WO | WO 2007/005910 A3 | 1/2007 |
| WO | WO 2007/012165 A1 | 2/2007 |
| WO | WO 2007/016677 A2 | 2/2007 |
| WO | WO 2007/016677 A3 | 2/2007 |
| WO | WO 2007/023005 A1 | 3/2007 |
| WO | WO 2007/024501 A2 | 3/2007 |
| WO | WO 2007/024501 A3 | 3/2007 |
| WO | WO 2007/027859 A1 | 3/2007 |
| WO | WO 2007/028657 A1 | 3/2007 |
| WO | WO 2007/030266 A2 | 3/2007 |
| WO | WO 2007/030266 A3 | 3/2007 |
| WO | WO 2007/050379 A2 | 5/2007 |
| WO | WO 2007/050379 A3 | 5/2007 |
| WO | WO 2007/053292 A2 | 5/2007 |
| WO | WO 2007/053578 A2 | 5/2007 |
| WO | WO 2007/053578 A3 | 5/2007 |
| WO | WO 2007/054373 A1 | 5/2007 |
| WO | WO 2007/057763 A | 5/2007 |
| WO | WO 2007/057763 A2 | 5/2007 |
| WO | WO 2007/057763 A3 | 5/2007 |
| WO | WO 2007/059311 A2 | 5/2007 |
| WO | WO 2007/059311 A3 | 5/2007 |
| WO | WO 2007/064895 A2 | 6/2007 |
| WO | WO 2007/064895 A3 | 6/2007 |
| WO | WO 2007/067477 A1 | 6/2007 |
| WO | WO 2007/084533 A2 | 7/2007 |
| WO | WO 2007/084533 A3 | 7/2007 |
| WO | WO 2007/086884 A2 | 8/2007 |
| WO | WO 2007/086884 A3 | 8/2007 |
| WO | WO 2007/088050 A2 | 8/2007 |
| WO | WO 2007/088050 A3 | 8/2007 |
| WO | WO 2007/088123 A2 | 8/2007 |
| WO | WO 2007/088123 A3 | 8/2007 |
| WO | WO 2007/092284 A2 | 8/2007 |
| WO | WO 2007/092284 A3 | 8/2007 |
| WO | WO 2007/100910 A2 | 9/2007 |
| WO | WO 2007/100910 A3 | 9/2007 |
| WO | WO 2007/103190 A2 | 9/2007 |
| WO | WO 2007/103190 A3 | 9/2007 |
| WO | WO 2007/127725 A2 | 11/2007 |
| WO | WO 2007/127725 A3 | 11/2007 |
| WO | WO 2007/133922 A2 | 11/2007 |
| WO | WO 2007/133922 A3 | 11/2007 |
| WO | WO 2007/143185 A2 | 12/2007 |
| WO | WO 2007/143185 A3 | 12/2007 |
| WO | WO 2007/149437 A1 | 12/2007 |
| WO | WO 2007/149520 A2 | 12/2007 |
| WO | WO 2007/149520 A3 | 12/2007 |
| WO | WO 2008/005313 A2 | 1/2008 |
| WO | WO 2008/005313 A3 | 1/2008 |
| WO | WO 2008/013633 A2 | 1/2008 |
| WO | WO 2008/013633 A3 | 1/2008 |
| WO | WO 2008/020218 A1 | 2/2008 |
| WO | WO 2008/027203 A2 | 3/2008 |
| WO | WO 2008/027203 A3 | 3/2008 |
| WO | WO 2008/062160 A1 | 5/2008 |
| WO | WO 2008/071242 A1 | 6/2008 |
| WO | WO 2008/088507 A2 | 7/2008 |
| WO | WO 2008/088507 A3 | 7/2008 |
| WO | WO 2008/095841 A2 | 8/2008 |
| WO | WO 2008/095841 A3 | 8/2008 |
| WO | WO 2008/098192 A2 | 8/2008 |
| WO | WO 2008/098192 A3 | 8/2008 |
| WO | WO 2008/100591 A2 | 8/2008 |
| WO | WO 2008/100591 A3 | 8/2008 |
| WO | WO 2008/112391 A2 | 9/2008 |
| WO | WO 2008/112391 A3 | 9/2008 |
| WO | WO 2008/116497 A1 | 10/2008 |
| WO | WO 2008/116925 A1 | 10/2008 |
| WO | WO 2008/130567 A1 | 10/2008 |
| WO | WO 2008/141416 A1 | 11/2008 |
| WO | WO 2008/150505 A1 | 12/2008 |
| WO | WO 2008/157393 A1 | 12/2008 |
| WO | WO 2009/014616 A1 | 1/2009 |
| WO | WO 2009/014829 A2 | 1/2009 |
| WO | WO 2009/014829 A3 | 1/2009 |
| WO | WO 2009/019498 A2 | 2/2009 |
| WO | WO 2009/019498 A3 | 2/2009 |
| WO | WO 2009/019499 A2 | 2/2009 |
| WO | WO 2009/026680 A1 | 3/2009 |
| WO | WO 2009/036571 A1 | 3/2009 |
| WO | WO 2009/049208 A1 | 4/2009 |
| WO | WO 2009/064861 A2 | 5/2009 |
| WO | WO 2009/064861 A3 | 5/2009 |
| WO | WO 2009/073643 A2 | 6/2009 |
| WO | WO 2009/073643 A3 | 6/2009 |
| WO | WO 2009/073940 A2 | 6/2009 |
| WO | WO 2009/073940 A3 | 6/2009 |
| WO | WO 2009/080795 A1 | 7/2009 |
| WO | WO 2009/086470 A2 | 7/2009 |
| WO | WO 2009/086470 A3 | 7/2009 |
| WO | WO 2009/088433 A1 | 7/2009 |
| WO | WO 2009/098113 A1 | 8/2009 |
| WO | WO 2009/117182 A2 | 9/2009 |
| WO | WO 2009/117182 A3 | 9/2009 |
| WO | WO 2009/117183 A1 | 9/2009 |
| WO | WO 2009/124379 A1 | 10/2009 |
| WO | WO 2009/131931 A1 | 10/2009 |
| WO | WO 2009/155689 A1 | 12/2009 |
| WO | WO 2009/155690 A1 | 12/2009 |
| WO | WO 2010/002450 A2 | 1/2010 |
| WO | WO 2010/002450 A3 | 1/2010 |
| WO | WO 2010/033242 A2 | 3/2010 |
| WO | WO 2010/033242 A3 | 3/2010 |
| WO | WO 2010/045465 A1 | 4/2010 |
| WO | WO 2010/048724 A1 | 5/2010 |
| WO | WO 2010/080213 A2 | 7/2010 |
| WO | WO 2010/080213 A3 | 7/2010 |
| WO | WO 2010/096320 A2 | 8/2010 |
| WO | WO 2010/096320 A3 | 8/2010 |
| WO | WO 2010/114669 A1 | 10/2010 |
| WO | WO 2010/120414 A2 | 10/2010 |
| WO | WO 2010/151505 A1 | 12/2010 |

OTHER PUBLICATIONS

Summersgill, J., et al., "Killing of *Legionella pneumophila* by nitric oxide in γ-interferon-activated macrophages," *Journal of Leukocyte Biology*, 1992, vol. 52, p. 625-629.

Tang, X., et al., "Synthesis of Beta-Lactamase Activated Nitric Oxide Donors," *Biorgania & Medicinal Chemistry Letters*, 2003, vol. 13, pp. 1687-1690.

Zhu, D., et al., "Corrosion protection of metals by water-based silane mixtures of bis-[trimethosysilylpropyl]amine and vinyltriacetoxysilane," *Progress in Organic Coatings*, 2004, vol. 49, pp. 42-53.

Albert et al., "Characterization of Bonded Phases by Solid-State NMR Spectroscopy," *Journal of Chromatography*, 1991, pp. 345-370, vol. 544.

Albina et al., "Role of Nitric Oxide in Mediation of Macrophage Cytotoxicity and Apoptosis," *Cancer and Metastasis Reviews*, 1998, pp. 39-53, vol. 17.

Anwander et al., "Silazane-Silylation of Mesoporous Silicates: Towards Tailor-Made Support Materials," *Mesoporous Molecular Sieves*, 1998, pp. 135-142, vol. 117.

Beckman et al., "Direct Measurement of Dilute Nitric Oxide in Solution with an Ozone Chemiluminescent Detector," *Methods: A Companion to Methods Enzymology*, 1995, pp. 35-39, vol. 7.

Brannon-Peppas et al., "Nanoparticle and Targeted Systems for Cancer Therapy," *Advanced Drug Delivery Reviews*, 2004, pp. 1649-1659, vol. 56.

Bruch et al., "Nuclear Magnetic Resonance Analysis of Silica Gel Surfaces Modified With Mixed, Amine-Containing Ligands," *Journal of Chromatography*, 2003, pp. 61-70, vol. 1021.

Brust et al., "Synthesis of Thiol-Derivatised Gold nanoparticles in a Two-Phase Liquid-Liquid System," *J. Chem. Soc., Chem. Comm.*, 1994, pp. 801-802.

Capala et al., "Boronated Epidermal Growth Factor as a Potential Targeting Agent for Boron Neutron Capture Therapy of Brain Tumors," *Bioconjugate Chem.*, 1996, pp. 7-15, vol. 7, No. 1.

Cobbs et al., "Expression of Nitric Oxide Synthase in Human Central Nervous System Tumors," *Cancer Res.*, 1995, pp. 727-730, vol. 55.

Davies et al., "Chemistry of the Diazeniumdiolates. 2. Kinetics and Mechanism of Dissociation to Nitric Oxide in Aqueous Solution," *J. Am. Chem. Soc.*, 2001, pp. 5473-5481, vol. 123.

Diodati et al. "Complexes of Nitric Oxide with Nucleophiles as Agents for the Controlled Biiological Release of Nitric Oxide: Antiplatelet Effect," *Thrombosis and Haemostasis*, 1993, pp. 654-658, vol. 70, Abstract.

Freireich et al., "Quatitative Comparison of Toxicity of Anticancer Agents in Mouse, Rat, Hamster, Dog, Monkey and Man," *Cancer Chemother Rep.* 1966, pp. 291-244, vol. 50, Abstract.

Frost et al., "Polymers Incorporating Nitric Oxide Releasing/Generating Sustances for Improved Biocompatibility of Blood-Contacting Medical Devices," *Biomaterials*, 2005, pp. 1685-1693, vol. 26.

Harris et al., "The Base-Catalyzed Hydrolysis and Condensation Reactions of Dilute and Concentrated Teos Solutions," *J. Non-Cryst. Solids*, 1990, pp. 397-403, vol. 121.

Hatton et al., "Past, Present, and Future of Periodic Mesoporous Organosilicas—The PMOs," *Acc. Chem. Res.*, 2005, vol. 38, pp. 305-312.

Hostetler et al., "Alkanethiolate Gold Cluster Molecules with Core Diameters From 1.5 to 5.2 nm: Core and Monolayer Properties as a Function of Core Size," *Langmuir*, 1998, pp. 17-30, vol. 14.

Hostetler et al., "Dynamics of Place-Exchange Reactions on Monolayer-Protected Gold Clusters Molecules," *Langmuir*, 1999, pp. 3782-3789, vol. 15.

Hrabie et al., "New Nitrate Oxide-Releasing Zwitterions Derived From Polyamines," *J. Org. Chem.* 1993, pp. 1472-1476, vol. 58.

Hrabie et al., "Chemistry of the Nitric Oxide-Releasing Diazeniumdiolate ("Nitrosohydroxylamine") Functional Group and Its Oxygen-Substituted Derivatives," *Chem. Rev.*, 2002, pp. 1135-1154, vol. 102.

Huh et al., "Organic Functionalization and Morphology Control of Mesoporous Silicas via a Co-Condensation Synthesis Method," *Chem. Mater.*, 2003, pp. 4247-4256, vol. 15.

Ignarro et al., "Endothelium-Derived Relaxing Factor Produced and Released From Artery and Vein is Nitric Oxide," *Proc. Natl. Acad. Sci., U.S.A.*, 1987, 9265-9269, vol. 84.

Jenkins et al., "Roles of Nitric Oxide in Tumor Growth," *Proc. Natl. Acad. Sci., U.S.A.*, 1995, 4392-4396, vol. 92.

Keefer, "Nitric Oxide-Releasing Compounds: From Basic Research to Promising Drugs," *Chemtech*, 1998, 30-35, vol. 28, No. 8, Abstract.

Keefer, "Progress Toward Clinical Application of the Nitric Oxide-Releasing Diazeniumdiolates," *Annu. Rev. Pharmacol. Toxicol.* 2003, 585-607, vol. 43.

Lai et al., "A Mesoporous Silica Nanosphere-Based Carrier System With Chemically Removable CdS nanoparticle Caps for Stimuli-Responsive Controlled Release of Neurotransmitters and Drug Molecules," *J. Am. Chem. Soc.*, 2003, pp. 4451-4459, vol. 125.

Lim et al., "Comparative Studies of Grafting and Direct Syntheses of Inorganic-Organic Hybrid Mesoporous Materials," 1999, *Chem. Mater.*, pp. 3285-3295, vol. 11.

Lin et al., "Structural and Morphological Control of Cationic Surfactant-Templated Mesoporous Silica," *Acc. Chem. Res.*, 2002, 927-935, vol. 35.

Marletta et al., "Unraveling the Biological Significance of Nitric Oxide," *BioFactors*, 1990, pp. 219-225, vol. 2, Abstract.

Marxer et al., "Preparation of Nitric Oxide (NO)—Releasing Sol-Gels for Biomaterial Applications," *Chem. Mater.*, 2003, pp. 4193-4199, vol. 15.

Munoz et al., "MCM-41 Organic Modifications as Drug Delivery Rate Regulator," *Chem. Mater.*, 2003, pp. 500-503, vol. 15.

Nablo et al., "Sol-Gel Derived Nitric-Oxide Releasing Materials That Reduce Bacterial Adhesion," *J. Am. Chem. Soc.*, 2001, pp. 9712-9713, vol. 123.

Napoli et al., "Nitric Oxide-Releasing Drugs," *Annu. Rev. Pharmacol. Toxicol.*, 2003, pp. 97-123, vol. 43.

Penault-Llorca et al., "Expression of *FGF* and *FGF* Receptor Genes in Human Breast Cancer," *Int. J. Cancer*, 1995, pp. 170-176, vol. 61.

Press et al., "Expression of the HER-2/neu Proto-Oncogene in Normal Human Adult and Fetal Tissues," *Oncogene*, 1990, pp. 953-962, vol. 5(7), Abstract.

Radomski et al., "The Anti-Aggregating Properties of Vascular Endothelium: Interactions Between Prostacyclin and Nitric Oxide," *Br. J. Pharmacol.*, 1987, pp. 639-646, vol. 92, No. 3, Abstract.

Radu et al., "A Polyamidoamine Dendrimer-Capped Mesoporous Silica Nanosphere-Based Gene Transfection Reagent," *J. Am. Chem. Soc.*, 2004, pp. 13216-13217, vol. 126.

Roy et al., "Optical Tracking of Organically Modified Silica Nanoparticles ad DNA Carriers: A Nonviral, Nanomedicine Approach for gene Delivery," *Proc. Natl. Acad. Sci, U.S.A.*, 2005, 279-284, vol. 102.

Sayari et al., "Periodic Mesoporous Silica-Based Organic-Inorganic Nanocomposite Materials," *Chem. Mater.*, 2001, pp. 3151-3168, vol. 13.

Shi et al., Comprehensive Characterization of Surface-Functionalized Poly(amidoamine) Dendrimers with Aceta*Colloids Surf. A*, 272, 139-150 (2006).

Stein et al., "Hybrid Inorganic-Organic Mesoporous Silicates—Nanoscopic Reactors Coming of Age," *Adv. Mater.*, 2000, pp. 1403-1419, vol. 12, No. 19.

Thomas et al., "In Vitro Targeting of Synthesized Antibody-Conjugated Dendrimer Nanoparticles," *Biomacromolecules*, 2004, pp. 2269-2274, vol. 5, Abstract.

Thomsen et al., "Nitric Oxide Synthase Activity in Human Breast Cancer," *Br. J. Cancer.*, 1995, 41-44, vol. 72, No. 1.

Trewyn et al., "Morphological Control of Room-Temperature ionic Liquid Templated Mesoporous Silica Nanoparticles for Controlled Release of Antibacterial Agents," *Nano. Letters*, 4, 2004, pp. 2139-2143, vol. 4, No. 11.

Troughton et al., "Monolayer Films Prepared by the Spontaneous Self-Assembly of Symmetrical and Unsymmetrical Dialkyl Sulfides from Solution onto Gold Substrates: Structure, Properties, and Reactivity of Constituent Functional Groups," *Langmuir*, 1988, pp. 365-385, vol. 4.

Wang et al., "Nitric Oxide Donors: Chemical Activities and Biological Applications," *Chem. Rev.*, 2002, pp. 1091-1134, vol. 102.

Wang et al., *Nitric Oxide Donors: For Pharmaceutical and Biological Applications*; Wiley-VCH: Weinheim, Germany, 2005, pp. 1-25.

Wiener et al., "Dendrimer-Based Metal Chelates: A New Class of Magnetic Resonance Imaging Contrast Agents," *Invest. Radiol.*, 1997, pp. 748-754, vol. 32, No. 12.

Wiener et al., "Targeting Dendrimer-Chelates to Tumors and Tumor Cells Expressing the High-Affinity Folate Receptor," *Magn. Reson. Med.* 1994, pp. 1-8, vol. 31, No. 1, Abstract.

Yoshitake, "Highly-Controlled Synthesis of Organic Layers on Mesoporous Silica: Their Structure and Application to Toxic Ion Adsorptions," *New. J. Chem.*, 2005, pp. 1107-1117, vol. 29.

Zhang et al., "Nitric Oxide-Releasing Fumed Silica Particles: Synthesis, Characterization, and Biomedical Application," *J. Am. Chem. Soc.*, 2003, pp. 5015-5024, vol. 125.

Zhou et al., "Polymethacrylate-Based Nitric Oxide Donors with Pendant *N*-Diazeniumdiolated Alkyldiamine Moieties: Synthesis, Characterization, and Preparation of Nitric Oxide Releasing Polymeric Coatings," *Biomacromolecules*, 2005, pp. 780-789, vol. 6.

Notification of Transmittal of the International Search Report and the Written Opinion of the International Searching Authority, or the Declaration for International Application No. PCT/US06/20781 (May 30, 2006).

Wang et al., "Dual-Luminophore-Doped Silica Nanoparticles for Multiplexed Signaling," *Nano Letters* 5, 37-43 (2005).

Deng et al., "Control of Surface Expression of Functional Ggroups on Silica Particles," *Materials Science and Engineering* C 11, 165-172, 165 (2000).

Barbé et al., Silica Particles: A Novel Drug-Delivery System, *Adv. Mater.* 16, 1959-66 (2004).

Amadeu et al., "Nitric Oxide Donor Improves Healing if Applied on Inflammatory and Proliferative Disease," *J. Surgical Research*, 2008, vol. 149, pp. 84-93.

Bohl Masters, K., et al., "Effects of nitric oxide releasing vinyl poly(vinyl alcohol) hydrogel dressings on dermal wound healing in diabetic mice," *Wound Repair and Regeneration*, 2002, vol. 10(5), pp. 286-294.

Brennan, P., et al., "The role of nitric oxide in oral diseases," *Archives of Oral Biology*, 2003, vol. 48, pp. 93-100.

Caplus[ONLINE], "NO Releasing Gold Nanoparticles: Synthesis and Characterization," Accession No. 2004:982821, 2004, 1 page.

"Examiner's first report on patent application No. 2006249323," for Australian Application No. 2006249323, 2010, 2 pages.

"Examiner's report No. 2 on patent application No. 2006249323," for Australian Application No. 2006249323, 2012, 3 pages.

Dobmeier, K. et al., "Antibacterial Properties of Nitric Oxide-Releasing Sol-Gel Microarrays," *Biomacromolecules*, 2004, vol. 5(6), pp. 2493-2495.

Hetrick, E., et al., "Antibacterial Nitric Oxide-Releasing Xerogels: Cell Viability and Parallel Plate Flow Cell Adhesion Studies," *Biomaterials*, 2007, vol. 28(11) pp. 1948-1956.

Hetrick, E., et al., "Reducing Implant-Related Infections: Active Release Strategies," *Chem. Soc. Rev*, 2006, vol. 36, pp. 780-789.

Hetrick, E., et al., "Bacterial Efficacy of Nitric Oxide-Releasing Silica Nanoparticles," *Acsnano*, 2008, vol. 2(2), pp. 235-246.

Hetrick, E., et al., "Anti-biofilm efficacy of nitric oxide-releasing silica nanoparticles," *Biomaterials*, 2009, vol. 30, pp. 2782-2789.

International Search Report and Written Opinion for corresponding PCT Application No. PCT/US2009/005643, Date of mailing May 24, 2010.

Iwakir, N. et al., "Synthesis of Amphiphillic polysiloxanes and their properties for formation of nano-aggregates," *Colloid Polym Sci*, 2009, vol. 287, pp. 577-582.

Living Water Acid-Alkaline Balance http://www.livingwaterhealthsolutions.com/Articles/alkalize.php, accessed online Nov. 3, 2011.

Nablo, B. et al., "Nitric Oxide-Releasing Sol-Gels as Antibacterial Coatings for Orthopedic Implants," *Biomaterials*, 2005, vol. 26(8), pp. 917-924.

Nablo, B., et al., "Inhibition of Implant-Associated Infections via Nitric Oxide Release," *Biomaterials*, 2005, vol. 26(34), pp. 6984-6990.

Notification of Transmittal of the International Search Report and the Written Opinion of the International Searching Authority, or the Declaration corresponding to International Application No. PCT/US2010/046173, mailed Dec. 6, 2010, 20 pages.

Notification of the Transmittal of the International Search Report and the Written Opinion of the International Searching Authority, or the Declaration; International Search Report; Written Opinion of the International Search Authority corresponding to PCT/US2010/046209, mailed May 23, 2011, 13 pages.

Notification of the Transmittal of the International Search Report and the Written Opinion of the International Searching Authority, or the Declaration; International Search Report; Written Opinion of the International Searching Authority corresponding to PCT/US2010/052460, mailed Jan. 24, 2011, 10 pages.

Notification Concerning Transmittal of Copy of International Preliminary Report on Patentability for corresponding PCT application No. PCT/US2009/005643, mailed Apr. 28, 2011.

Office Action for Japanese Patent Application No. 2008-513811, Apr. 9, 2012, English Translation only, 4 pages.

Pulfer, S., et al., "Incorporation of nitric oxide-releasing crosslinked polyethyleneimine microspheres into vascular grafts," *J Biomed Mater Res*, 1997, vol. 37(2), pp. 182-189.

Robson, M., "Wound Infection. A Failure of Wound Healing Caused by an Imbalance of Bacteria," *Surg Clin North Amer*, 1997, vol. 77(3), pp. 637-650.

Saaral, N., "The Equilibrium Between Endothelin-1/Nitric Oxide in Acne Vulgaris," *Istanbul Tip Fakultesi Dergisi Cilt*, 2008, vol. 71(4), pp. 101-105.

Sato, E., et al., "Dynamic Aspect of Reactive Oxygen and Nitric Oxide in Oral Cavity," *J. Clin. Biochem. Nutr.*, 2008, vol. 42, pp. 8-13.

Salivary pH Testing https://allicincenter.com/pdf/ph_testing.pdf, Accessed online Nov. 3, 2011.

Schaffer, M., et al., "Diabetes-impaired healing and reduced wound nitric oxide synthesis: a possible pathophysiologic correlation," *Surgery*, 1997, vol. 121(5), pp. 513-519.

Shi, H., et al., "The role of iNOS in wound healing," *Surgery*, 2001, vol. 130(2), pp. 225-229.

Shin, J., at al., "Nitric Oxide-Releasing Sol-Gel Particle/Polyurethane Glucose Biosensors," *Anal Chem*, 2004, vol. 76, pp. 4543-4549.

Slowing, I., et al., "Mesoporous Silica Nanoparticles As Controlled Release Drug Delivery And Gene Transfection Carriers" *Adv. Drug Del. Rev.* (2008), vol. 60, pp. 1278-1288.

United States Patent and Trademark Office, Office Action for U.S. Appl. No. 13/157,036, mailed Mar. 16, 2012, 14 pages.

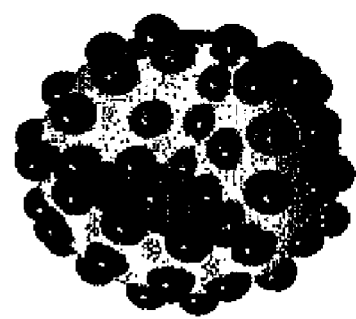
B
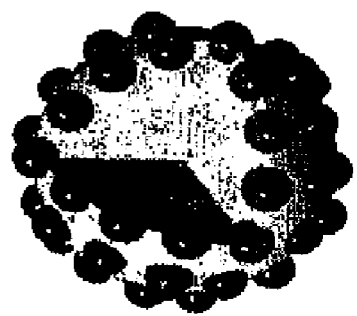
A
Fig. 4

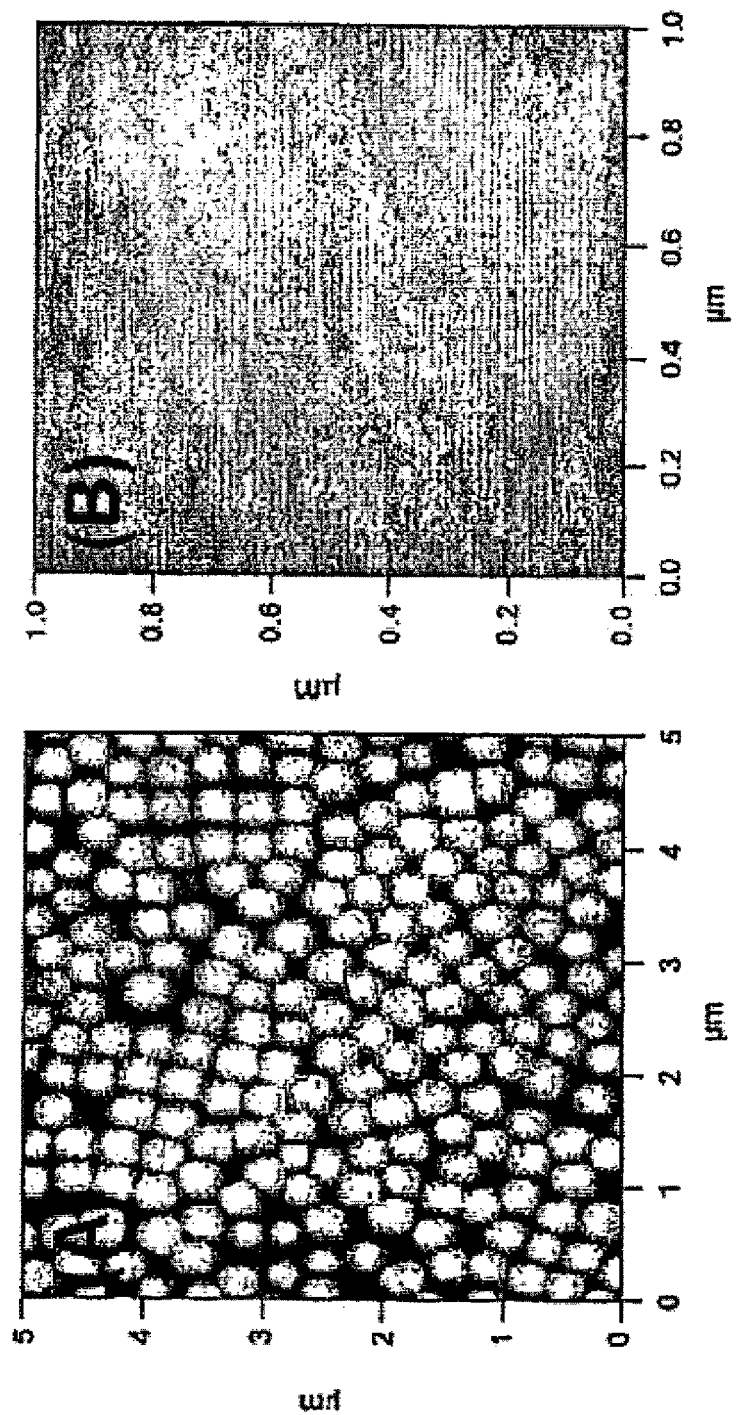
Fig. 20A&B

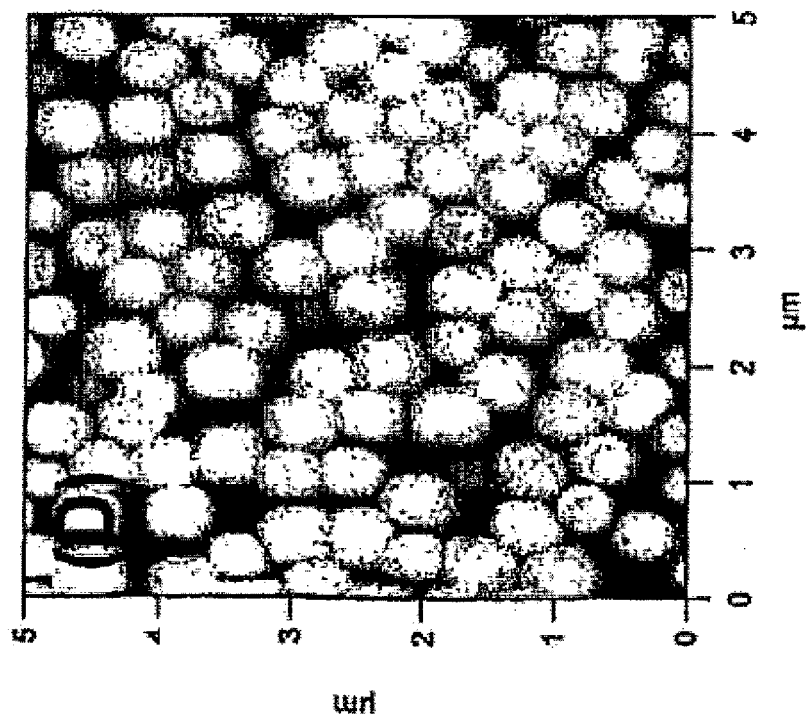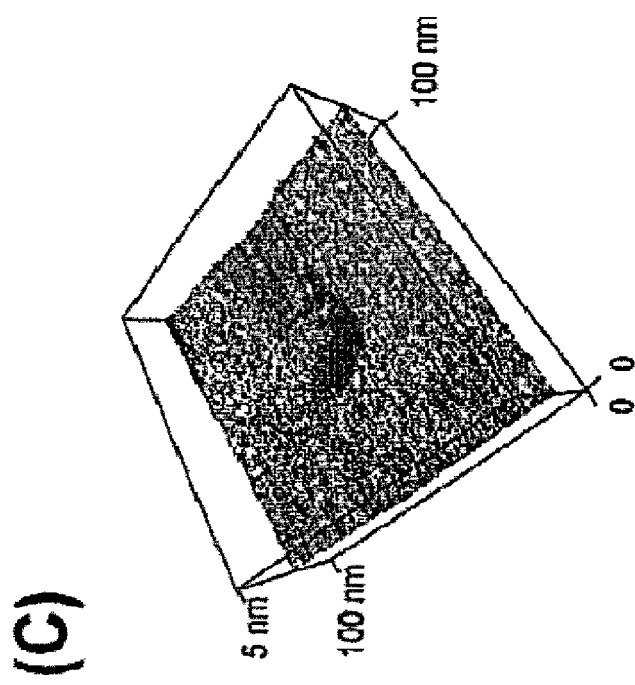
Fig. 20C&D

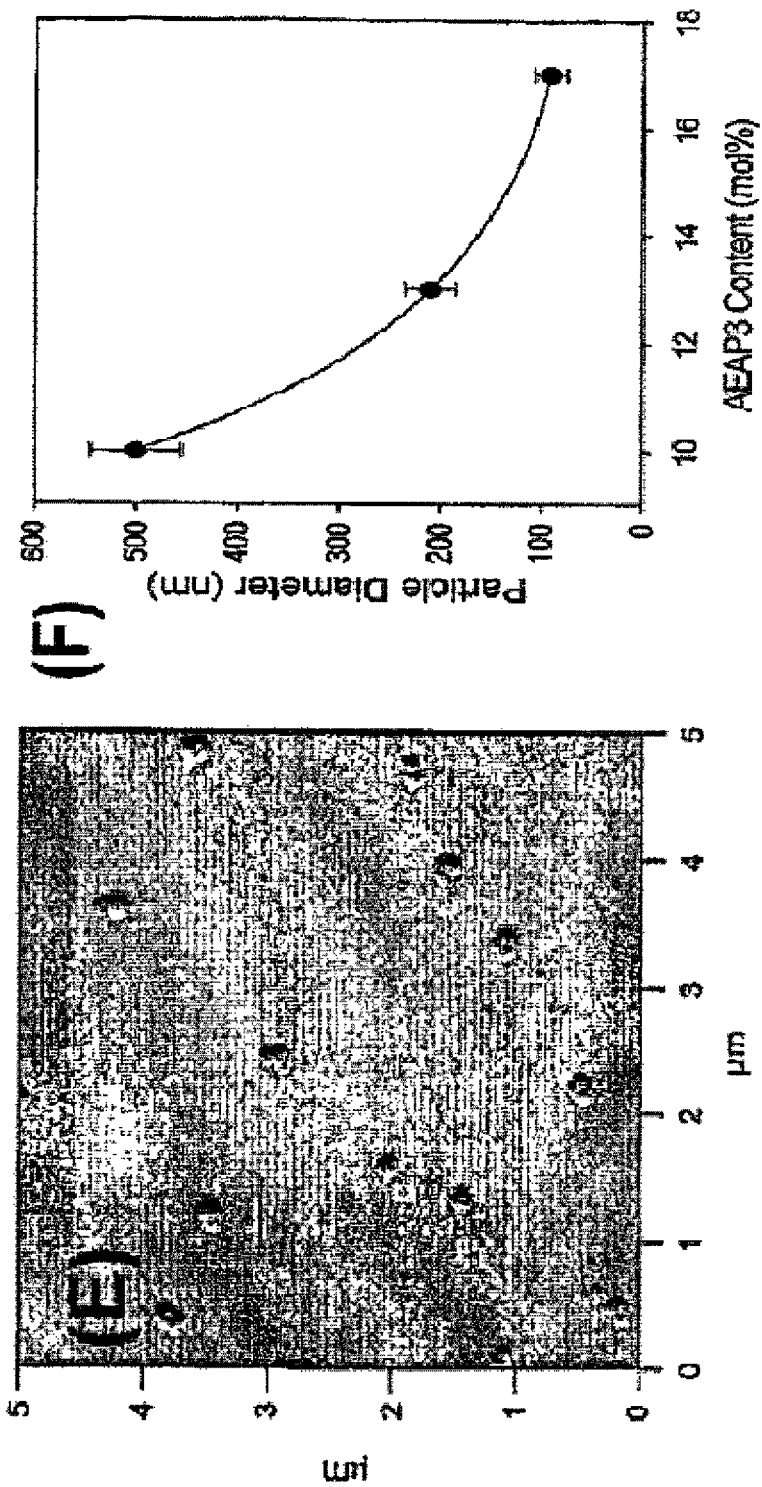
Figs. 20E&F

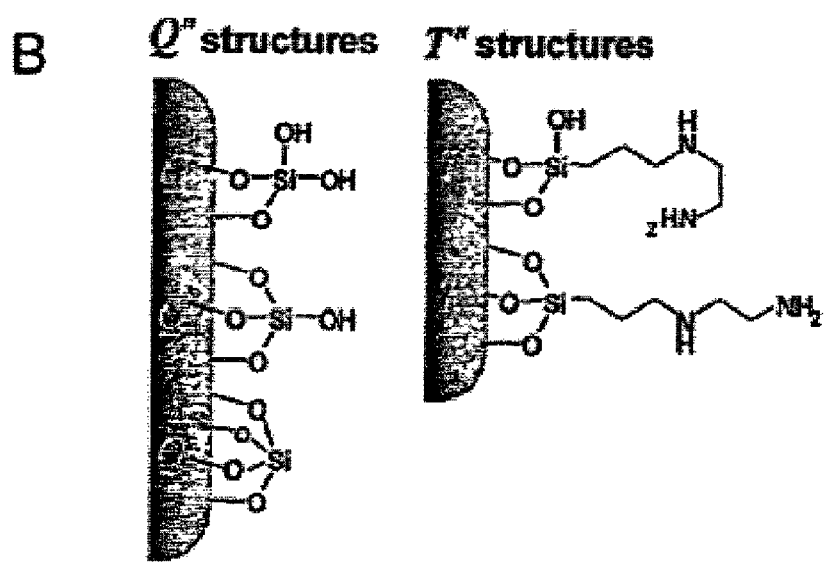
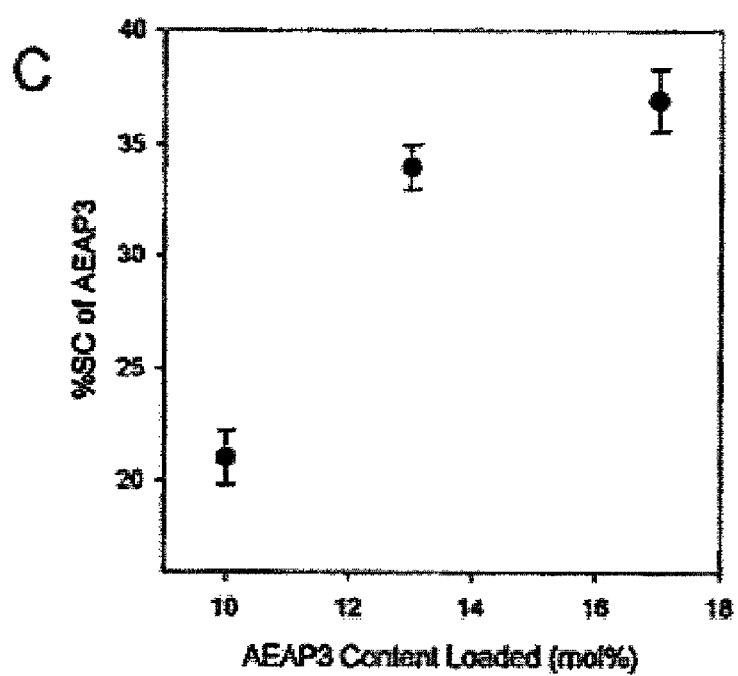
*Fig. 21B&C*

A

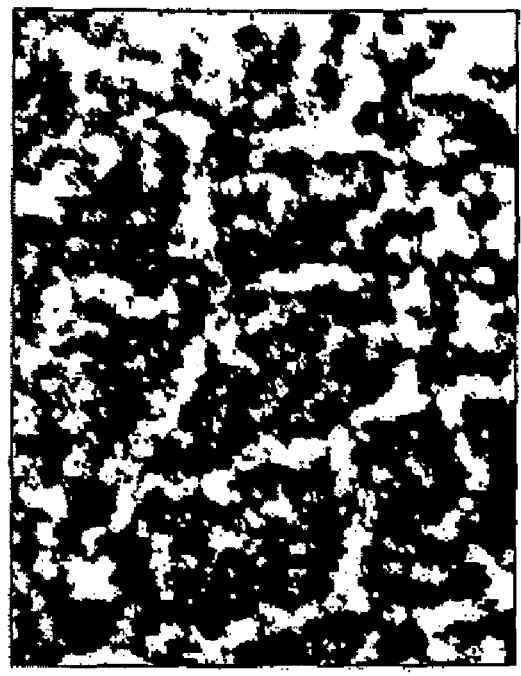
Fig. 35

NITRIC OXIDE-RELEASING PARTICLES FOR NITRIC OXIDE THERAPEUTICS AND BIOMEDICAL APPLICATIONS

RELATED APPLICATIONS

This application is a continuation of U.S. patent application Ser. No. 13/157,036, filed Jun. 9, 2011, which is a continuation of U.S. patent application Ser. No. 11/887,041, filed Jan. 15, 2009, which claims the benefit of U.S. Provisional Patent Application Ser. No. 60/685,578, filed May 27, 2005; the disclosure of which is incorporated herein by reference in its entirety.

GOVERNMENT INTEREST

This invention was made with U.S. Government support from National Institutes of Health Grant Number EB 000708. Thus, the U.S. Government has certain rights in the invention.

TECHNICAL FIELD

The presently disclosed subject matter provides nitric oxide-releasing particles and their use in biomedical and pharmaceutical applications. More particularly, in some embodiments, the presently disclosed subject matter provides particles that release nitric oxide in a controlled and targeted manner, thereby prolonging the therapeutic effects of nitric oxide and improving the specificity of nitric oxide delivery to targeted cells and/or tissues.

| ABBREVIATIONS | |
|---|---|
| AFM = | atomic force microscopy |
| AEAP3 = | N-(6-aminoethyl)-aminopropyltrimethoxysilane |
| AEMP3 = | (aminoethylaminomethyl)-phenethyl trimethoxysilane |
| AHAP3 = | N-(6-aminohexyl)-aminopropyltrimethoxysilane |
| AIBN = | α,α'-azobisisobutyronitrile |
| atm = | atmosphere |
| BSA = | bovine serum albumin |
| ° C. = | degrees Celsius |
| CFU = | colony forming units |
| CP/MAS = | cross polarization/magic angle spinning |
| CTAB = | cetyltrimethyl ammonium bromide |
| DET3 = | N-[3-(trimethyoxysilyl)propyl]-diethylenetriamine |
| EtOH = | ethanol |
| FA = | folic acid |
| FITC = | fluorescein isothiocyanate |
| g = | grams |
| GOx = | glucose oxidase |
| h = | hours |
| HPU = | hydrophilic polyurethane |
| MAP3 = | methylaminopropyl trimethoxysilane |
| MeOH = | methanol |
| mg = | microgram |
| μm = | micrometers |
| min = | minutes |
| mL = | milliliter |
| mol % = | mole percent |
| MPC = | monolayer protected cluster |
| MRI = | magnetic resonance imaging |
| MTMOS = | methyltrimethoxysilane |
| nA = | nanoampere |
| NaOMe = | sodium methoxide |
| nm = | nanometer |
| NMR = | nuclear magnetic resonance |
| NO = | nitric oxide |
| $[NO]_m$ = | maximum flux of nitric oxide release |
| $O_3$ = | ozone |

| ABBREVIATIONS | |
|---|---|
| OD = | optical density |
| PAMAM = | polyamidoamine |
| pmol = | picomole |
| ppb = | parts-per-billion |
| PPI = | polypropylenimine |
| ppm = | parts-per-million |
| TPU = | TECOFLEX ® polyurethane |
| TEM = | transmission electron microscopy |
| TEOS = | tetraethyl orthosilicate |
| TGA = | thermal gravimetric analysis |
| TMOS = | tetramethyl orthosilicate |
| TMRM = | tetramethylrhodamine |
| t[NO] = | total amount of nitric oxide |
| UV = | ultraviolet |
| Vis = | visible |

BACKGROUND

The discovery of the multifaceted role of nitric oxide (NO) in biology, physiology, and pathophysiology, see Marietta, M. A., at al., *BioFactors*, 2, 219-225 (1990), has led to the search for nitric oxide donors capable of controlled nitric oxide release. See Keefer, L. K., *Chemtech*, 28, 30-35 (1998). To date, researchers have discovered that NO regulates a range of biological processes in the cardiovascular, gastrointestinal, genitourinary, respiratory, and central and peripheral nervous systems. See Ignarro, L. J., *Nitric Oxide: Biology and Pathobiology*; Academic Press: San Diego, 2000; and Ignarro, L. J. et al., *Proc. Natl. Acad. Sci., USA.*, 84, 9265-9269 (1987). Furthermore, the discovery of NO as a vasodilator and its identification as both an antibiotic and a tumoricidal factor have made NO an attractive pharmaceutical candidate. See, for example, Radomski, M. W., et al., *Br. J. Pharmacol.*, 92, 639-646 (1987); Albina, J. E., and Reichner, J. S.; *Canc. Metas. Rev.*, 17, 19-53 (1998); Nablo, B. J., at al., *J. Am. Chem. Soc.*, 123, 9712-9713 (2001); Cobbs, C. S., et al., *Cancer Res.*, 55, 727-730 (1995); Jenkins, D. C., at al., *Proc. Natl. Acad. Sci., USA.*, 92, 4392-4396 (1995); and Thomsen, L. L., et al., *Br. J. Cancer.*, 72, 41-44 (1995).

Several nitric oxide donors have been reported, the most notable being N-diazeniumdiolates. Generally, N-diazeniumdiolate NO donors are small molecules synthesized by the reaction of amines with NO at elevated pressure and have been used, for example, to spontaneously generate NO in aqueous solution. See Hrabie, J. A. and Keefer, L. K., *Chem. Rev.*, 102, 1135-1154 (2002).

Therapeutic strategies to explore the activities of nitric oxide donors, for example, to kill tumor cells, are problematic in part because the nitric oxide delivery systems known in the art release or donate nitric oxide indiscriminately. Thus, there is a need in the art for a nitric oxide delivery system that releases or donates nitric oxide in a controlled and/or targeted manner to facilitate an improved understanding of the function of NO in physiology and to provide for the development of NO-associated therapies.

SUMMARY

In some embodiments, the presently disclosed subject matter provides a nitric oxide (NO)-releasing particle, comprising a nitric oxide donor, an exterior region, and an interior region having a volume, the volume of the interior region at least partially filled by a core selected from the group consisting of:

(a) a metallic cluster;
(b) a dentritic network;
(c) a co-condensed silica network; and
(d) a combination thereof.

In some embodiments, the interior region further comprises an organic linker selected from the group consisting of a labile linker responsive to changes in pH, a labile linker sensitive to electromagnetic radiation, a labile linker susceptible to degradation by enzymatic action, a hydrophobic linker, an amphiphilic linker, and combinations thereof.

In some embodiments, the NO donor is selected from the group consisting of a diazeniumdiolate, a nitrosamine, a hydroxylamine, a nitrosothiol, a hydroxylamine, and a hydroxyurea. In some embodiments the NO donor is covalently bound to one of the interior region, the exterior region, the core, or to combinations thereof. In some embodiments the NO donor is encapsulated in one of the interior region, the exterior region, the core, or to combinations thereof. In some embodiments the NO donor is associated with part of the particle via a non-covalent interaction selected from the group consisting of Van der Waals interactions, electrostatic forces, hydrogen bonding, or combinations thereof.

In some embodiments, the exterior region comprises one or more chemical moieties selected from the group consisting of moities that modulate the nitric oxide release kinetics, affect the biocompatibility or the biodistribution of the particle, provide for targeted delivery of the particle, impart an ability to image or track the particle, affect the solubility of the particle, provide a therapeutic effect, or combinations thereof.

In some embodiments, the core is a metallic cluster further comprising a component selected from the group consisting of gold, platinum, silver, magnetite, a quantum dot, or combinations thereof. In some embodiments, the metallic cluster is a monolayer protected gold cluster.

In some embodiments, the core is a dendritic network selected from the group consisting of a polypropylenimine dendrimer, a polyamidoamine dendrimer, a polyaryl ether dendrimer, a polypeptide dendrimer, a polyester dendrimer, a polyamide dendrimer, a dendritic polyglycerol, and a triazine dendrimer. In some embodiments the dendritic network is hyperbranched.

In some embodiments, the core is a co-condensed silica network synthesized from the condensation of a silane mixture comprising an alkoxysilane and an aminoalkoxysilane. In some embodiments, the alkoxysilane is a tetraalkoxysilane of the formula Si $(OR)_4$, wherein R is alkyl, and the aminoalkoxysilane has a formula selected from:
(a) an aminoalkoxysilane of the formula R"—(NH—R')$_n$—Si(OR)$_3$, wherein R is alkyl, R' is alkylene, branched alkylene, or aralkylene, n is 1 or 2, and R" is selected from the group consisting of alkyl, cycloalkyl, aryl, and alkylamine;
(b) an aminoalkoxysilane of the formula NH[R'—Si(OR)$_3$]$_2$, wherein R is alkyl and R' is alkylene;
(c) an aminoalkoxysilane wherein the amine is substituted by a diazeniumdioiate, said aminoalkoxysilane having the formula R"—N(NONCYX+)—R'—Si(OR)3, wherein R is alkyl, R' is alkylene or aralkylene, R" is alkyl or alkylamine, and X+ is a cation selected from the group consisting of Na+ and K+; and
(d) a combination thereof.

In some embodiments the siline mixture comprises between about 10 mol % to about 99 mol % of tetraalkoxysilane and about 1 mol % to about 90 mol % of aminoalkoxysilane. In some embodiments, the silane mixture further comprises about 0 mol % to about 20 mol % of fluorinated silane; about 0 mol % to about 20 mol % of cationic or anionic silane; and about 0 mol % to about 20 mol % of alkylsilane.

In some embodiments, the tetraalkoxysilane is selected from group consisting of tetramethyl orthosilicate and tetraethyl orthosilicate.

In some embodiments, the aminoalkoxysilane is selected from the group consisting of:
N-(6-aminohexyl)aminomethyltrimethoxysilane;
N-(6-aminohexyl)aminopropyltrimethoxysilane;
N-(6-aminoethyl)aminopropyltrimethoxysilane;
(3-trimethoxysilylpropyl)diethylenetriamine;
(aminoethylaminomethyl)phenethyltrimethoxysilane;
[3-(methylamino)propyl]trimethoxysilane;
N-butylaminopropyltrimethoxysilane;
N-ethylaminoisobutyltrimethoxysilane;
N-phenylaminopropyltrimethoxysilane;
N-cyclohexylaminopropyltrimethoxysilane;
Bis[3-(trimethoxysilyl)propyl]amine; and
Bis[(3-trimethoxysilyl)propyl]ethylenediamine.

In some embodiments the fluorinated silane is selected from the group consisting of
(heptadecafluoro-1,1,2,2-tetrahydrodecyl)⁻ triethoxysilane,
(3,3,3-trifluoropropyl)trimethoxysilane, and (perfluoroalkyl)
ethyltriethoxysilane.

In some embodiments, the cationic or anionic silane is selected from the group consisting of:
N—N-didecyl-N-methyl-N-(3-trimethoxysilyl)ammonium chloride;
octadecyldimethyl(3-trimethoxysilylpropyl)ammonium chloride;
3-trihydroxysilylpropylmethyl phosphonate, sodium salt; and carboxylethylsilanetriol, sodium salt.

In some embodiments the alkylsilane is selected from the group consisting of methyltrimethoxysilane, butyltrimethoxysilane, butyltriethoxysilane, propyltrimethoxysilane, and octadecyltrimethoxysilane.

In some embodiments, the NO-releasing particle comprising a co-condensed silica network core and the NO donor is synthesized using a "post-charging" method wherein the NO donor is formed after the condensation of the silica network in some embodiments, the NO-releasing particle comprising a co-condensed silica network core is synthesized using a "pre-charging" method wherein the NO donor is formed prior to the condensation of the silica network.

In some embodiments, the organic linker comprises a functional group capable of conferring an on/off state of nitric oxide release to the nitric oxide-releasing particle, wherein the functional group is selected from the group consisting of an ester, a hydrazone, an acetal, a thiopropionate, a photolabile moiety, and an amino acid sequence subject to enzymatic degradation.

In some embodiments, the exterior comprises a moiety capable of delivering the NO-releasing particle to a target. In some embodiments, the target is selected from a cell, a tissue, and an organ, In some embodiments, the cell is a cancer cell.

In some embodiments, the moiety capable of delivering the NO-releasing particle to the target is selected from the group consisting of a protein responsible for antibody/antigen interaction, folic acid, guanidine, transferrin, a hormone, carbohydrates, a peptide containing the amino acid sequence RGD, and TAT peptides.

In some embodiments, the exterior comprises a moiety selected from a nitric oxide donor, a (poly)ethyleneoxide, a (poly)urethane, an N-(2-hydroxypropyl)methacrylamide copolymer, Iactide/glycolide copolymers (e.g. poly(lactic-co-glycolic acid, PGA), a sugar, a fluorescent organic dye, an MRI contrast agent, a thiol, a methyl-terminated alkyl chain, an antibiotic, an anti-cancer therapeutic, a sulfonate, a carboxylate, a phosphate, a cationic amine, a quaternary amine, and combinations thereof.

In some embodiments, the NO-releasing particle has a diameter of from between about 1 nm and about 1000 nm. In some embodiments, the particle has a metallic cluster core and the diameter of the particle is from between about 1 nm and about 5 nm. In some embodiments the particle has a co-condensed silica network core and has a diameter of between about 2 nm and about 10 μm.

In some embodiments, the presently disclosed subject Matter provides a method or a formulation for delivering nitric oxide to a subject, in some embodiments, the method comprises administering an effective amount of a NO-releasing particle to the subject, said particle comprising a NO donor, an exterior region, and an interior region having a volume, the volume of the interior region at least partially filled by a core selected from:
 (a) a metallic cluster;
 (b) a dendritic network;
 (c) a co-condensed silica network; and
 (d) a combination thereof.

In some embodiments, the presently disclosed subject matter provides a method of treating a disease state in a subject in need of treatment thereof wherein the method comprises administering to a subject in need of treatment a NO-releasing particle comprising a NO donor, an exterior region, and an interior region having a volume, the volume at least partially filled by a core selected from:
 (a) a metallic cluster;
 (b) a dendritic network;
 (c) a co-condensed silica network; and
 (d) a combination thereof.

In some embodiments the disease state is selected from cancer, a cardiovascular disease, a microbial infection, platelet aggregation and platelet adhesion caused by the exposure of blood to a medical device, pathological conditions resulting from abnormal cell proliferation, transplantation rejections, autoimmune diseases, inflammation, vascular diseases; scar tissue, wound contraction, restenosis, pain, fever, gastrointestinal disorders, respiratory disorders, sexual dysfunctions, and sexually transmitted diseases.

In some embodiments, the presently disclosed subject matter provides polymeric films containing NO-releasing particles. In some embodiments the polymeric films can be used to coat medical devices. In some embodiments, the medical device is one of an arterial stent, a guide wire, a catheter, a trocar needle, a bone anchor, a bone screw, a protective plating, a hip or joint replacement, an electrical lead, a biosensor, a probe, a suture, a surgical drape, a wound dressing, and a bandage.

In some embodiments, the presently disclosed subject matter provides a detergent comprising a NO-releasing particle.

Thus, it is an object of the presently disclosed subject matter to provide nitric oxide-releasing particles. It is another object of the presently disclosed subject matter to provide nitric oxide-releasing particles for the targeted delivery of nitric oxide to a specific cell and/or tissue. It is another object of the presently disclosed subject matter to provide the ability to trigger the release of nitric oxide from nitric oxide-releasing particles.

Certain objects of the presently disclosed subject matter having been stated herein above, which are addressed in whole or in part by the presently disclosed subject matter, other objects and aspects will become evident as the description proceeds when taken in connection with the accompanying Examples as best described herein below.

BRIEF DESCRIPTION OF THE DRAWINGS

FIG. 4A is a schematic representation of the extent of NO donor distribution in N-diazeniumdiolate (darker spheres)-modified silica particles synthesized by a surface grafting method.

FIG. 4B is a schematic representation of the extent of NO donor distribution in N-diazeniumdiolate (darker spheres)-modified silica particles synthesized by "one-pot" co-condensation of silica networks from silane mixtures comprising alkoxysilanes and aminoalkoxysilanes.

FIG. 20A is a contact mode atomic force microscope (AFM) image of control silica (TEOS only).

FIG. 20B is a contact mode atomic force microscope (AFM) image of silica with 10 mol % of AHAP3 (balance TEOS).

FIG. 20C is an enlargement of the atomic force microscope (AFM) image from FIG. 29B showing a single particle.

FIG. 20D is a contact mode atomic force microscope (AFM) image of 10 mol % AEAP3.

FIG. 20E is a contact mode atomic force microscope (AFM) image of 17 mol % AEAP3 silica particles on a mica surface.

FIG. 20F is a graph showing the relationship between the AEAP3 content in the silica composite and the resulting particle size.

FIG. 21B is a schematic showing the structures related to the silicon chemical environments at the surface of AEAP3-modified silica composites.

FIG. 21C is a plot of % surface coverage of co-condensed amine ligands versus AEAP3 content loaded during the synthesis of AEAP3-modified silica composites.

FIG. 35A is a phase contrast optical micrograph showing P. aeruginosa adhesion (dark areas) to a control film (a non NO-releasing polyurethane). Magnification=5×.

FIG. 35B is a phase contrast optical micrograph showing P. aeruginosa adhesion (dark areas) to a NO-releasing particle-containing film. Magnification=5×.

DETAILED DESCRIPTION

Figure 1:
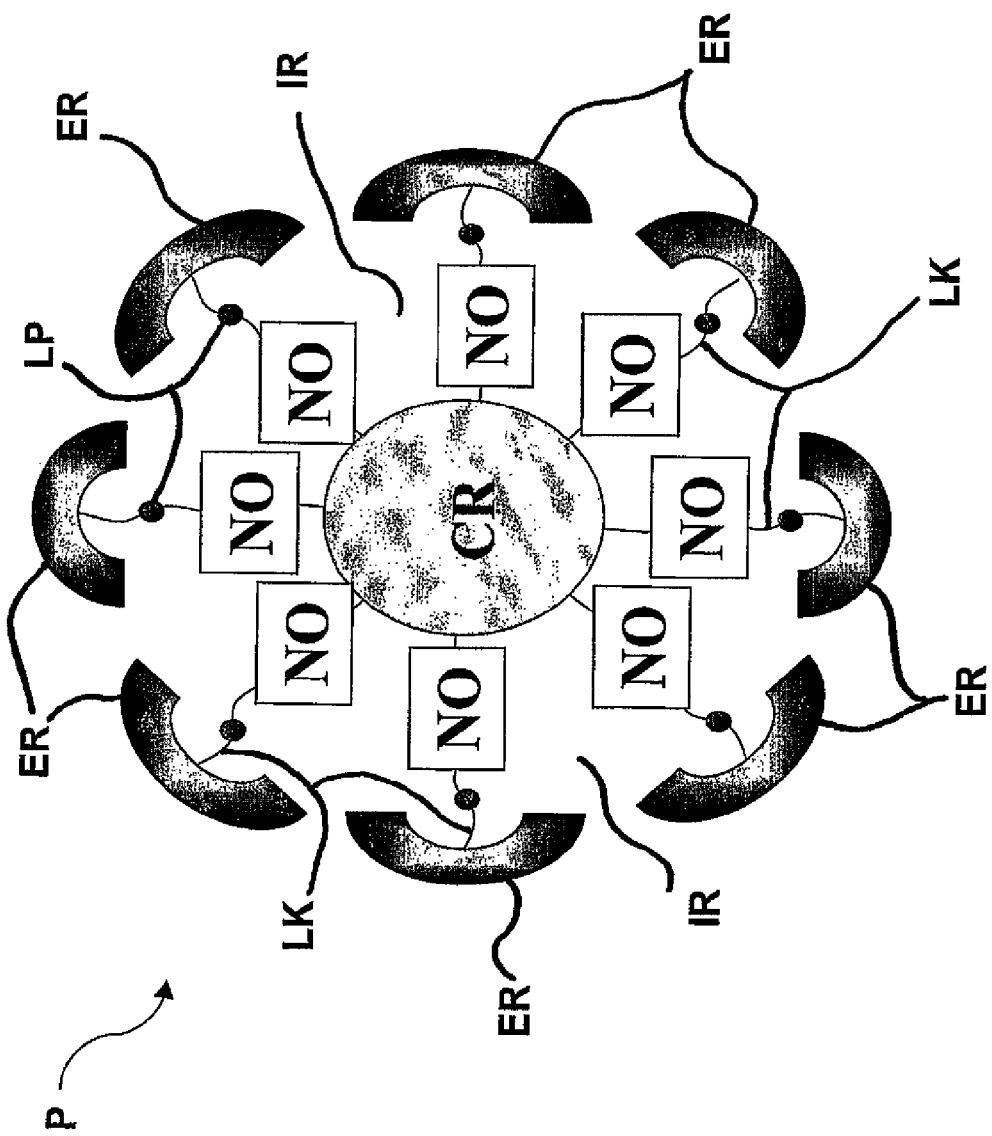
FIG. 1 is a schematic representation of a nitric oxide (NO)-releasing particle comprising a core CR, an interior region IR, a linker LK having a labile portion LP, a nitric oxide (NO) donor NO and an exterior EP.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

Following long-standing patent law convention, the terms "a" and "an" mean one or more when used in this application, including the claims.

The term "amphipathic" as used herein refers to a chemical moiety having a hydrophobic region and a hydrophilic region.

The term "cancer" as used herein refers to diseases caused by uncontrolled cell division and the ability of cells to metastasize, or to establish new growth in additional sites. The terms "malignant", "malignancy", "neoplasm", "tumor" and variations thereof refer to cancerous cells or groups of cancerous cells.

Specific types of cancer include, but are not limited to, skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood cancers, and lymphoid cancers.

As used herein, the term "electromagnetic radiation" refers to electric and magnetic waves such as, but not limited to, gamma rays, x-rays, ultraviolet light, visible light, infrared light, microwaves, radar and radio waves.

The term "hydrophobic" refers to a chemical compound or moiety that, to a given extent, repels or does not interact with water through non-covalent forces such as hydrogen bonding or electrostatic interactions. A compound can be strongly hydrophobic or slightly hydrophobic. The calculated dielectric constant of a compound or group can be used to predict the level or degree of hydrophobicity of the compound or moiety. Compounds or moieties with lower dielectric constants will be more hydrophobic. In particular, a "hydrophobic linker" is one that will protect a labile linker or a NO donor in a NO-releasing particle from exposure to water when the particle is placed in an aqueous environment for a period of time. A more hydrophobic linker will protect a NO donor or labile linker from water for a longer period of time.

The term "hydrophilic" refers to a compound or moiety that will interact with water to given extent.

The term "ionizable" refers to a group that is electronically neutral (La, uncharged) in a particular chemical environment (e.g., at a particular pH), but that can be ionized and thus rendered positively or negatively charged in another chemical environment (e.g., at a higher or lower pH).

The term "mesoporous" as used herein refers to an object, such as a particle, comprising pores in the range of between about 20-500 angstroms.

The term "metallic" refers to metals, metal alloys, metal salts, and metal oxides. Thus, the term metallic refers to particles comprising metal ions, such as, but not limited to, gold, silver, copper, platinum, and titanium, as well as semiconductor particles and magnetic particles (e.g., particles comprising iron oxides).

The terms "semiconductor nanocrystal" and "quantum dot" are used interchangeably herein to refer to semiconductor nanoparticles comprising an inorganic crystalline material that is luminescent (i.e., that is capable of emitting electromagnetic radiation upon excitation), and including an inner core of one or more first semiconductor materials that is optionally contained within an overcoating or "shell" of a second semiconductor material. A semiconductor nanocrystal core surrounded by a semiconductor shell is referred to as a "core/shell" semiconductor nanocrystal. The surrounding shell material can optionally have a bandgap energy that is larger than the bandgap energy of the core material and can be chosen to have an atomic spacing close to that of the core substrate.

Suitable semiconductor materials for the core and/or shell include, but are not limited to, materials comprising a first element selected from Groups 2 and 12 of the Periodic Table of the Elements and a second element selected from Group 16. Such materials include, but are not limited to ZnS, ZnSe, ZnTe, CDs, CdSe, CdTe, HgS, HgSe, HgTe, MgS, MgSe, MgTe, CaS, CaSe, CaTe, SrS, SrSe, SrTe, BaS, BaSe, BaTe, and the like. Suitable semiconductor materials also include materials comprising a first element selected from Group 13 of the Periodic Table of the Elements and a second element selected from Group 15. Such materials include, but are not limited to, GaN, GaP, GaAs, GaSb, InN, inP, InAs, 1 nSb, and the like. Semiconductor materials further include materials comprising a Group 14 element (Ge, Si, and the like); materials such as PbS, PbSe and the like; and alloys and mixtures thereof. As used herein, all reference to the Periodic Table of the Elements and groups thereof is to the new IUPAC system for numbering element groups, as set forth in the Handbook of Chemistry and Physics, 81 st Edition (CRC Press, 2000).

By "luminescence" is meant the process of emitting electromagnetic radiation (light) from an object. Luminescence results when a system undergoes a transition from an excited state to a lower energy state with a corresponding release of energy in the form of a photon. These energy states can be electronic, vibrational, rotational, or any combination thereof. The transition responsible for luminescence can be stimulated through the release of energy stored in the system chemically or added to the system from an external source. The external source of energy can be of a variety of types including chemical, thermal, electrical, magnetic, electromagnetic, and physical, or any other type of energy source capable of causing a system to be excited into a state higher in energy than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

The term "fluorescent" refers to a compound or chemical group that emits light following exposure to electromagnetic radiation.

The terms "nitric oxide donor" or "NO donor" refer to species that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The terms "nitric oxide releasing" or "nitric oxide donating" refer to methods of donating, releasing and/or directly or indirectly transferring any of the three redox forms of nitrogen monoxide (NO+, NO−, NO). In some cases, the nitric oxide releasing or donating is accomplished such that the biological activity of the nitrogen monoxide species is expressed at the intended site of action.

The term "microbial infection" as used herein refers to bacterial, fungal, viral, and yeast infections.

The term "about," as used herein, when referring to a value or to an amount of mass, weight, time, volume, or percentage is meant to encompass variations of ±20% or ±10%, more preferably ±5%, even more preferably ±1%, and still more preferably ±0.1% from the specified amount, as such variations are appropriate to perform the disclosed method.

The "patient" or "subject" treated in the many embodiments disclosed herein is desirably a human patient, although it is to be understood that the principles of the presently disclosed subject matter indicate that the presently disclosed subject matter is effective with respect to all vertebrate species, including mammals, which are intended to be included in the terms "subject" and "patient." In this context, a mammal is understood to include any mammalian species in which treatment is desirable, particularly agricultural and domestic mammalian species, such as horses, cows, pigs, dogs, and cats.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl oups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, Including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzlmidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, two, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalky" can be used interchangeably with "alkoxyl".

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 5, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e.,

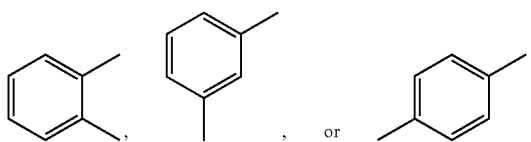

respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a diazeniumdiolate (i.e., NONO).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-NH$_2$ group.

The term "carbonyl" refers to the —(C=O)— group.

The term "carboxyl" refers to the —COOH group and the term "carboxylate" refers to an anion formed from a carboxyl group, i.e., —COO".

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group.

The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to Si(OR)$_4$, wherein R is alkyl. Each alkyl group can be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to the Si—OH group.

II. Nitric Oxide-Releasing Particles

The presently disclosed subject matter provides nitric oxide-releasing particles and their use in biomedical and pharmaceutical applications. In many embodiments, the presently disclosed particles release nitric oxide in a controlled and/or a targeted manner and thereby improve and prolong the biological action and specificity of nitric oxide. In some embodiments, the presently disclosed nitric oxide-releasing particles can be functionalized to provide a new platform for the delivery of nitric oxide to cells and/or tissues in vivo. Thus, the presently disclosed nitric oxide-releasing particles provide a unique scaffold for nitric oxide donor chemistry and nitric oxide release therapy.

Referring now to FIG. 1, the presently disclosed particles P can, in some embodiments, be described in terms of comprising a core CR, a nitric oxide donor NO, an "interior" or "interior region" IR which comprises the area inside the exterior, and an "exterior" or an "exterior region" ER. As described more fully hereinbelow, interior IR can also contain organic linker OLK that can optionally include a labile portion or group LP.

Exterior or exterior region ER can be defined as the outermost chemical functionality of particle P. In some embodiments, exterior ER contains a moiety or moieties that can control the nitric oxide release kinetics of particle P, alter the biocompatibility of particle P, manipulate the solutility of particle P, provide for the targeted delivery of particle P to a desired location (e.g., a specific cell, tissue or organ) prior to NO-release, provide for imaging or tracking of particle P, or supply an additional therapeutic agent (i.e., in addition to the NO). Such an exterior ER can be said to control a function of NO-releasing particle P, or be "functionalized." In some embodiments, the chemical groups of exterior region ER can control more than one of the functions of NO-releasing particle P, and exterior ER can be described as "multi-functional." In some embodiments, chemical moieties or other structural characteristics throughout particle P (e.g., in core CR or interior IR) can be used to control a factor or factors related to NO-release kinetics, particle solubility, targeting, imaging, tracking, additional therapeutic ability, or biocompatibility, and entire particle P can be described as multifunctional.

As shown in FIG. 1, in some embodiments, interior region. IR comprises organic linker LK. As used herein, the term "organic linker" or "linker" refers to an organic tether bridging the gap between the particle core and the particle exterior. In some embodiments, as described more fully hereinbelow, organic linker LK can comprise labile group LP. In some embodiments, organic linker LK can be somewhat or substantially hydrophobic. In some embodiments, linker LK is branched. In some embodiments, linker LK is covalently attached to one or more of the other elements of particle P, such as core CR, exterior ER or NO donor N.

The particles of the presently disclosed subject matter can be any shape. Thus, the particles can be spherical, elliptical, or amorphous. The size and shape of the particles is, at least in part, determined by the nature (i.e., the chemical composition) or the method of synthesis of the core. In some embodiments, the size of the particle can be manipulated to affect the amount or rate of NO-release.

In some embodiments, the NO-releasing particles are nanoparticles. In some embodiments, the term "nanoparticle" Is meant to refer to a particle having a diameter of between about 0.5 rim and about 1000 nm. In some embodiments, the nanoparticles have a diameter of between about 1 nm and about 500 nm. In some embodiments, the nanoparticles can have a diameter of between about 2 nm and about 200 nm. In some embodiments, the particles have a diameter of between about 1 nm and about 50 nm.

In some embodiments, the particles are larger than 1000 nm. Thus, in some embodiments, the particle is a microparticle. In some embodiments, the particles have a diameter of up to about 25 microns. In some embodiments, the particle can have a diameter of up to about 100 microns.

The nitric oxide donor can be part of the core, the interior, or the exterior of the particle. The NO donor can be encapsulated in one of the core, the interior, or the exterior. The NO donor can be associated with a particular region of the particle via non-covalent interactions such as Van der Waals interactions, electrostatic interactions (such as interactions between dipoles or between charged groups), hydrogen bonding, or combinations thereof. Further, the NO donor can be covalently bonded to one of the core, the interior, or the exterior. The percent composition of the NO releasing moiety can be varied via covalent attachment or via encapsulation to impart an effective payload of nitric oxide for the desired therapeutic or other result.

The NO releasing moiety or NO donor is engineered in such a fashion as not to disrupt the other particle descriptors while storing its quantity of NO until the appropriate targeting of the particle has occurred. The NO release can be initiated thermally or via any of the degradation strategies for the labile portion of the linker as described herein below. Thus the NO donor can be any moiety capable of releasing NO, including N-diazeniumdiolates, nitrosamines, hydroxyl nitrosamines, nitrosothiols, hydroxylamines, hydroxyureas, metal complexes, organic nitrites and organic nitrates. See, Wang, P. G., et al., *Nitric Oxide Donors: For Pharmaceutical and Biological Applications*; Wliey-VCH: Weinheim, Germany, 2005; and Wang. P. G., et al., *Chem. Rev.*, 102, 1091-1134 (2002).

In some embodiments, the NO donor is a N-diazeniumdiolate (i.e., a 1-amino-substituted deazen-1-lum-1,2-diolate), N-Diazeniumdiolates are particularly attractive as NO donors due to their ability to generate NO spontaneously under biological conditions. See Hrabie, J. A. and Keefer, L. K., *Chem. Rev.*, 102, 1135-1154 (2002); and Napoli, C. and Ianarro, L. J., *Annu. Rev. Pharmacol. Toxicol.*, 43, 97-123 (2003). As shown in Scheme 1, below, several N-diazeniumdiolate compounds have been synthesized using a range of nucleophilic residues that encompass primary and secondary amines, polyamines, and secondary amino acids, See Hrabie, J. A., and Keefer L. K., *Chem. Rev.*, 102, 1135-1154 (2002). In the formation of the N-diazeniumdiolate, one equivalent of amine reacts with two equivalents of nitric oxide under elevated pressure. A base(e.g., an alkoxide like methoxide) removes a proton from the amine nitrogen to create the anionic, stabilized [N(O)NO] group. While stable under ambient conditions, N-diazeniumdiolates decompose spontaneously in aqueous media to generate NO at rates dependent upon pH, temperature, and/or the structure of the amine moiety. For example, N-diazeniumdiolate-modified proline (PROLI/NO), 2-(dimethylamino)-ethylputreamlne (DMAEP/NO), N,N-dimethylhexanediamine (DMHD/NO), and diethylenetriamine (DETA/NO) have been developed as small molecule NO donors with diverse NO release half-lives ranging from 2 seconds to 20 hours at pH 7.4 and 37° C. See Hrabie, J. A., and Keefer, L. K., *Chem. Rev.*, 102, 1135-1154 (2002); and Keefer, L. K., *Annu, Rev. Pharmacol. Toxicol* 43, 585-607 (2003).

Scheme 1. Synthesis and NO-release from N-diazeniumdlolates.

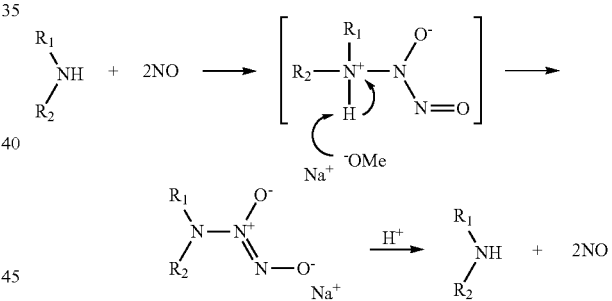

As described in more detail immediately hereinbelow, in some embodiments, the "core" of the presently disclosed particles comprises a material selected from the group including, but not limited to: (a) a metallic cluster; (b) a dendritic network; and (c) a co-condensed silica (i.e. siloxane-bonded) network possessing variable silane functionality.

II.A. Cores Comprising Metallic Clusters

In some embodiments, the core of the presently disclosed particles comprises a metallic cluster. The metallic clusters can comprise any metallic complex that can be passivated or "protected" for further functionalization. For example, protected metallic complexes can be formed, in some embodiments, by being coated with organic polymers or silica. Metallic complexes can also be protected with monolayers of organic molecules wherein the organic molecules contain a functionality that coordinates to or otherwise forms a covalent or non-covalent bond with metal atoms at the surface of the metallic complex.

The metallic complexes can be metals, metal alloys, metal salts, or metal oxides. In some embodiments, the metallic complex comprises gold, sliver, platinum, iron oxide (i.e., FeO, $Fe_2O_3$, or $Fe_3O_4$), or semiconductor particles such as CdSe, and the like. In some embodiments the iron oxide is magnetite (i.e., $Fe_3O_4$). In some embodiments, the core Is a monolayer protected gold cluster, which can be formed via a variety of methods known in the art, including the Brust method and the Schufz-Dobrick method.

Figure 2:
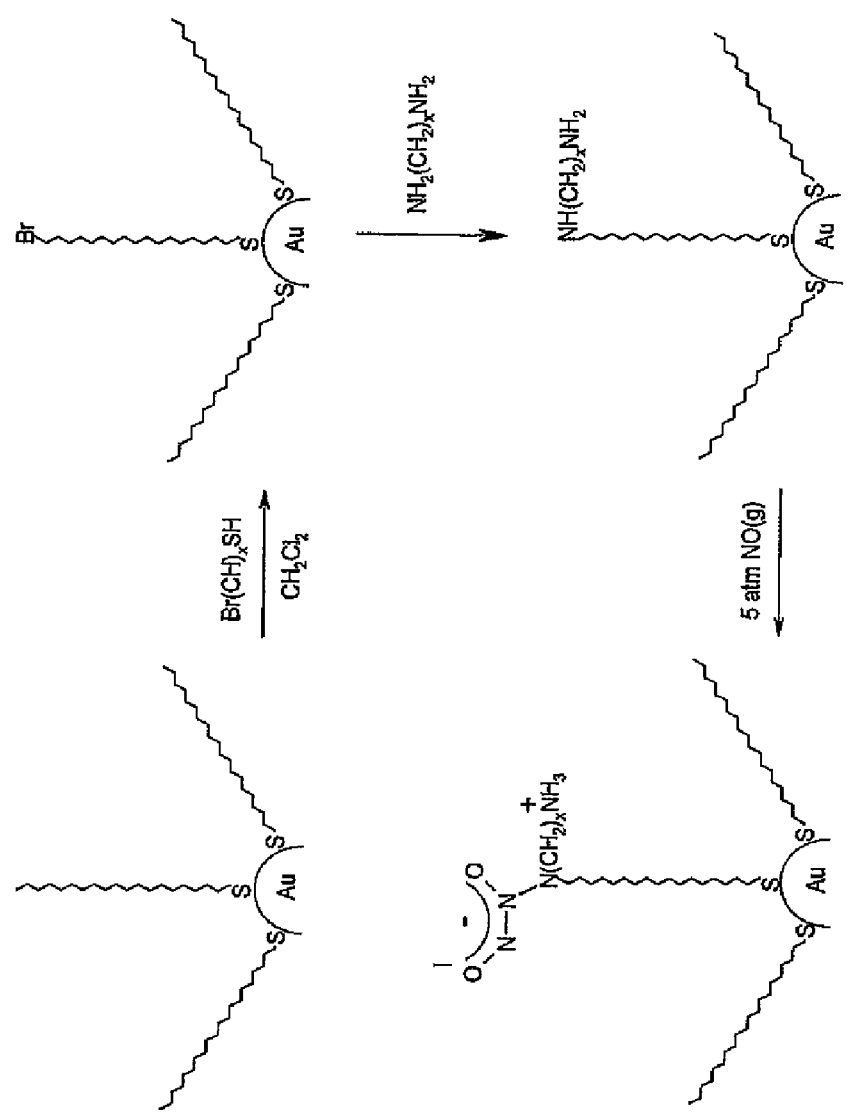
FIG. 2 is a synthesis scheme for preparing the presently disclosed NO-releasing monolayer protected cluster (MPC) gold nanoparticles.

Monolayer protected cluster (MPC) gold nanoparticles or MPCs, see Brust, M., *J. Chem. Soc., Chem: Comm.*, 801-602 (1994), have received much attention due to their unique size (1 nm to 5 nm), stability, and highly functional design. See Feldheim, D. L. and Foss, C. A., eds, *Metal Nanoparticles—Synthesis Characterization, and Applications*, Marcel Dekker, Inc: New York, p. 360 (2000). As shown in FIG. 2, the exterior of MPCs can be altered by place exchanging in other thiols containing desired functional groups. See Hostetler, M. I., et al., Langmuir, 15, 3782-3789 (1999).

Further functionalization of the particles with receptor molecules to enable specific antibody-antigen or ligand-receptor interactions allows for the targeting of specific tissues or cells. The size and stability of NO-releasing MPC gold nanoparticles provides for a range of biomedical and pharmaceutical applications including in vivo sensor design and topical creams to enhance wound healing and/or dilate blood vessels below the skin.

III.B. Cores Comprising Dendrimers

Dendrimers provide a unique scaffold for nitric oxide donor chemistry whereby the multivalent dendritic exterior can be functionalized to suit any number of materials science or biomedical applications.

Dendrimers are polymers with densely branched structures having a large number of reactive groups. A dendritic polymer includes several layers or generations of repeating units which all contain one or more branch points. Dendrimers, including hyperbranched dendritic polymers, are prepared by condensation reactions of monomeric units having at least two reactive groups. Dendrimers generally consist of terminal surface groups, interior branch junctures having branching functionalities greater than or equal to two, and divalent connectors that covalently connect neighboring branching junctures.

Dendrimers can be prepared by convergent or divergent synthesis. Divergent synthesis of dendrimers involves a molecular growth process that occurs through a consecutive series of geometrically progressive step-wise additions of branches upon branches in a radially outward direction to produce an ordered arrangement. Thus, each dendritic macromolecule can be said to include a core cell, one or more layers of internal cells, and an outer layer of surface cells, wherein each of the cells includes a single branch juncture. The cells can be the same or different in chemical structure and branching functionality. The surface branch cells may contain either chemically reactive or passive functional groups, Chemically reactive surface groups can be used for further extension of dendritic growth or for modification of dendritic molecular surfaces. The chemically passive groups may be used to physically modified dendritic surfaces, such as to adjust the ratio of hydrophobic to hydrophilic terminals, and/or to improve the solubility of the dendritic polymer for a particular solvent.

The convergent synthesis of dendrimers involves a growth process that begins from what will become the surface of the dendron or dendrimer and progresses radially toward a focal point or core. The dendritic polymers may be ideal or non-ideal, i.e., imperfect or defective. Imperfections are normally a consequence of either incomplete chemical reactions, or unavoidable competing side reactions. In practice, real dendritic polymers are generally non-ideal, i.e., contain certain amounts of structural imperfections.

Hyperbranched dendritic networks refer to a class of dendritic polymers that contain high levels of non-ideal irregular branching. Specifically, hyperbranched polymers contain a relatively high number of irregular branching areas in which not every repeat unit contains a branch juncture. The preparation and characterization of dendrimers, dendrons, random hyperbranched polymers, controlled hyperbranched polymers, and dendrigrafts is well known. Examples of dendrimers and dendrons, and methods of synthesizing the same are set forth in U.S. Pat. Nos. 4,507,466; 4,558,120; 4,568,737; 4,587,329; 4,631,337; 4,694,064; 4,713,975; 4,737,550; 4,871,779 and 4,857,599. Examples of hyperbranched polymers and methods of preparing the same are set forth, for example in U.S. Pat. No. 5,418,301.

Suitable dendrimers for use as core scaffolds of the presently disclosed particles include polypropylenimine dendrimer; polyamidoamine (PAMAM) dendrimer; polyaryl ether dendrimer; polylysine dendrimer; polyester dendrimer; polyamide dendrimer; dendritic polyglycerol; and triazine dendrimers, In some embodiments, the presently disclosed subject matter provides a series of polypropylenimine (PPI) dendrimer conjugates, which comprise exterior secondary amines. The secondary amine-containing PPI dendrimers can be synthesized from PPI dendrimers having exterior primary amines by acylating the primary amines and reducing the carbonyl of the resulting amide groups to form secondary amines. Alternatively, the primary amines can be acylated with groups already containing a secondary amine. Far example, the exterior primary amines of a PPI dendrimer can be acylated with praline.

The secondary amine functional group of the dendrimers is converted in high yields to a nitric oxide donor in the presence of a strong base and gaseous nitric oxide. As provided herein, the dendrimer size and surface functionality effect both the percent conversion of the secondary amine to the nitric oxide donor and the nitric oxide release kinetics.

II.C. Cores Comprising Co-Condensed Silica Networks

Inorganic-organic hybrid silica nanoparticles, functionalized ceramic composites prepared from silicon dioxide, have been explored for applications spanning separation, biological labeling, diagnostics, and carrier systems for the controlled delivery of drugs, genes, and proteins. See Lai, C.-Y., et al., *J. Am. Chem. Soc.*, 125, 4451-4459 (2003); Munoz. B., et al., *Chem. Mater.*, 15, 500-503 (2003); Roy, I., et al., *Proc. Natl. Acad. Sci, USA.*, 102, 279-284 (2005); Trewyn, B. G., et al., *Nano. Lett.*, 4, 2139-2143 (2004); and Yoshitake, H., *New. J. Chem.*, 29, 1107-1117 (2005). The drug delivery potential of silica particles has received much attention because of their physical and chemical versatility and non-toxic nature. See Sayari, A., and Hambudi, S., *Chem. Mater.*, 13, 3151-3168 (2001); and Stein, A., et al., *Adv. Mater.*, 12, 1403-1419 (2000). The synthesis of inorganic-organic hybrid silica modified with reactive organic groups (e.g., amines, carboxylates, thiols, olefins, halides, and epoxides) capable of further functionalization with deliverable molecules has been reported, See Savari, A., and Hamoudi, S., *Chem. Mater.*, 13, 3151-3168 (2001); and Stein, A., et al., *Adv. Mater.*, 12, 1403-1419 (2000), Indeed, numerous silane-coupling agents with the aforementioned functional moieties have been developed for surface grafting (via free silanol groups) of drugs and other therapeutics. See Anwander, R., et al., *Stud. Surf. Sci. Catal.*, 117, 135-142 (1998).

In one example, Meyerhoff and coworkers have reported grafting amine-functionalized silylation reagents onto the surface of fumed silica (amorphous particles, 0.2-0.3 gm in diameter). See Zhane, H., et al., *J. Am. Chem. Soc.*, 125, 5015-5024 (2003). The surface bound amines were then converted to N-diazeniumdiolate NO donors. The NO-releasing silica was employed as filler for preparing silicone rubber polymer coatings with improved hemocompatibility.

The usefulness of such scaffolds as therapeutic NO delivery systems remains hindered for multiple reasons. Since the modification is restricted to the outer surface of the particles, the NO storage capability is inherently limited, control over the NO release kinetics is problematic, and NO donor moieties are more susceptible to contamination from reactive species (e.g., radicals, peroxides, and transition metals) in biological fluids. See Keefer, L. K., *Anna, Rev. Pharmacot. Toxicol.*, 43, 585-607 (2003); Naooli. C., and Ionarro, L. J., *Annu. Rev. Pharmacol. Toxicol.*, 43, 97-123 (2003); and Zhou, Z., and Meyerhoff, M. E., *Biomacromolecules*, 6, 780-789 (2005).

Figure 3:
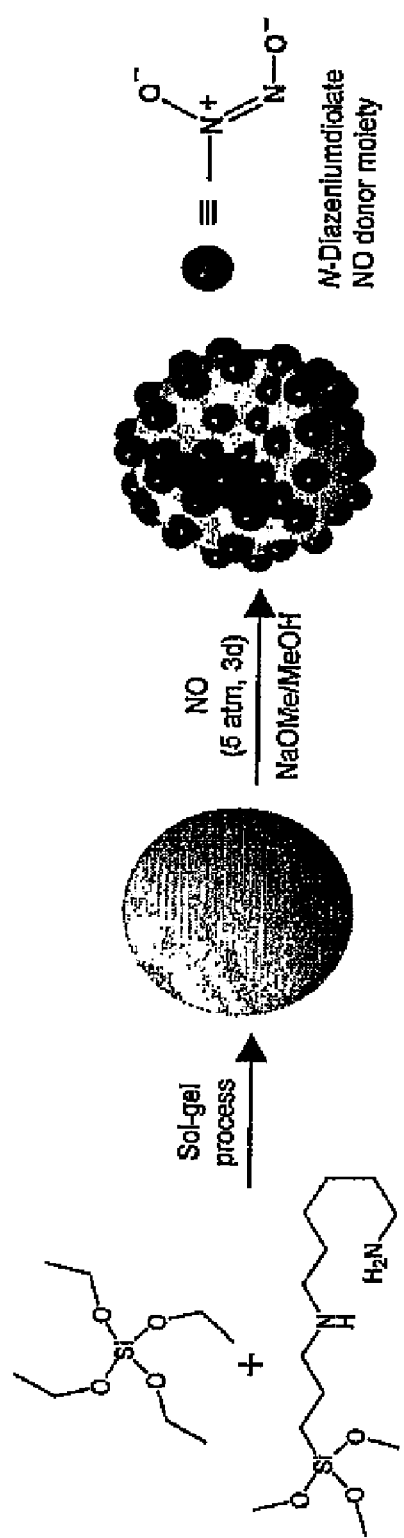
FIG. 3 is a schematic representation of the synthesis of NO-releasing particles via the co-condensation of silica networks from mixtures of alkoxysilanes and aminoalkoxysilanes followed by treatment of the co-condensed silica network with NO gas.

The particles of the presently described subject matter can comprise co-condensed silica networks that provide NO-delivery systems of increased NO storage capacity and an enhanced ability to control NO release kinetics. In some embodiments, the presently disclosed NO-releasing silica-based particles are prepared via a "one-pot" synthetic strategy. See Stein, A., et al., *Adv. Mater.* 12, 1403-1419 (2000); Hatton, B. et al., *Acc. Chem. Res.*, 38, 305-312 (2005), Lin, H.-P., and Mou, C,-Y., *Acc. Chem. Res.*, 35, 927-935 (2002). Thus, as shown in FIG. 3, the inorganic-organic hybrid silica particles are prepared via a sol-gel process involving the co-condensation of tetraethyl orthosilicate (TEOS) or another alkoxysilane with di- or tri-aminoalkoxysilaries. The "sol-gel" process involves two types of chemical reactions; a hydrolysis reaction in which an alkoxy group of an alkoxysilane is hydrolyzed to a silanol (i.e., a hydroxy group attached to the Si atom), followed by a condensation reaction wherein two silanols or a silanol and an alkoxysilane react to form a siloxane bond (i.e., Si—O—Si).

The advantage of a "one-pot" approach is that the N-diazeniumdiolate NO donor precursors (i.e., the amino groups of the di- and tri-aminoalkoxysilane) can be distributed uniformly throughout the entire particle as opposed to only at the surface as is the case for amine-modified silica particles formed via surface grafting methods. See FIGS. 4A and 4B. Indeed, the direct "one-pot" synthesis provides better structural stability and more straightforward control over the amount of organoalkoxysilanes incorporated in the silica structure: See Stein, A., et al., *Adv. Mater.*, 12, 1403-1419 (2000); and Lim, M, H., and Stein, A., *Chem, Mater.*, 11, 3285-3295 (1999). Further, additional silanes containing a variety of other functional groups can also be co-condensed into the structure, thereby affecting the size, the solubility, or the porosity of the particles.

Thus, in some embodiments, the nanoparticle core comprises a co-condensed silane network formed from the co-condensation of an alkoxysilane and an aminoalkoxysilane. In some embodiments, the aminoalkoxysilane is further functionalized after the co-condensation by treatment with nitric oxide so that the amines are transformed into N-diazeniumdiolates. See FIG. 5A. In some embodiments, the aminoalkoxysilane is "pretreated" or "precharged" with nitric oxide prior to co-condensation with the alkoxysilane. See FIG. 5B. The "pre-charging" method can be used to create a co-condensed silica particle more densely functionalized with NO-donors.

In some embodiments, the alkoxysilane is a tetraalkoxysilane having the formula $Si(OR)_4$, wherein R is an alkyl group. The R groups can be the same or different. In some embodiments the tetraalkoxysilane is selected tetra methyl orthosilicate (TMOS) or tetraethyl orthosilicate (TEOS).

Figure 6:
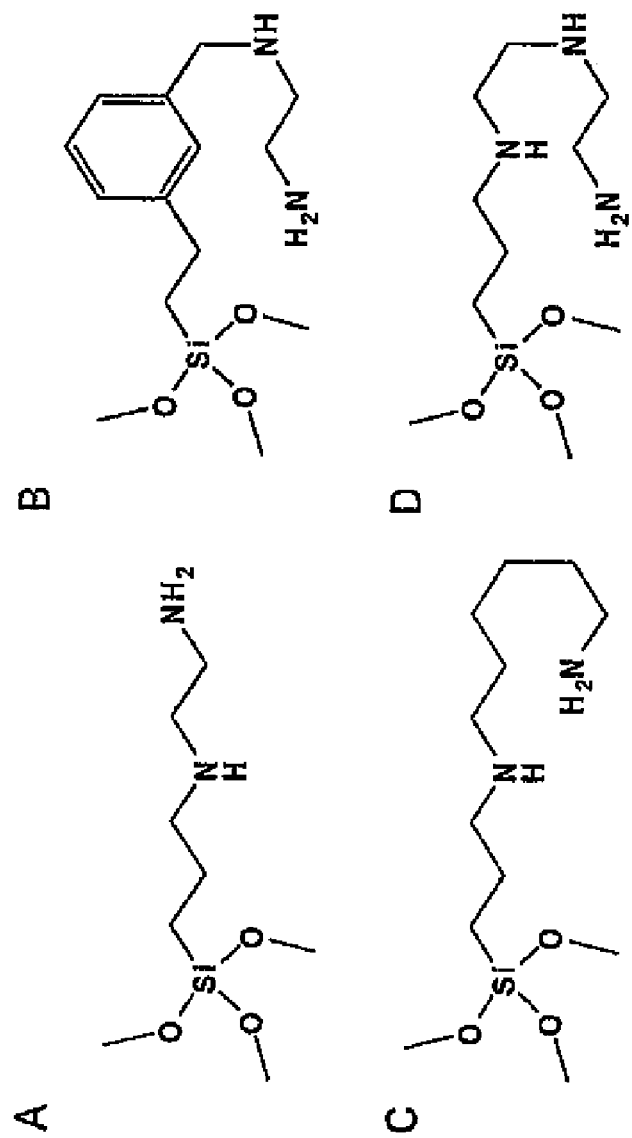
FIG. 6A is the structure of N-(2-aminoethyl)-3-aminopropyltrimethoxysilane (AEAP3).
FIG. 6B is the structure of (aminoethylaminomethyl)phenethyltrimethoxysilane (AEMP3).
FIG. 6C is the structure of N-(6-aminohexypaminopropyl)trimethoxysilane (AHAP3).
FIG. 6D is the structure of N-[3-(trimethoxysilyl)propyl] diethylenetriarnine (DET3).

In some embodiments, the aminoalkoxysilane has the formula:

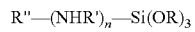

wherein R is alkyl, R' is alkylene, branched alkylene, or aralkylene, n is 1 or 2, and R" is selected from the group consisting of alkyl, cycloalkyl, aryl, and alkylamine. In some embodiments, the aminoalkoxysilane can be selected from N-(6-aminohexyl)aminopropyltrimethoxysilane (AHAP3); N-(6-aminoethyl)aminopopyltrimethoxysilane; (3-trimethoxysilylpropyl)diethylenetriamine (DET3); (aminoethylaminomethyl)phenethyltrimethoxysilane (AEMP3); [3-(rnethylamino)propyltrimethoxysilane; N-butylaminopropyltrimethoxysilane; N-ethylaminoisobutyltrimethoxysilane; N-phenylaminopropyltrimethoxysilane; and N-cyclohexylaminopropyltrimethoxysilane. The structures of representative suitable aminoalkoxysilanes are shown in FIG. 6.

In some embodiments, the aminoalkoxysilane has the formula:

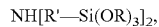

wherein R is alkyl and R' is alkylene. Thus, in some embodiments the aminoalkoxysilane can be selected from bis-[3-(trimethoxysilyl)propyl]amine and bis-[(3-trimethoxysilyl)propyl]ethylenediamine.

In some embodiments, as described hereinabove, the aminoalkoxysliane is precharged for NO-release and the amino group is substituted by a diazeniumdiolate. Therefore, in some embodiments, the aminoalkoxysilane has the formula:

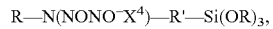

wherein R is alkyl, R' is alkylene or aralkylene, R" is alkyl or alkylamine, and $X^+$ is a cation selected from the group consisting of $Na^+$, $K^+$, and $Li^+$.

The composition of the silica network, (e.g., amount or the chemical composition of the aminoalkoxysilane) and the nitric oxide charging conditions (e.g., the solvent and base) can be varied to optimize the amount and duration of nitric oxide release. Thus, in some embodiments, the composition of the presently disclosed silica particles can be modified to regulate the half-life of NO release from silica particles.

In some embodiments, the hydrophobicity of nitric oxide-releasing silica particles can be controlled by co-condensing silane precursors having a variety of functional groups into the co-condensed silica network. In some embodiments, the other silane precursors are selected from the group including but not limited to alkylsilanes, positively charged silanes, negatively charged silanes, and fluorinated silanes. in some embodiments the other silane precursors can be selected from (heptadecafluoro-1,1,2,2-tetrahydrodecyl)triethoxysilane; (3,3,3-trifluoropropyl)trimethoxysilane; (perfluoroalkyl)ethyltriethoxysilane; N—N-didecyl-N-methyl-N-(3-trimethoxysilyl)ammonium chloride; octadecyldimethyl-(3-trimethoxysilylpropyl)ammonium chloride; 3-trihydroxysllylpropylmethyl phosphonate, sodium salt; carboxylethylsilanetriol, sodium salt; methyltrimethoxysilane; butyltrimethoxysilane; butyltriethoxysilane; propyltrimethoxysilane; and octadecyltrimethoxysilane.

In some embodiments, the co-condensed silica network comprises (i.e., is formed from the condensation of a solution containing) between about 10 mol % to about 99 mol % of tetraalkoxysilane; about 1 mol % to about 90 mol % of aminoalkoxysilane; about 0 mol % to about 20 mol % of fluorinated silane; about 0 mol % to about 20 mol % of cationic or anionic silane; and about 0 mol % to about 20 mol % of alkylsilane.

In some embodiments, the porosity and the NO-release capability of the silica network can be controlled by co-condensing silanes in the presence of a templating component. Such templating components can include surfactants and micelles. After condensation of the silica network, the templating component can be removed, leaving pores in the silica. The incorporation of pores in a NO-releasing silica particle can increase the surface area available for NO donor loading or can serve to increase the rate of NO release by increasing the accessibility of water to the NO donors.

Figure 7:
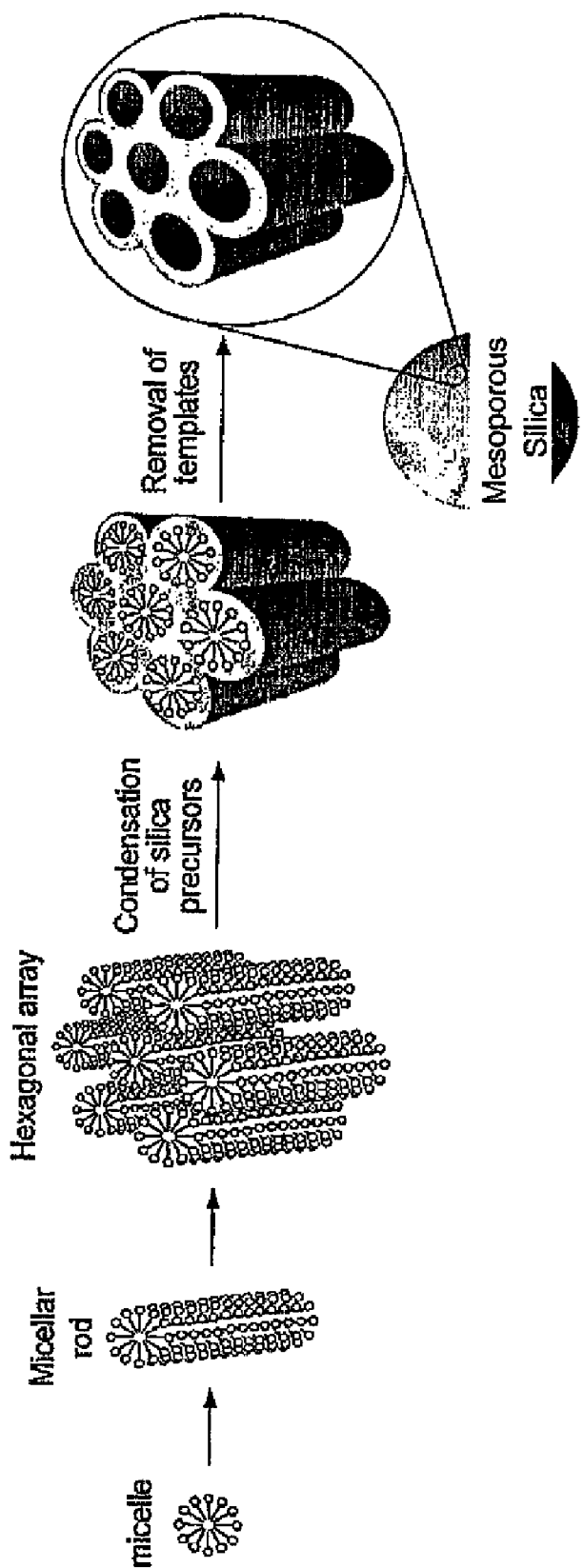
FIG. 7 is a schematic representation of the templated synthesis of mesoporous co-condensed silica networks using micelles as templating agents to direct pore formation.

For example, FIG. 7 shows the schematic representation of the synthesis of a mesoporous silica network using micelles as pore templates. As shown in FIG. 7, micelles can self-associate in a controlled solvent environment to form an ordered three-dimensional structure, such as a micellular rod, or an even more highly structured array of multiple rods. Solutions containing mixtures of silanes can be introduced into the micelle solution and condensed, surrounding, but not penetrating, the micelle rods. Following condensation of the silane mixture, the micelles can be removed from the condensed silica via solvent extraction, leaving behind pores in the silica.

In some embodiments, the presently disclosed subject matter provides functionalized silicas, silicas that can be further elaborated through a variety of chemical coupling reactions known in the art. In some embodiments, the functionalized silica is an amino-modified silica. In some embodiments, the functionalized silica is an epoxy-modified silica.

In some embodiments, the presently disclosed silica chemistry is combined with hydroxylamine chemistry. In some embodiments, the presently disclosed silica chemistry is combined with hydroxyurea chemistry.

III. Triggered Release of Nitric Oxide from Nitric Oxide-Releasing Particles

Controlled and/or targeted delivery techniques typically enhance the efficacy and/or safety of an active agent by controlling the rate and/or location of the release of the active agent. In some embodiments, the release of nitric oxide from the presently disclosed nitric oxide-releasing particles can be selectively turned on or turned off (i.e., triggered), as desired.

Figure 8:
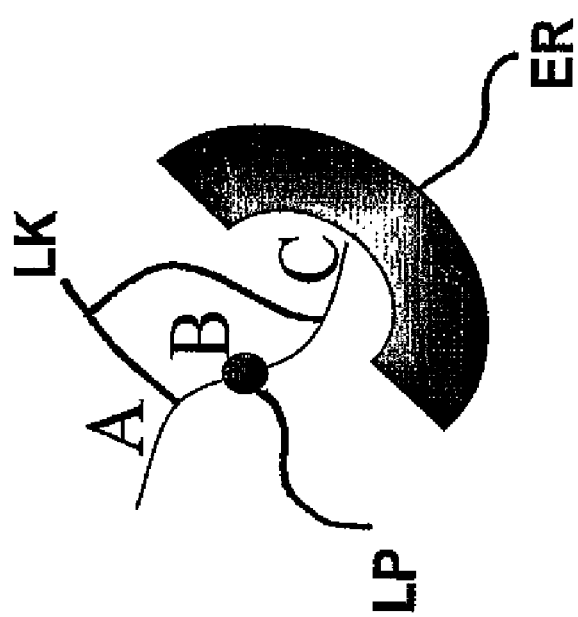
FIG. 8 is a schematic representation of a portion of the NO-releasing particle as previously described for FIG. 1, further showing that the labile portion LP of the linker LK can be positioned at varying distances from the particle exterior EP. Position A is farthest away from the exterior, position B is located in the middle of the linker, and position C is closest to the exterior of the particle.

In some embodiments, the organic linker comprises a "labile" portion. In such embodiments, the triggered degradation of the linker can affect the mechanism, quantity, rate, and duration of NO release. Referring to FIGS. 1 and 8, labile portion LP of linker LK can be placed at variable positions A, B, or C, in relation to exterior ER such that the position of linker LK further affects the mechanism, quantity, rate, and duration of NO release. For example, in some embodiments, position A of FIG. 8 can be adjacent to NO donor NO in interior IR of NO-releasing particle P of FIG. 1; position B can be centrally located between NO donor NO and exterior ER; and position C can be located in close proximity to exterior ER. Thus, in some embodiments, a labile group LP at position C can be degraded more quickly by environmental conditions to which particle P is subjected, in turn exposing NO donor NO located in interior IR of particle P to the same environmental conditions sooner. Labile groups LP located more deeply in particle interior IR at positions A or B can, in some embodiments, provide for prolonged or delayed release kinetics.

In some embodiments, the "labile" portion of the linker can be degraded by exposure to a stimulus, e.g., via a triggering mechanism. In some embodiments, the stimulus, or triggering mechanism, is selected from the group including but not limited to pH, light, and enzymatic action.

In embodiments wherein decomposition of the labile portion of the linker is triggered by pH, the linker comprises functionalities, such as esters, hydrazones, acetals, and/or other organic functional groups, which are responsive to changes in pH. Accordingly, in some embodiments, the linker decomposes in a predetermined pH range. More particularly, in some embodiments, the linkers are designed to utilize the pH of increased acidity inside an endosome, the cellular structure resulting from internalization of a macromolecule via endocytosis.

In some embodiments, decomposition of the linker is triggered by exposure to light. In such embodiments, the "labile" portion is subject to photocleavage, such that a photolabile moiety is built into the variable linker that results in degradation of the linker structure upon exposure to light.

In some embodiments, an enzyme substrate is incorporated into the linker to impart specificity of the system to a desired enzyme environment of interest, followed by degradation of the linker via the enzymatic pathway of interest.

Thus, in some embodiments, the lability of the linker can be used as a strategy to control the mechanism, quantity, rate, and duration of NO release from the NO-releasing moiety. Labile linkers include esters, hydrozones, acetals, thiopropionates, photolabile moieties and amino acid sequences subject to enzyme degradation.

In some embodiments, the organic linker is a hydrophobic linker. A hydrophobic linker can be chosen as an approach for protecting the NO donor, for example the diazeniumdiolate, and/or the labile linker from contact with water or protons when the particle is placed in an aqueous environment. The length and exact chemical composition of a hydrophobic linker can, therefore, be used to control the NO-release kinetics. The term hydrophobic can include groups that are strongly hydrophobic (i.e., have a very low dielectric constant) or are only somewhat hydrophobic (i.e., would allow water to slowly penetrate into the interior of the particle).

Alternatively, the organic linker can be amphiphilic, containing both hydrophobic and hydrophilic groups. Such a linker might provide channels in the interior of the particle, thereby enhancing solvent access to a labile linker or a NO-donor.

NO release can also be controlled through encapsulation of the NO-donor in a carrier system, such as a nano- or microparticle, a cell, a cell ghost, a lipoprotein, a liposome, a micelle, a microbubble, a microsphere, or a particle made at least partially of insoluble or biodegradable natural or synthetic polymers. In such a system, the NO can be gradually released as the carrier degrades in the body. The rate of degradation typically varies responsively to conditions in the subject, such as temperature, pH level, and enzymatic activity. Thus, through the use of such delivery techniques, a sustained release of the therapeutic agent can be maintained for long periods of time.

IV. Additional Functionalization of the Nitric Oxide Releasing Particles

As provided herein, the exterior, interior and/or core of the presently disclosed particles can be functionalized to impart biocompatibility, alter pharmacokinetic behavior, convey targeting functionality, add additional therapeutic components, and impart imaging capability, relevant to the delivery and study of the NO as a therapeutic. In some embodiments, the exterior of the particle can be functionalized with one or more chemical or biomolecular moieties.

The exterior can be of uniform or variable chemical composition. In some embodiments, the functionalization of the exterior of the particle can comprise the addition of a layer or coating surrounding the interior of the particle. In some embodiments, the functionalization can involve the addition of one or more pendant groups to individual points on the periphery of the particle. Thus, the exterior can comprise one or more pendant antigens for particle targeting as discussed more fully herein below. The exterior can also comprise individual chemical moieties that affect solubility, such as hydroxy groups, thiols, methyl-terminated alkyl chains, sulfonates, phosphates, carboxylates, and cationic or quaternary amines. Further, the exterior can comprise a polymeric layer, for example a hydrophilic polymer to impart improved aqueous solutility or a known biocompatible polymer. The polymeric layer can be a biodegradable polymer, which can protect the NO donor from water for a period of time when used either in vivo or in vitro. Such a polymer coating can thereby affect the NO-release kinetics by allowing for continued NO-release over time as the polymer coating degrades. Suitable polymers for functionalizing the exterior of the presently described particles include (poly)ethyleneoxide, (poly)urethanes, N-(2-hydroxypropyl)methacrylamide copolymer, and lactide/glycolide copolymers (e.g. PLGA).

IV.A. Nitric Oxide Releasing Particles for Targeted Delivery of Nitric Oxide

In some embodiments, additional functionalization of the particle enables targeting of specific cells, tissues, or organs. Thus, in some embodiments, the presently disclosed nitric oxide-releasing particles can be further modified by attaching selective recognition agents to the surface or exterior thereof. Such selective recognition agents include, but are not limited to small molecule ligands; biomolecules, such as antibodies and antibody fragments; and other agents such as cytokines, hormones, carbohydrates, sugars, vitamins, and peptides.

A specific targeting moiety is not required in all cases. In some embodiments, the site specific targeting can also include a more passive approach, such as the enhanced permeability and retention effect (EPR) associated with tumor vasculature. Site specific targeting can also be accomplished by the used of NO-release particles containing linkers that trigger release of the nitric oxide only upon contact with enzymes specific to a disease state or to a particular organ or tissue. Finally, targeting can be accomplished via localized delivery of the particles, for example, topically directly to a wound, or through injection directly to a tumor site.

Generally, when a particle targets cells through a cell surface moiety it is taken into the cell through receptor-mediated endocytosis. Any moiety known to be located on the surface of target cells (e.g. tumor cells) finds use with the presently disclosed particles. For example, an antibody directed against such a cell surface moiety can be used. Alternatively, the targeting moiety can be a ligand directed to a receptor present on the cell surface or vice versa.

In particle embodiments using a specific targeting moiety (i.e., a particle-associated moiety designed to direct the particle to a specific cell, tissue or organ), the targeting moiety is optionally associated with the exterior of the particle. The targeting moiety can be conjugated, directly to the exterior via any useful reactive group on the exterior, such as, for example, an amine, an alcohol, a carboxylate, an isocyanate, a phosphate, a thiol, a halide, or an epoxide. For example, a targeting moiety containing or derivatized to contain an amine that is not necessary for the recognition of the moiety with the targeted cell can be coupled directly to a carboxylate present on the particle exterior using carbodilmide chemistry. The targeting moiety can also be linked to a reactive group on the exterior of the particle through a short bi-functional linker, such as N-succinimidyl-3-(2-pyridyldithio)propionate (SPDP, commercially available from Pierce Chemical Company, Rockford, Ill., United States of America). Alternatively, a longer bifunctional linker can be used, such a polyethylene glycol (PEG)-based bifunctional linker commercially available from EMD Biosciences, Inc. (La Jolla, Calif., United States of America) or Shearwater Polymers (Huntsville, Ala., United States of America).

Targeting moieties for use in targeting cancer cells can be designed around tumor specific antigens including, but not limited to, carcinoembryonic antigen, prostate specific antigen, tyrosinase, ras, a sialyl lewis antigen, erb, MACE-1, MAGE-3, BAGE, MN, gp100, gp75, p97, proteinase 3, a mucin, CD81, CID9, CD63; CD53; CD38, CO-029, CA125, GD2, GM2 and O-acetyl GD3, M-TAA, M-fetal or M-urinary find use with the presently disclosed subject matter. Alternatively the targeting moiety can be designed around a tumor suppressor, a cytokine, a chemokine, a tumor specific receptor ligand, a receptor, an inducer of apoptosis, or a differentiating agent. Further, given the importance of the angiogenisis process to the growth of tumors, in some embodiments, the targeting moiety can be developed to target a factor associated with angiogenisis. Thus, the targeting moiety can be designed to interact with known angiogenisis factors such as vascular endothelial growth factor (VEGF). See Brannon-Peppas, L. and Blanchette, J. O., *Advanced Drug Delivery Reviews*, 56, 1649-1659 (2004).

Tumor suppressor proteins provided for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, C0029, TI-1, L6 and SAS. Of course these are merely exemplary tumor suppressors and it is envisioned that the presently disclosed subject matter can be used in conjunction with any other agent that is or becomes known to those of skill in the art as a tumor suppressor.

In some embodiments, targeting is directed to factors expressed by an oncogene. These include, but are not limited to tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bc1-2 and family members, Cytokines that can be targeted by the presently disclosed particles include, but are not limited to, IL-1, IL-2, IL-3, IL-4, IL-5, IL-6, IL-7, IL-8, IL-9, IL-10, ILA 1, IL-12, IL-13, IL-14, IL-15, TNF, GM-CSF, 8-interferon and y-interferon. Chemokines that can be used include, but are not limited to, M1P1a, M1P1b, and RANTES.

Enzymes that can be targeted include, but are not limited to, cytosine deaminase, hypoxanthine-guanine phosphoribosyltransferase, galactose-1-phosphate uridyltransferase, phenylalanine hydroxylase, glucocerbrosidase, sphingomyelinase, a-L-iduronidase, glucose-6-phosphate dehydrogenase, HSV thymidine kinase, and human thymidine kinase.

Receptors and their related ligands that find use in the context of the presently disclosed subject matter include, but are not limited to, the folate receptor, adrenergic receptor, growth hormone receptor, luteinizing hormone receptor, estrogen receptor, epidermal growth factor receptor, fibroblast growth factor receptor, and the like. In some embodiments, the targeting moiety is selected from the group consisting of folic acid, guanidine, transferrin, carbohydrates and sugars. In some embodiments, the targeting moiety is a peptide selected from the group consisting of the amino acid sequence RGD and TAT peptides.

For example, folic acid can be a particularly useful targeting moiety in targeting cancer cells. Cancerous tumor cells have an over-expression of folate receptors on their cellular surface. Folic acid (FA) can be covalently bound to the nanoparticle exterior, with varying percent modification, to impart the FA targeted delivery of the NO releasing nanoparticles. Because of its small size, many folic acid ligands can be attached to the surface of a particle. Wiener has reported that dendrimers with attached folic acid specifically accumulate on the surface and within tumor cells expressing the high-affinity folate receptor (hFR) while control cells lacking hFR showed no significant accumulation of the folate-derivatized dendrimers. See Wiener, E. C. et al., *Invest. Radiol.,* 32 (12), 748-754 (1997). Folic acid can be attached to amines on the exterior of a particle via a carbodiimide coupling reaction.

A larger, yet still relatively small targeting moiety is epidermal growth factor (EGF), a single-chain peptide with 53 amino acid residues. It has been shown that PAMAM dendrimers conjugated to EGF with the linker SPDP bind to the cell surface of human glioma cells and are endocytosed, accumulating in lysosomes. See CapAla, J., et al., *Bioconjugate Chem.,* 7(1), 7-15 (1996). Since EGF receptor density is up to 100 times greater on brain tumor cells compared to normal cells, EGF provides a useful targeting agent for these kinds of tumors. Since the EGF receptor is also overexpressed in breast and colon cancer, EGF can be used as a targeting agent for these cells as well. Similarly, the fibroblast growth factor receptors (FGFR) also bind the relatively small polypeptides (FGF), and many are known to be expressed at high levels in breast tumor cell lines (particularly FGF1, 2 and 4). See Penault-Llorca, F., et al., *Int. J. Cancer,* 61(2), 170-176 (1995).

Hormones and their receptors include, but are not limited to, growth hormone, prolactin, placental lactogen, luteinizing hormone, follicle-stimulating hormone, chorionic gonadotropin, thyroid-stimulating hormone, leptin, adrenocorticotropin (ACTH), angiotensin I, angiotensin II, β-endorphin, β-melanocyte stimulating hormone (β-MSH), cholecystokinin, endothelin I, galanin, gastric inhibitory peptide (GIP), glucagon, insulin, amylin, lipotropins, GLP-1 (7-37) neurophysins, and somatostatin.

The presently disclosed subject matter contemplates that vitamins (both fat soluble and non-fat soluble vitamins) placed in the targeting component of the nanodevice can be used to target cells that have receptors for, or otherwise take up these vitamins. Particularly preferred for this aspect are the fat soluble vitamins, such as vitamin D and its analogues, vitamin E, Vitamin A, and the like or water soluble vitamins such as Vitamin C, and the like.

Antibodies can be generated to allow for the targeting of antigens or immunogens (e.g., tumor, tissue or pathogen specific antigens) on various biological targets (e.g., pathogens, tumor cells, normal tissue). In some embodiments of the presently disclosed subject matter, the targeting moiety is an antibody or an antigen binding fragment of an antibody (e.g., Fab units). Thus, "antibodies" include, but are not limited to polyclonal antibodies, monoclonal antibodies, chimeric antibodies, single chain antibodies, Fab fragments, and an Fab expression library.

One example of a well-studied antigen found on the surface of many cancers (including breast HER2 tumors) is glycoprotein p185, which is exclusively expressed in malignant cells. See Press, M. F., et al., Oncogene 5(7), 953-962 (1990). Recombinant humanized anti-HER2 monoclonal antibodies (rhuMabHER2) are commercially available under the name HERCEPTIN® from Genentech (South San Francisco, Calif., United States of America). Other representative antibodies suitable for use with the presently disclosed subject matter include, but are not limited to, lgC-type antibodies, 60bca and J591, which bind to CD14 and prostate specific membrane antigen (PSMA), see Baker, J. R., Jr., *Biomacromolecules,* 5, 2269-2274 (2004), which is incorporated herein by reference in its entirety, and antibodies F5 and Cl, which bind to ErbB2 growth factor of breast tumor cell line SK—BR-3.

As described hereinabove, the ability of a particle to provide targeted delivery of NO is not limited to embodiments involving pendant targeting agents attached to the particle exterior. Non exterior-associated characteristics of the particle also can be used for targeting. Thus, in some embodiments, the enhanced permeability and retention (EPR) effect is used in targeting. The EPR effect is the selective concentration of macromolecules and small particles in the tumor microenvironment, caused by the hyperpermeable vasculature and poor lymphatic drainage of tumors. To enhance EPR, in some embodiments, the exterior of the particle can be coated with or conjugated to a hydrophilic polymer to enhance the circulation half-life of the particle and to discourage the attachment of plasma proteins to the particle.

In some embodiments, the targeting moiety can be a magnetic moiety, such as magnetite. In some embodiments, the core of the particle comprises magnetite. In some embodiments, the magnetite core is further coated with a shell containing a co-condensed silica network that contains or can be functionalized to contain an NO donor. Once administered to a subject, magnetic particles can be directed to their target, i.e., the site of desired NO-release, through the application of a magnet. Such a magnet can be applied externally (i.e., outside of the patient or subject).

For additional exemplary strategies for targeted drug delivery, in particular, targeted systems for cancer therapy, see Brannon-Peppas, L. and Blanchette, J. O., *Advanced Drug Delivery Reviews,* 56, 1649-1659 (2004) and U.S. Pat. No. 6,471,968, each of which is incorporated herein by reference in its entirety.

IV.B. Imaging of Nitric Oxide Releasing Particles

In some embodiments, the NO-releasing particle can comprise a moiety to aid in the imaging or tracking of the particles either in viva or ex vivo. Tracking of the particles can be useful in determining the efficacy of the nitric oxide release in treating a disease or in assessing the specificity of the targeting of the particle. An imaging or tracking moiety can be associated with any of the core, the interior or the exterior of the particle. In some embodiments, the imaging or tracking moiety is covalently attached to one of the core, the interior or the exterior of the particle. In some embodiments, the tracking agent or moiety is part of the core, for example in particles containing quantum dot cores.

In some embodiments, the tracking of imaging agent is one of a fluorescent molecule, an organic dye, or a radioisotope.

In some embodiments, the imaging agent can be a magnetic resonance imaging (MRI) contrast agent. Thus, in some embodiments, the exterior of the particle will be functionalized to contain a group capable of chelating to a paramagnetic ion, for example diethylenetriaminepentaacetic acid (DTPA), the chelating group of the commonly used MRI agent Gd(III)-diethylenetriaminepentaacetic acid (Gd(III)-DTPA). Other paramagnetic ions that can be useful in this context of the include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof.

IV.C. Additional Therapeutic Agents

In some embodiments, one or more additional therapeutic agents can be used in combination with the NO donor of the presently described particles. Such additional agents can be incorporated into the particles themselves or be part of a formulation comprising the particles or doses as a separate formulation prior to, after, or at the same time as a formulation including the particles. Such additional therapeutic agents include, in particular, anti-cancer therapeutics, anti-microbial agents, pain relievers, anti-inflammatories, vasodilators, and immune-suppressants, as well as any other known therapeutic agent that could enhance the alleviation of the disease or condition being treated.

In embodiments wherein the additional therapeutic agent or agents are incorporated into the NO-releasing particles, the additional therapeutic can be associated with any of the exterior, the interior or the core of the particle. For example, the additional agents can be encapsulated into the core or linkers in the interior portion of the particle. The additional agents can also be covalently attached to the core, the interior or the exterior of the particles. Further, attachment of the additional agent can include a triggered release strategy, wherein the additional agents can be tethered to the particle via a labile linker that releases the agent upon contact with water, an increase in pH, or enzymatic or photolytic cleavage, preferably at the desired site of action (e.g., a tumor cell, etc.).

The choice of additional therapeutic agents to be used in combination with an NO-releasing particle will depend on various factors including, but not limited to, the type of disease, the age, and the general health of the subject, the aggressiveness of disease progression, and the ability of the subject to tolerate the agents that comprise the combination.

A variety of chemical compounds, also described as "antineoplastic" agents or "chemotherapeutic agents" can be used in combination with or incorporated into the presently disclosed NO-releasing particles used in the treatment of cancer. Such chemotherapeutic compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine-β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, can be used as part of the presently disclosed cancer treatments. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, a-amanitine and other fungal amatoxins, cordycepin (3'-deoxyadenosine), dichlororibofuranosyl benzimidazole, rifampicine, streptovaricin, and streptolydigin also can be combined with or incorporated into the particles of the presently disclosed subject matter to provide a suitable cancer treatment.

Thus, current chemotherapeutic agents that can be used as part of or in combination with the presently describe NO-releasing particles include, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chlorambucil, bisulfan, nitrosurea, dactinomycin, duanorubicin, doxorubicin, bleomycin, pilcomycin, tamoxifen, taxol, transplatimun, vinblastin, and methotrexate, and the like.

As used herein, the term "antimicrobial agent" refers to any agent that kills, inhibits the growth of, or prevents the growth of a babteria, fungus, yeast, or virus. Suitable antimicrobial agents that can be incorporated into the presently disclosed NO-releasing particles to aid in the treatment or prevention of a microbial infection, include, but are not limited to, antibiotics such as vancomycin, bleomycin, pentostatin, mitoxantrone, mitomycin, dactinomycin, plicamycin and amikacin. Other antimicrobial agents include antibacterial agents such as 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bamberrnycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefininox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clindamycin phosphate, clomocycline, colistin, cyclacillin, dapsone, demecicycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin and vancomycin. Antimicrobial agents can also include anti-fungals, such as amphotericin B, azaserine, candicidin(s), chlorphenesin, dermostatin(s), filipin, fungichromin, mepartricin, nystatin, oligomycin(s), perimycin A, tubercidin, imidazoles, triazoles, and griesofulvin.

V. Methods of Treatment

Accordingly, in some embodiments, the presently disclosed subject matter provides a method for the delivery of nitric oxide to a subject, which in some embodiments is intended to treat a disease or condition in a subject in need of treatment thereof. In some embodiments, the presently disclosed subject matter provides a method for the targeted delivery of nitric oxide to a specific site in a subject. Such a site can be specific cells, tissues or organs. Thus, the presently disclosed subject matter provides a method for treating cancer, cardiovascular diseases, and microbial infections; for the inhibition of platelet aggregation and platelet adhesion caused by the exposure of blood to a medical device; for treating pathological conditions resulting from abnormal cell proliferation; transplantation rejections, autoimmune, inflammatory, proliferative, hyperproliferative, vascular diseases; for reducing scar tissue or for inhibiting wound contraction, including the prophylactic and/or therapeutic treatment of restenosis by administering the nitric oxide donor optionally in combination with at least one additional therapeutic agent. The presently disclosed subject matter also provides a method for treating inflammation, pain, fever, gastrointestinal disorders, respiratory disorders, sexual dysfunctions, and sexually transmitted diseases.

V.A. Subjects

In some embodiments, the methods of the presently disclosed subject matter can be useful for treatment of a subject, as defined herein. The subject treated in the presently disclosed subject matter in its many embodiments is a human subject, although it is to be understood that the principles of the presently disclosed subject matter indicate that the presently disclosed subject matter is effective with respect to all vertebrate species, including mammals, which are intended to be included in the term "subject". In this context, a mammal is understood to include any mammalian species in which treatment is desirable, particularly agricultural and domestic mammalian species.

Accordingly, the term "subject" as used herein, refers to any invertebrate or vertebrate species. The methods of the presently disclosed subject matter are particularly useful in the treatment of warm-blooded vertebrates. Thus, the presently disclosed subject matter concerns mammals and birds. More particularly, provided is the treatment and/or diagnosis of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they also are of economical importance to humans. Thus, provided is the treatment of livestock, including, but not limited to, domesticated swine (pigs and hogs), ruminants, horses, poultry, and the like.

V.B. Formulations

The presently disclosed therapeutic compositions, in some embodiments, comprise a composition that includes a presently disclosed nitric oxide-releasing nanoparticle and a pharmaceutically acceptable carrier. Suitable compositions include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In some embodiments, the presently disclosed therapeutic compositions comprise an additional therapeutic agent in combination with the nitric oxide-releasing nanoparticles, wherein the additional therapeutic agent has additional desired therapeutic properties or enhances the therapeutic properties of the nitric oxide-releasing nanoparticles. The additional therapeutic agent can be administered in the same or a different therapeutic composition. Thus, the term "in combination" can refer to the administration of active agents in a single composition or in one or more separate compositions.

The compositions used in the presently disclosed methods can take such forms as suspensions, solutions or emulsions in oily or aqueous vehicles, and can contain formulatory agents, such as suspending, stabilizing and/or dispersing agents. Alternatively, the active ingredient can be in powder form for constitution with a suitable vehicle, e.g., sterile pyrogen-free water, before use.

The therapeutic compositions can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic agent can be formulated in combination with hydrochlorothiazide, and as a pH stabilized core having an enteric or delayed release coating which protects the therapeutic agent until it reaches the target organ.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds also can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds also can be formulated in rectal compositions (e.g., suppositories or retention enemas containing conventional suppository bases, such as cocoa butter or other glycerides), creams or lotions, or transdermal patches.

Pharmaceutical formulations also are provided which are suitable for administration as an aerosol by inhalation. These formulations comprise a solution or suspension of a NO-releasing particle described herein. The desired formulation can be placed in a small chamber and nebulized. Nebulization can be accomplished by compressed air or by ultrasonic energy to form a plurality of liquid droplets or solid particles comprising the NO-releasing particles. For example, the presently disclosed NO-releasing particles can be administered via inhalation to treat bacterial infections related to cystic fibrosis. Cystic fibrosis-related bacterial infections include, but are not limited to, *Pseudomonas aeruginosa* (*P. aeruginosa*) infections.

V.C. Doses

The term "effective amount" is used herein to refer to an amount of the therapeutic composition (e.g., a composition comprising a nitric oxide-releasing particle) sufficient to produce a measurable biological response. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including the activity of the composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12. See Freireich et al., *Cancer Chemother Rep.* 50, 219-244 (1966). Drug doses also can be given in milligrams per square meter of body surface area because this method rather than body weight achieves a good correlation to certain metabolic and excretionary functions. Moreover, body surface area can be used as a common denominator for drug dosage in adults and children as well as in different animal species. See Freireich et al., *Cancer Chemother Rep.* 50, 219-244 (1966). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

For additional guidance regarding formulation and dose, see U.S. Pat. Nos. 5,326,902; 5,234,933; PCT International Publication No. WO 93/25521; Berkow et al., *The Merck Manual of Medical Information*, Home ed., Merck Research Laboratories: Whitehouse Station, N.J. (1997); Goodman et al., *Goodman & Gilman's the Pharmacological Basis of Therapeutics*, 9th ed. McGraw-Hill Health Professions Division: New York (1996); Ebadi, *CRC Desk Reference of Clinical Pharmacology*, CRC Press, Boca Raton, Fla. (1998); Katzunq, *Basic & Clinical Pharmacology*, 8th ed. Lange Medical Books/McGraw-Hill Medical Pub. Division: New York (2001); Remington et al., *Remington's Pharmaceutical Sciences*, 15th ed. Mack Pub. Co.: Easton, Pa. (1975); and Speight et al., *Avery's Drug Treatment: A Guide to the Properties, Choice, Therapeutic Use and Economic Value of Drugs in Disease Management*, 4th ed. Adis International: Auckland/Philadelphia (1997); Dutch et al., *Toxicol. Lett.*, 100-101, 255-263 (1998).

V.D. Routes of Administration

Suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the presently disclosed subject matter depends on various factors, including but not limited to the agent and/or carrier employed, the severity of the condition to be treated, and mechanisms for metabolism or removal of the active agent following administration.

VI. Compositions Containing No-Releasing Particles

Figure 9:
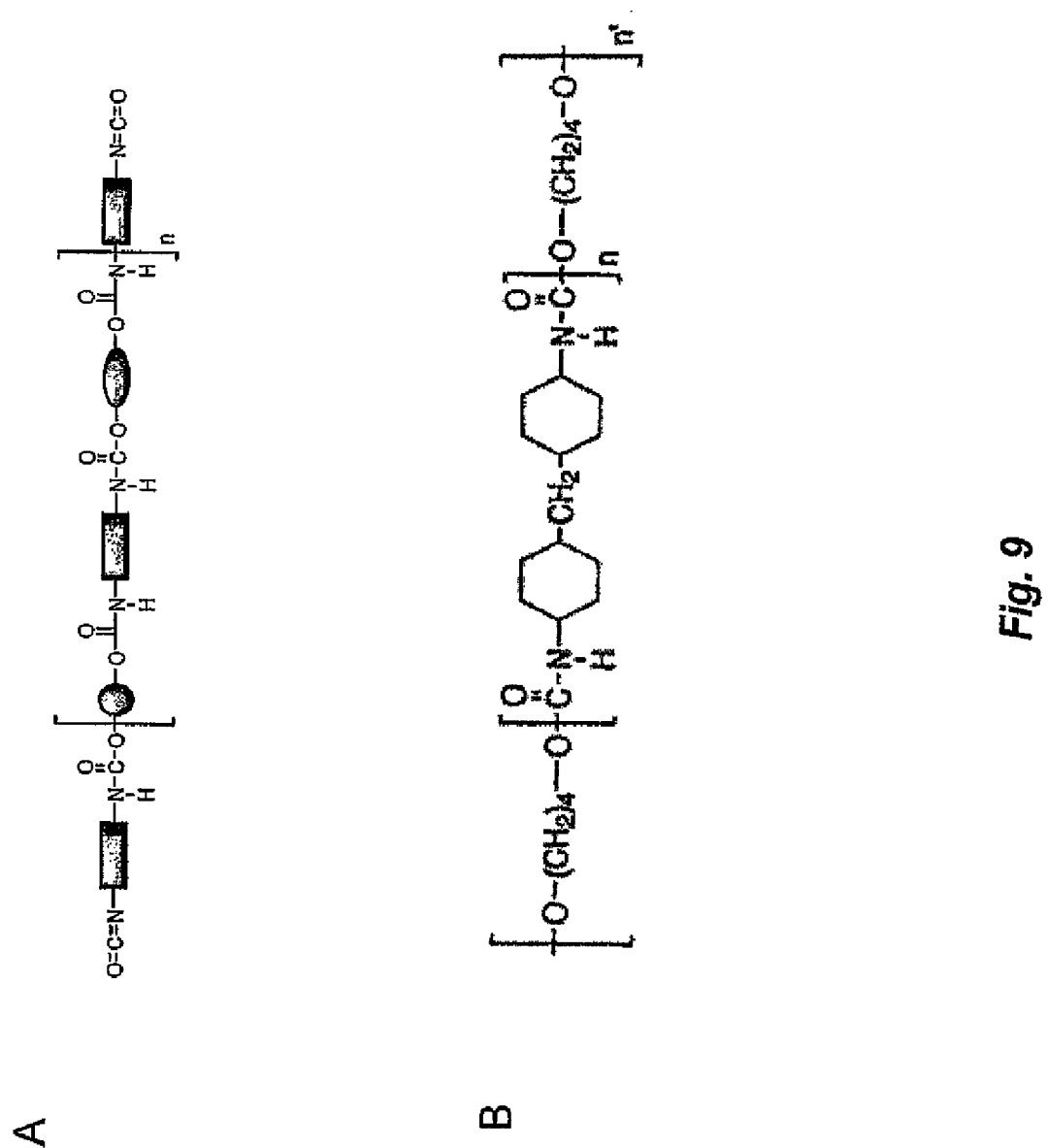
FIG. 9A shows a generalized structure of a medically segmented polyurethane. Soft units are represented by the shaded ellipses, hard units by shaded rectangles, and expander units by shaded circles.
FIG. 9B shows the structure of TECOFLEX® polyurethane, wherein n and n' are integers.

In some embodiments, the NO-releasing particles can be incorporated into polymeric films. Such incorporation can be through physically embedding the particles into polymer surfaces, via electrostatic association of particles onto polymeric surfaces, or by covalent attachment of particles onto reactive groups on the surface of a polymer. Alternatively, the particles can be mixed into a solution of liquid polymer precursor, becoming entrapped in the polymer matrix when the polymer is cured. Polymerizable groups can also be used to functionalize the exterior of the particles, whereupon, the particles can be co-polymerized into a polymer during the polymerization process. Suitable polymers into which the NO-releasing particles can be incorporated include polyolefins, such as polystyrene, polypropylene, polyethylene, polytetrafluoroethylene, and polyvinylidene, as well as polyesters, polyethers, polyurethanes, and the like. In particular, polyurethanes can include medically segmented polyurethanes. A generalized structure for a medically segmented polyurethane is shown in FIG. 9A. Such polyurethanes can include hard segments, i.e., moieties that are relatively rigid, and soft segments, i.e., moieties having more degrees of freedom that can exist in a number of alternate, inter-converting conformations. Medically segmented polyurethanes can also include one or more expander moieties, such as alkylene chains, that add additional length or weight to the polymer. Such polyurethanes are also generally non-toxic. One example of a medically segmented polyurethane is TECOFLEX®. See FIG. 9B.

Polymeric films containing NO-releasing particles can be used to coat a variety of articles, particularly surgical tools, biological sensors, and medical implants to prevent platelet adhesion, to prevent bacterial infection, to act as a vasodilator. These articles can be of use in vascular medical devices, urological medical devised, biliary medical devices, gastrointestinal medical devices, medical devices adapted for placement at surgical sites, and medical devices adapted for placement on skin wounds or openings. Thus, the polymers can be used to coat arterial stents, guide wires, catheters, trocar needles, bone anchors, bone screws, protective platings, hip and joint replacements, electrical leads, biosensors, probes, sutures, surgical drapes, wound dressings, and bandages.

In some embodiments, the device being coated can have a metallic surface, such as, for example, stainless steel, nickel, titanium, aluminum, copper, gold, silver, platinum, and combinations thereof. In some embodiments, the films or polymers containing the NO-releasing particles can be used to coat non-metallic surfaces, such as glass or fiber (e.g., cloth or paper)

Additionally, polymers containing NO-releasing particles can be used to form the devices, themselves. For example, the polymers can be fashioned into storage bags for blood or tissue or as wound dressings.

Further, the NO-releasing particles can be incorporated into detergents, such as, but not limited to, anti-microbial soaps. For example, NO-release in particles embedded in bar soaps can be triggered by contact with water and/or a drop in pH upon use. As the outer surface of the bar is eroded or dissolved, additional particles within the bar surface become exposed for subsequent uses of the bar. NO-releasing particles also can be suspended in liquid soaps. Such soaps or detergents can be used for personal hygiene or to provide anti-microbial treatments for fibers. Such soaps or detergents can also be used to treat household surfaces or any surface in a hospital or other medical environment that may be exposed to microbes such as bacteria, fungi or viruses.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Synthesis of Amine Functionalized Gold Nanoparticles

Figure 10:
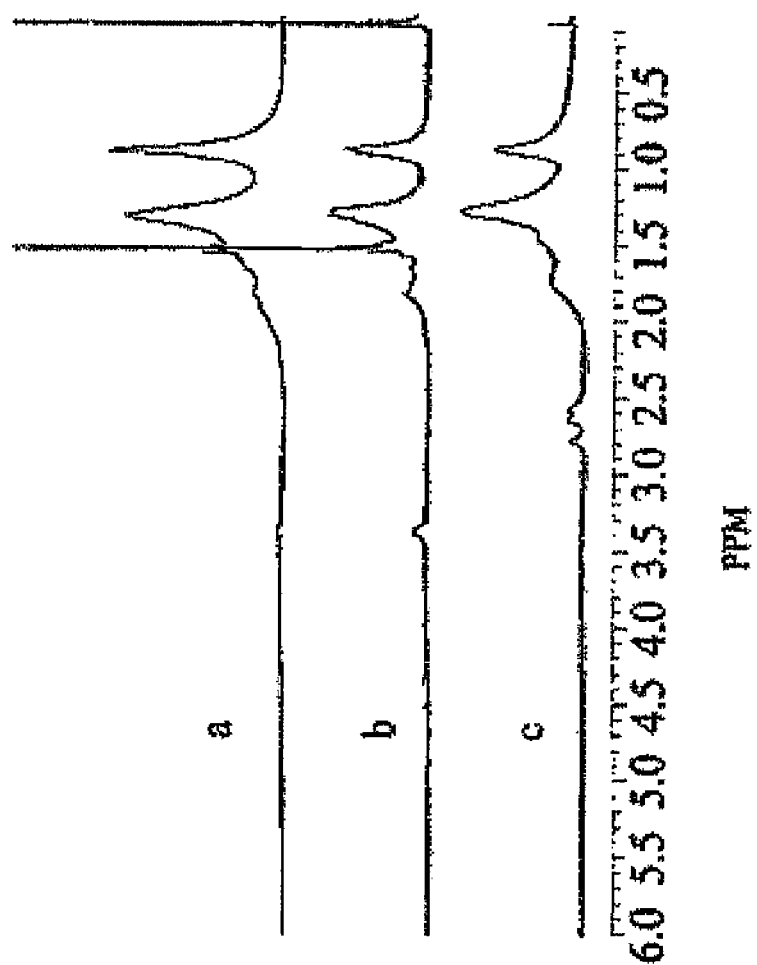
FIG. 10A is a $^1$H NMR spectrum of hexanethiol-functionalized gold nanoparticles.
FIG. 10B is a $^1$H NMR spectrum of bromine-functionalized gold nanoparticles, The —$CH_2Br$ peaks appear at 3.4 ppm.
FIG. 10C is a $^1$HNMR spectrum of ethylenediamine-functionalized gold nanoparticles. The —CH$_2$NH peaks appear from 2.5 to 3.0 ppm.

Gold nanoparticles were functionalized with amines in a two-step process by first place exchanging Br-functionalized thiol ligands onto the gold nanoparticle core with subsequent addition of amine by a reaction with Br. See FIG. 2. Sample $^1$H NMR spectra were acquired for each step of the synthesis, as presented in FIG. 10.

More particularly, gold nanoparticles were synthesized by the Brust method, via the reaction of hydrogen tetrachloroaurate salt with hexanethiol in the presence of sodium borohydride. See Hostetler, M. I., et al., *Langmuir*, 14, 17-30 (1998), After 30 min, the reaction was quenched with water. The nanoparticles were collected by filtration and washed with acetonitrile, then functionalized with bromo-terminated alkanethiols by the place exchange method. See Hostetler, M. I., et al., *Langmuir*, 15, 3782-3789 (1999).

The incoming bromo-terminated ligand (11-Bromo-1-undecanethiol as synthesized in Example 2, described herein below), see Troughton B. B., et al., *Langmuir*, 4, 365-385 (1988), was added (3:1 ratio of bromo- to methyl-terminated alkanethiol) to a solution of gold nanoparticles in methylene chloride and stirred for 30 min. The solvent was removed by rotary evaporation, and the gold nanoparticles were purified with acetonitrile. The extent of ligand exchange, monitored by NMR, was controlled by varying the reaction time and/or concentration of bromo-alkanethiol. The bromo-functionalized gold nanoparticles were then dissolved in toluene or methylene chloride and reacted with ethylenediamine, butylamine, hexanediamine, or diethylenetriamine. The disappearance of the —$CH_2Br$ peak in the NMR spectra of the functionalized nanoparticles indicated the completion of the reaction (See FIG. 10). The amine-functionalized gold nanoparticles were then suspended in a solution of methanol and sodium methoxide base and pressurized to 5 atm NO for 3 days with constant stirring to facilitate the synthesis of diazeniumdiolate NO donors. The N-diazeniumdiolate-modified monolayer protected clusters (MPCs) were filtered, washed with excess methanol, and stored at −4° C. until use.

The size and stability of the MPC gold nanoparticles were characterized using thermal gravimetric analysis (TGA), UV-Vis spectroscopy, and transmission electron microscopy (TEM). The organic content of hexanediamine-modified gold nanoparticles was determined to be approximately 22%, a value consistent with previous reports for hexanethiol-MPCs composed of 140 gold atoms (core) protected by 53 thiol ligands. See Hostetler, M. I., et al., *Langmuir*, 14, 17-30 (1998).

Because NO is highly reactive and might disrupt gold sulfur bonds, see Hrabie, J. A. and Keefer, L. K., *Chemical Reviews*, 102, 1135-1154 (2002), the stability of the hexanethiol-MPCs after exposure to high pressures of NO was evaluated using TGA and UV-Vis spectroscopy to ensure that the conditions necessary for diazeniumdiolate formation did not compromise nanoparticle integrity. Both the organic content of the nanoparticles (as studied by TGA) and the UV-Vis spectra remained the same following NO exposure indicating negligible influence on monolayer stability. Transmission electron microscopy images further confirmed that the core diameter of the nanoparticles remained constant (2.1±0.9 nm) regardless of amine derivatization or diazeniumdiolate formation. These studies suggest that the structural integrity of the MPC gold nanoparticles was not compromised by the conditions necessary to synthesize the NO donor and Introduce NO-release capability.

Example 2

11-Bromo-1-Undecanethiol Synthesis

Figure 11:
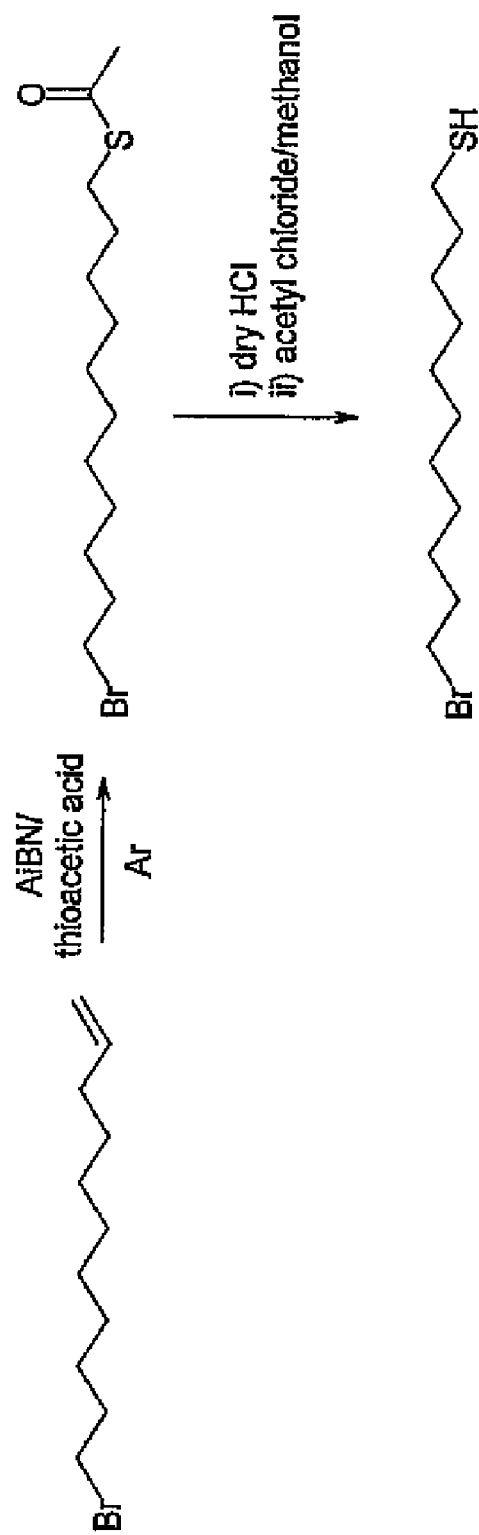
FIG. 11 is a scheme for a two-step synthesis of 11-bromo-1-undecanethiol.

11-Bromo-1-undecanethiol was synthesized in two steps (see FIG. 11). First, 11-bromo-1-undecene (5.0 g) was converted to a thioacetate by reacting with AiBN (1.5 g) and thioacetic acid (10 mL) in toluene (50 mL). The reaction was run under Ar and refluxed for 2 h. The solution was washed with excess water and the toluene removed by rotary evaporation. The thioacetate was converted into a thiol by exposing the 11-bromo-1-undecanethioacetate to dry HCl. Acetyl chloride (6 mL) was added dropwise to dry methanol in an ice bath under Ar. The solution was allowed to warm to room temperature and the reaction progressed for approximately 6 h. Methylene chloride and water were added and the methylene chloride layer was washed several times with water. The solvent was removed by rotary evaporation.

Example 3

General Procedure for Measuring Nitric Oxide Release

Figure 12:
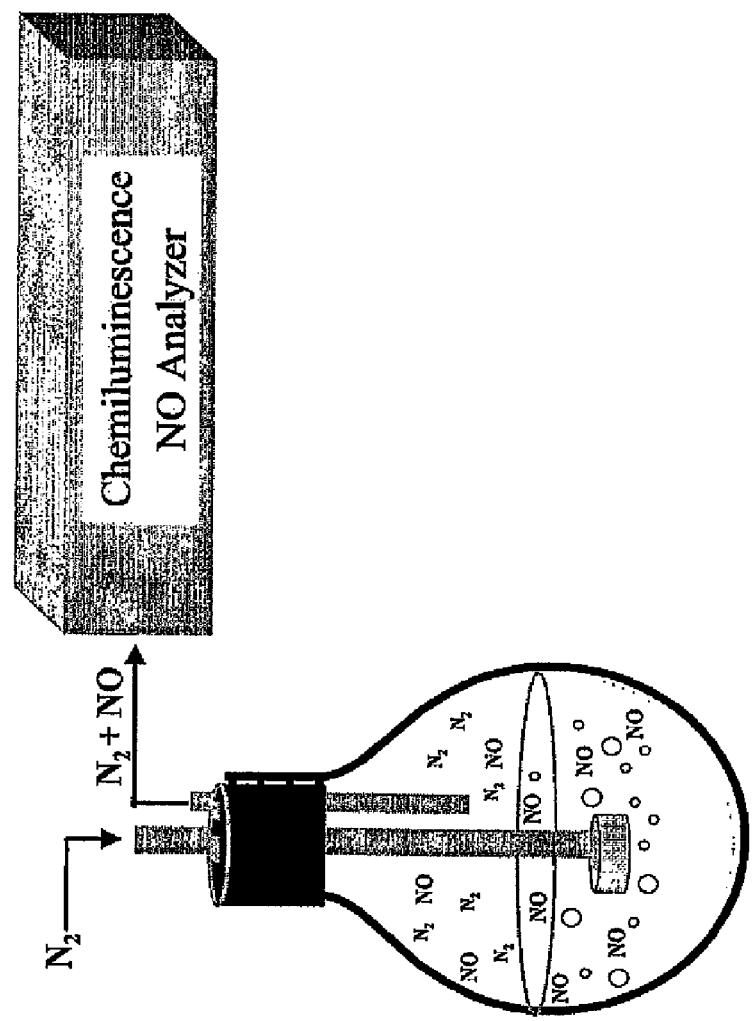
FIG. 12 is a schematic representation of an analytical method for measuring nitric oxide.

Nitric oxide release of the presently disclosed NO-releasing particles was measured according to the following general procedure. Referring now to FIG. 12, a predetermined volume of phosphate buffer solution (PBS) (pH 7.4, 37° C.) was disposed in a receptacle, e.g., a round-bottomed flask. The receptacle was sealed, leaving an inlet for nitrogen gas and an outlet for a mixture of nitrogen and nitric oxide. The outlet was in fluid communication with a chemiluminescence nitric oxide analyzer. An aliquot of a solution containing a diazeniumdiolated species was injected into the PBS buffer. The chemiluminescence nitric oxide analyzer measured the amount of NO that reacted with ozone (O3) to form excited $NO_2^*$, which emitted electromagnetic radiation (hv) as shown in Scheme 2.

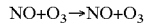

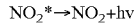

Scheme 2. Measurement of NO by chemiluminescence.

Example 4

Measurement of Nitric Oxide Release from Amine-Derivatized Monolayer Protected Gold Nanoparticles Nitric oxide release was measured in phosphate buffered saline solution at physiological temperature and pH using a Sievers NOA™ chemiluminescence nitric oxide analyzer (Boulder, Colo., United States of America). As presented in Table 1, below and in FIG. 13, the NO-release for diazeniumdiolate-modified gold nanoparticles was tunable by varying the number and/or the chemical structure of the substituted amine ligands. A schematic showing the release of nitric oxide from a functionalized monolayer protected cluster (MPC) gold nanoparticle is shown in FIG. 14.

TABLE 1

Nitric Oxide Release Properties of Amine-Derivatized Monolayer Protected Gold Nanoparticles.

| Ligand | % Amine | Half-life (min) | Release Longevity (min) | Total NO (pmol/mg) |
|---|---|---|---|---|
| Hexane | — | 2 | 55 | 400 |
| Butylamine | 21 | 15 | 60 | 2,000 |
| Ethylenediamine | 14 | 78 | 200 | 9,750 |
| Ethylenediamine | 21 | 88 | 300 | 19,300 |
| Hexanediamine | 21 | 68 | 600 | 87,000 |
| Diethylenetriamine | 21 | 63 | 360 | 38,000 |

Example 5

Figure 13:
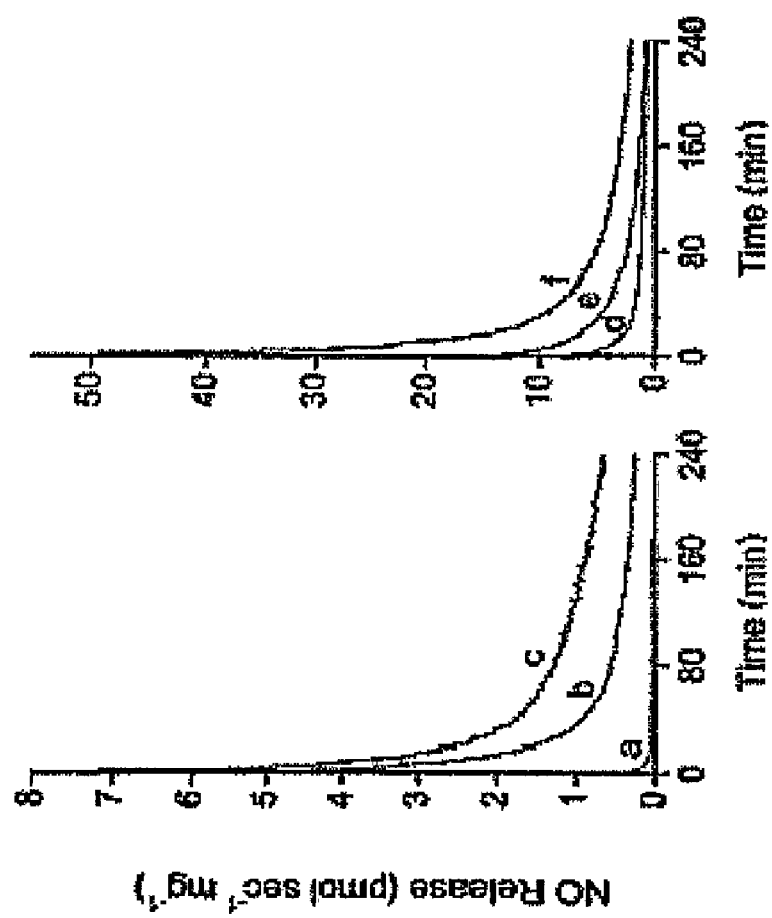
FIG. 13 is a plot showing nitric oxide release profiles from monolayer, protected cluster (MPC) gold nanoparticles derivatized with various diamines. Line a is the nitric oxide release profile of underivatized MPC gold nanoparticles. Line b is the nitric oxide release profile from MPC gold nanoparticles derivatized with 14% ethylenediamine. Line c shows the nitric oxide release profile from MPC gold nanoparticles derivatized with 21% ethylenediamine. Line d shows the nitric oxide release profile from MPC gold nanoparticles derivatized with 21% ethylenediamine. Line e shows the nitric oxide release profile from MPC gold nanoparticles derivatized with 21% diethylenetriamine. Line f shows the nitric oxide release profile from MPC gold nanoparticles derivatized with 21% hexanediamine.
Figure 14:
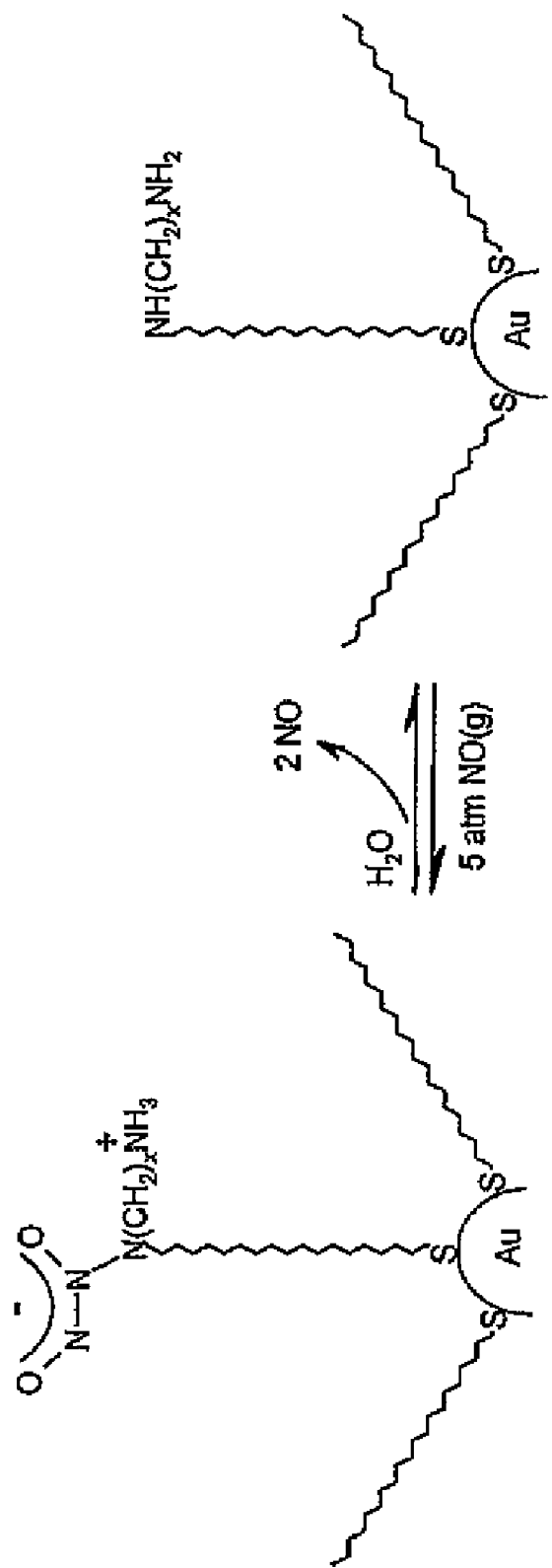
FIG. 14 is a schematic representation showing the release of nitric oxide from functionalized monolayer protected cluster (MPG) gold nanoparticles.

Results From NO-Releasing Particles Comprising Monolayer Protected Gold Nanoparticles Referring once again to Table 1 and FIG. 13, increasing the concentration of ethylenediamine ligand from 14 to 21% led to a corresponding increase in total NO release (9750 to 19,300 pmol NO/mg MPC) and NO release duration (from 200 to 300 min). Without being bound to any particular theory of operation, it is suggested that the elevated NO release is attributed to enhanced NO-donor formation due to a larger concentration of amines. A small amount of NO (400 pmol/mg) also was measured from the hexanethiol MPC controls. This NO release was negligible at periods greater than 5 min, suggesting that a small amount of NO likely intercalates within the hydrophobic alkyl chains under the conditions necessary for diazeniumdiolate synthesis (5 atm NO), but such NO is rapidly released upon solution immersion.

The diazeniumdiolate-modified MPCs also released low levels of NO under a warm (37° C.) stream of nitrogen gas, suggesting a possible thermal dissociation mechanism. The level of NO release, however, was greater in buffer, suggesting that the N-diazeniumdiolate-modified nanoparticles undergo both proton driven and thermal dissociation. The diazeniumdiolate-modified MPCs retained full NO release characteristics when stored under nitrogen at −4° C. for up to 14 days (the longest period investigated).

The NO release from diazeniumdiolate-modified MPCs also was tunable by varying the amine precursor structure. Increasing the length of the alkyl chain separating the nitrogens from two to six methylene units led to an increase in the total amount of NO released (see Table 1 and FIGS. 13, *d* and *f*) (19,300 to 87,000 pmol NO/mg MPC for ethylenediamine- and hexanediamine-modified MPCs, respectively), suggesting a NO release/diazeniumdiolate structure relationship.

Indeed, the half-life data (Table 1) show that separating the amines results in a more rapid release of NO as well, analogous to the dissociation behavior reported for small molecule diazeniumdiolates. See Hrabie, J. A., et al., *J. Org. Chem.*, 58, 1472-1476 (1993); Davies, K. M., et al., *J. Am. Chem. Soc.*, 123, 5473-5481 (2001).

The total amount of NO released from diethylenetriamine-modified MPCs (38,000 pmol NO/mg) was between that measured for ethylenediamine- and hexanediamine-modified MPCs. The presence of an additional secondary amine in diethylenetriamine likely accounts for increased NO donor formation (and release capability) relative to ethylenediamine, even though the length of the alkyl chain separating the nitrogens remains short (two methylene units).

Butylamine-modified MPCs, a secondary monoamine derivative, were characterized by the lowest total NO release of all the amine-modified MPCs studied. Diazeniumdiolate formation is facilitated by the additional amine. See Hrabie, J. A., et al., *J. Org, Chem.*, 58, 1472-1476 (1993); Davies, K. M., et al., *J. Am, Chem. Soc.*, 123, 5473-5481 (2001). Notably, the diazeniumdiolate conversion efficiency for the amine-modified MPCs was calculated to be less than 1%, regardless of amine structure.

Example 6

Preparation of Nitric Oxide-Releasing Dendrimers

Scheme 3. General procedure for dendrimers with lipophilic tails.

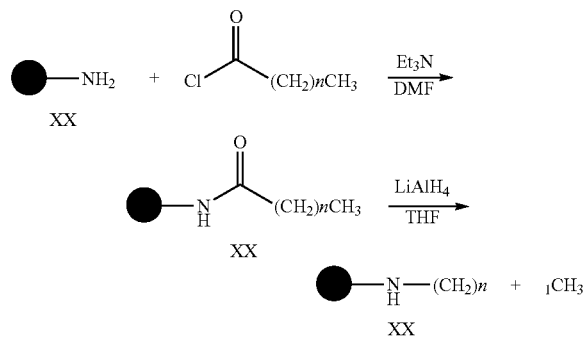

Figure 15:
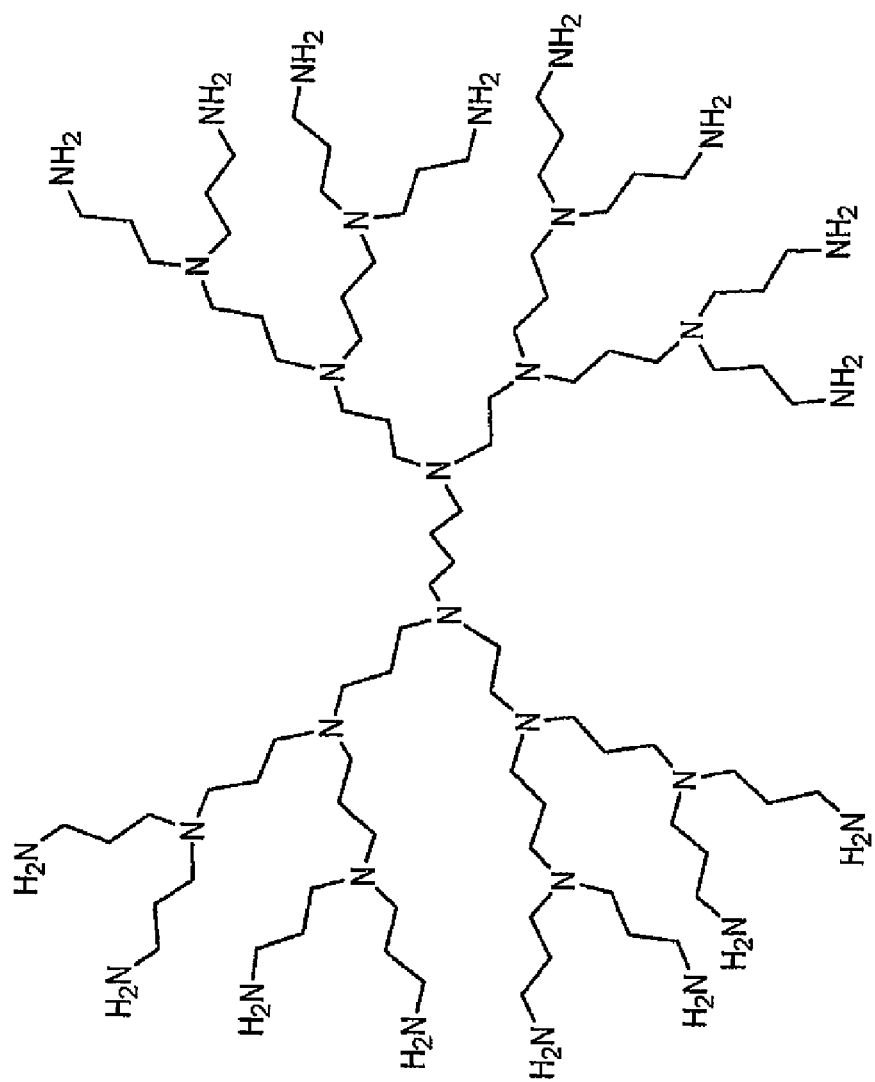
FIG. 15 is a schematic representation of the chemical structure of polypropylenimine hexadecaamine dendrimer (DAB-Am-16).

Polypropylenimine hexadecaamine dendrimer (DAB-Am-16, available from Aldrich Chemical Company, Milwaukee, Wis., United States of America) (see FIG. 15) was charged at 5-atm nitric oxide for three days in the presence of sodium methoxide (NaOMe). This procedure yielded 0.74 moles nitric oxide/mole dendrimer (2.3% conversion) and $2.3 \times 10^8$ moles nitric oxide released.

Figure 16:
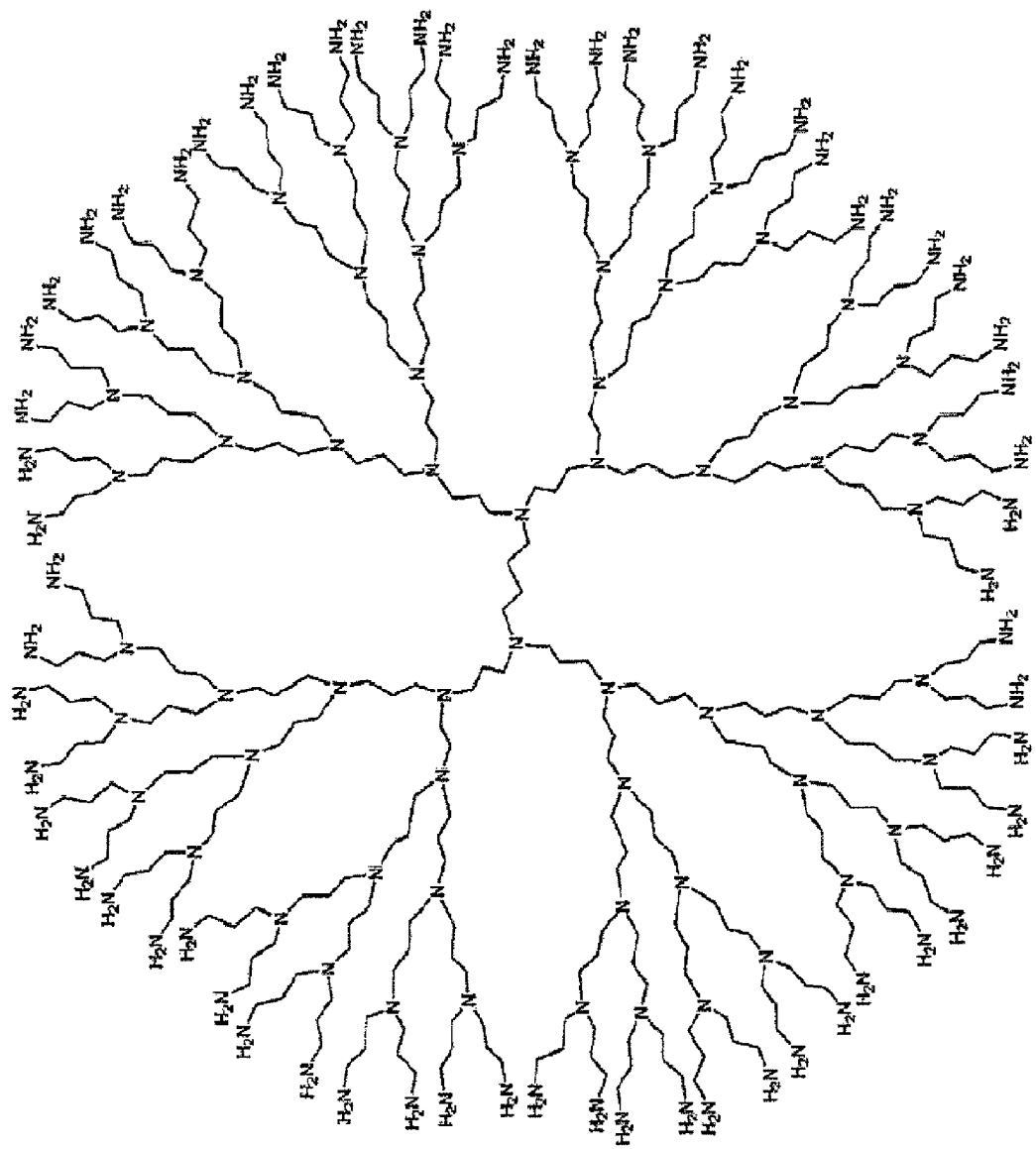
FIG. 16 is a schematic representation of the chemical structure of polypropylenimine tetrahexacontaamine dendrimer (DAB-Am-64).

Polypropylenimine tetrahexacontaamine dendrimer (DAB-Am-64, available from Aldrich Chemical Company, Milwaukee, Wis., United States of America) (see FIG. 16) was charged at 5-atm nitric oxide for three days in the presence of NaOMe. This procedure yielded 4.94 moles nitric oxide/mole dendrimer (3.9% conversion) and $1.18 \times 10^8$ moles nitric oxide released.

DAB-C7-16 (see Scheme 4 below) was charged at 5-atm nitric oxide for three days In the presence of NaOMe/MeOH (Scheme 5). This procedure yielded 12 moles NO/mole dendrimer (37.9% conversion) and $3.74 \times 10^{-7}$ moles NO released.

Scheme 4. Preparation of DAB-C7-16.

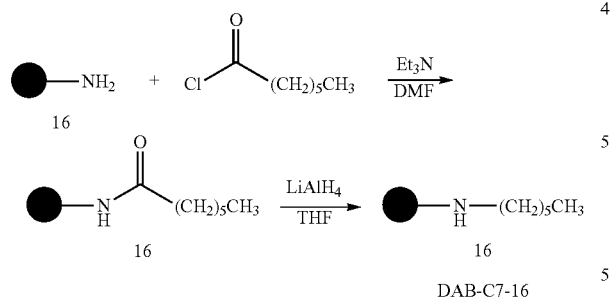

Scheme 5. Preparation of DAB-C7-16 diazeniumdiolate.

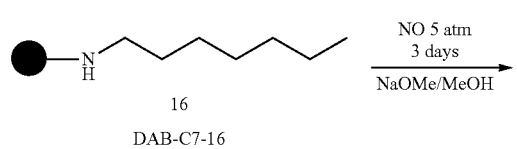

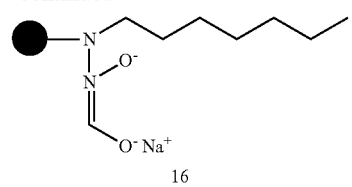

DAB-C7-64 was charged at 5-atm nitric oxide for three days in the presence of NaOMe/MeOH. This procedure yielded 45 moles NO/mole dendrimer (35.6% conversion) and $1.48 \times 10^{-7}$ moles NO released.

Figure 17:
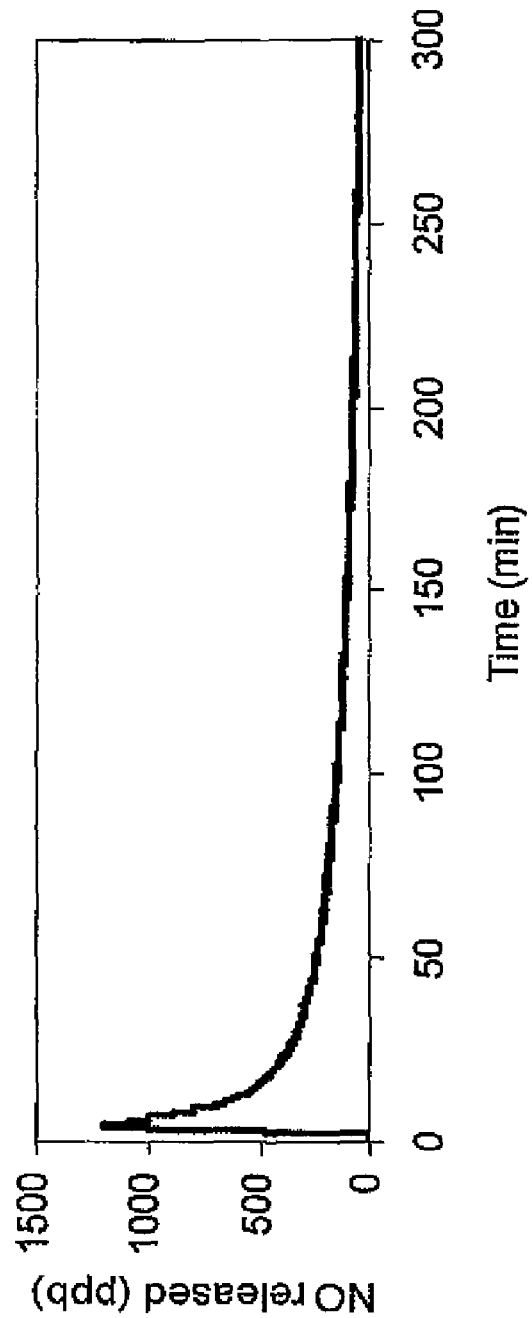
FIG. 17 is a graph showing the nitric oxide release profile for DAB-C7-16 NaOMe/MeOH.
Figure 18:
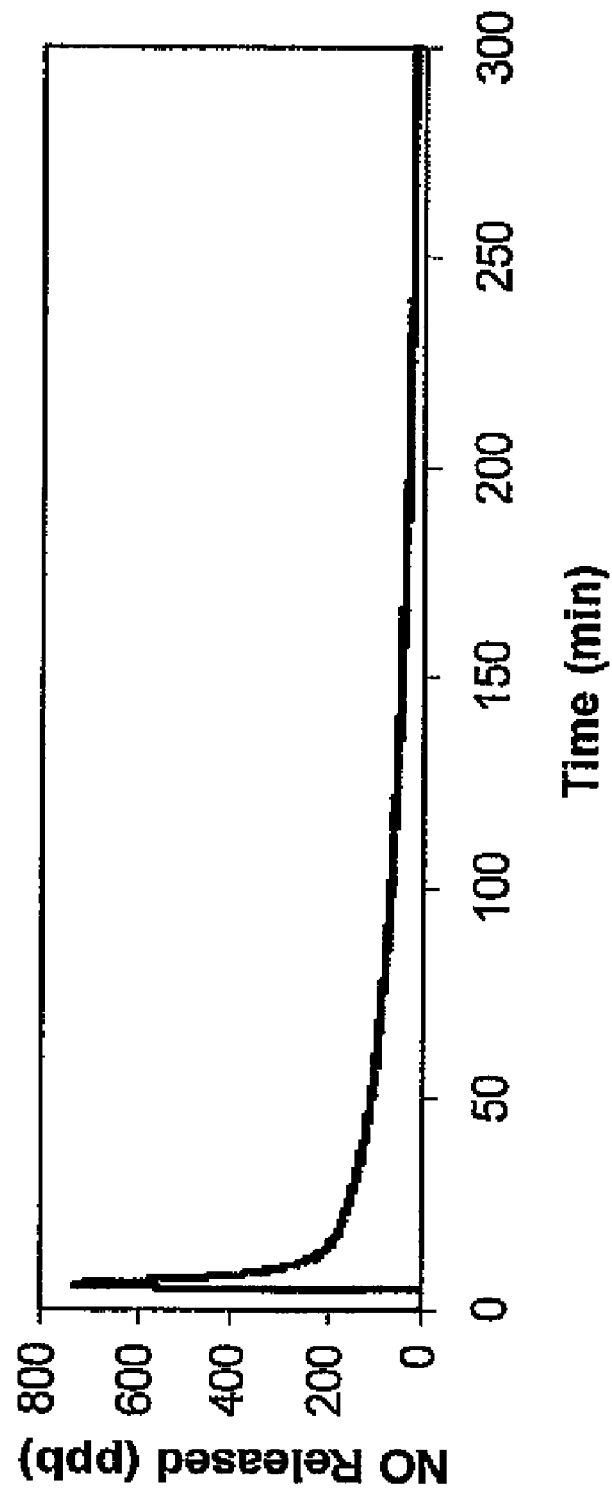
FIG. 18 is a graph showing the nitric oxide release profile for DAB-C7-64 NaOMe/MeOH.

A graph showing nitric oxide release versus time for DAB-C7-16 NaOMe/MeOH is shown in FIG. 17. Likewise, a graph showing nitric oxide release versus time for DAB-C7-64 NaOMe/MeOH is shown in FIG. 18.

DAB-Ac-16 (Scheme 6) was charged at 5-atm nitric oxide for three days in the presence of NaOMe. This procedure yielded 0.039 moles NO/mole dendrimer (0.12% conversion) and $4.95 \times 10^{-10}$ moles NO released.

Scheme 6. Preparation of DAB-Ac-16.

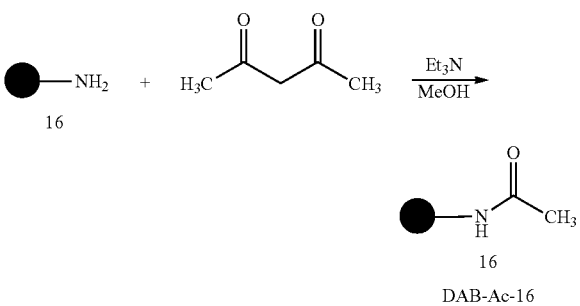

DAB-Ac-64 was charged at 5-atm nitric oxide for three days in the presence of NaOMe. This procedure yielded 0.22 moles NO/mole dendrimer (0.17% conversion) and $3.75 \times 10^{-10}$ moles NO released.

DAB-Pro-16 (Scheme 7) was charged at 5-atm nitric oxide for three days in the presence of NaOMe. This procedure yielded 42 moles NO/mole dendrimer (130% conversion) and $1.92 \times 10^{-7}$ moles NO released.

Scheme 7. Preparation of DAB-Pro-16.

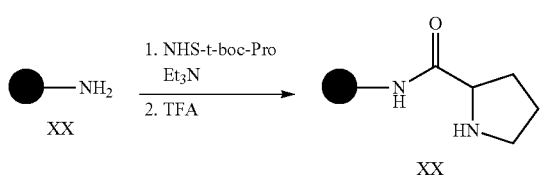

DAB-Pro-64 was charged at 5-atm nitric oxide for three days in the presence of NaOMe. This procedure yielded 480 moles NO/mole dendrimer (377% conversion) and $4.79 \times 10^{-7}$ moles NO released.

Example 7

Measurement of Nitric Oxide Release from Amine-Derivatized Dendrimers

NO release from amine-derivatized dendrimers synthesized as described in Example 6 was measured according to the procedure outlined in Example 1 Results are summarized below in Table 2.

TABLE 2

Summary of Nitric Oxide Release from Amine Derivatized Dendrimers

| Diazeniumdiolated Species | NO Released (mmol NO/g) | $T_{1/2}$ (min) | moles NO/mol dendrimer | Amine Structure |
|---|---|---|---|---|
| DAB-Ac-16 | 0.016 | 1.4 | 0.04 | capped |
| DAB-Ac-64 | 0.02 | 2.5 | 0.22 | |
| DAB-Am-16 | 0.44 | 12 | 0.74 | primary |
| DAB-Am-64 | 0.69 | 29 | 4.94 | |
| DAB-C7-16 | 3.4 | 80 | 12 | secondary |
| DAB-C7-64 | 3.2 | 90 | 45 | |
| DAB-Pro-16 | 13 | 150 | 42 | secondary |
| DAB-Pro-64 | 36 | 117 | 480 | |

Example 8

Measurement of Nitric Oxide Release from Diazeniumdiolated Materials

NO release from a variety of NO-releasing materials was measured according to the procedure outlined in Example 3. Results are summarized below in Table 3. The diazeniumdiolated fumed silica particles were prepared as described in Example 9, below, grafting the fumed silica surface to N-(6-aminohexyl)-3-aminopropyltrimethoxysilane, followed by diazeniumdiolation of the secondary amine with NO gas.

TABLE 3

Summary of Nitric Oxide Release from Diazeniumdiolated Materials

| Diazeniumdiolated Species | NO Released (mmol NO/g) | tv2 (min) |
|---|---|---|
| Proteins (Bovine serum albumin (BSA) | 0.54 | 7.2E4. |
| Fumed Silica (2N[6]-$N_2O_2$) | 0.56 | 43 |
| Sol-gels (20% AHAP3) | 0.24 | 45 |
| Polymethacrylate (C2-ED) | 0.94 | 60 |

Example 9

Synthesis Route to NO-Releasing Silica Particles

Figure 19:
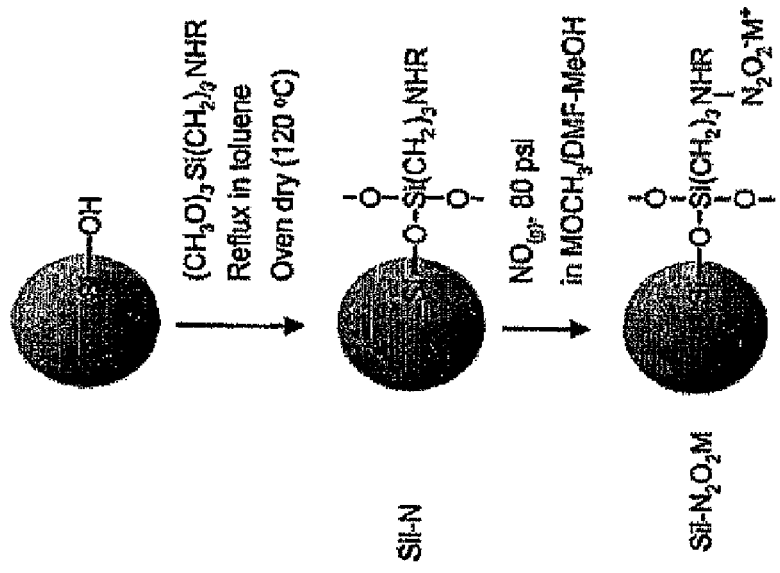
FIG. 19 is a synthesis route to NO-releasing silica particles according to the method described by Zhand, H., et al., *J. Am, Chem. Soc.*, 125, 5015 (2003).

Referring now to FIG. 19, NO-releasing silica particles with a particle size ranging from about 200 nm to about 300 nm are prepared following the method described by Zhang, H., et al., *J. Am. Chem. Soc.*, 125, 5015 (2003).

Example 10

Synthesis of Silica Based on Co-Condensation of NO Donor Precursors

Reagents and Materials: Tetraethyl orthosilicate (TEOS), tetramethylsilane (TMS), and sodium methoxide (NaOMe) were purchased from Fluke (Buchs, Switzerland). Silanes including (aminoethylaminomethyl)phenethyltrimeth-oxysilane (AEMP3), N-(6-aminohexyl)aminopropyltrimethoxysilane (AHAP3), N-(2-aminoethyl)-3-aminopropyltrimethoxysilane (AEAP3), and N-[3-(trimeth-oxysilyl)propyl]diethylenetriamine (DET3) were purchased from Gelest (Tullytown, Pa., United States of America). N,N-Dimethylformamide (DMF) was purchased from Sigma Chemical Company (St. Louis, Mo., United States of America). Methanol (MeOH), ethanol (EtOH), toluene, and ammonia solution ($NH_4OH$, 30 wt % in water) were purchased from Fisher Scientific (Fair Lawn, N.J., United States of America). Nitric oxide (NO, 99.5%), argon (Ar), and nitrogen ($N_2$) gases were obtained from AGA Gas (Maumee, Ohio, United States of America) or National Welders Supply (Raleigh, N.C., United States of America). Other solvents and chemicals were analytical-reagent grade and used as received. A Millipore Milli-Q UV Gradient A10 System (Millipore Corporation, Bedford, Mass., United States of America) was used to purify distilled water to a final resistivity of 18,2 MΩ-2 . cm and a total organic content ≦6 ppb.

Synthesis of Nitric Oxide-Releasing Silica Nanoparticles: Silane solutions were prepared by mixing 2.78 mmol (620 μL) of TEOS with different concentrations of AEAP3, AHAP3, AEMP3, or DET3 (0-0.70 mmol corresponding to 0-20 mol %, balance TEOS) for 10 min. The silane solution was then combined with 22 mL of EtOH and 6 mL of ammonia (30 wt % in water), and vigorously stirred for 30 min under ambient conditions. The white precipitate was collected by centrifugation (5000 rpm, 5 min), washed with EtOH copiously, and dried under vacuum overnight.

The resulting amine-functionalized silica was resuspended in 18 mL of DMF and 2 mL of MeOH in the presence of NaOMe (0.32-0.70 mmol; adding an equimolar amount of NaOMe corresponding to the secondary amine content of silica composites) and placed in 10 mL-vials equipped with a stir bar. The vials were placed in a Parr bottle (200 mL), connected to an in-house NO reactor, and flushed with Ar six times to remove oxygen in the suspension. The reaction bottle was then charged with NO to 5 atm and sealed for 3 d while stirring. The NO gas was purified over KOH pellets for 2 h to remove trace NO degradation products. Prior to removing the silica particles, unreacted NO was purged from the chamber with Ar. The N-diazeniumdiolate-modified silica particles were recollected by centrifugation at 5000 rpm for 5 min, washed copiously with ethanol, dried under ambient conditions for 1 h, and stored in a sealed container at −20° C. until used

Example 11

Characterization of Functionalized Silica

Solid-state cross polarization/magnetic angle spinning (CP/MAS) [29] Si nuclear magnetic resonance (NMR) spectra were obtained at 293 K on a Bruker 360 MHz DMX spectrometer (Billerica, Mass., United States of America) equipped with wide-bore magnets (triple axis pulsed field gradient double resonance probes). Silica composite particles (0, 10, 13, and 17 mol % AEAP3, balance TEOS) were packed into 4 mm rotors (double resonance frequency of 71.548 MHz) and spun at a speed of 8.0 kHz. The chemical shifts were determined in ppm relative to a TMS external standard.

For atomic force microscopy (AFM) imaging, the silica particles were suspended in toluene, deposited on a freshly cleaved mica surface, and dried under ambient conditions for 3 h. Contact mode AFM images were obtained in air using a Molecular Force Probe 3D Atomic Force Microscope (Asylum Research; Santa Barbara, Calif., United States of America) controlled with a MFP-3D software running under Igor Pro (Wavemetrics; Lake Oswego, Oreg., United States of America). Triangular silicon nitride cantilevers with a nominal spring constant of 0.12 N/m$^{-1}$ and resonance frequency of 20 kHz (Veeco; Santa Barbara, Calif., United States of America) were used to acquire height/topography images at a scan rate of 0.5 Hz.

Nitric oxide release profiles of the N-diazeniumdiolate-modified silica nanoparticles were measured in deoxygenated phosphate-buffered saline (PBS, 0.01 M; 37° C.) at a pH 3.3, 4.3, 5,3, 6.0, 7.4, and 9.5 using a Sievers NOA 280i chemiluminescence nitric oxide analyzer (Boulder, Colo., United States of America). Nitric oxide released from the silica was transported to the analyzer by a stream of $N_2$ (200 mL/min) passed through the reaction cell. The instrument was calibrated with air (0 ppm NO) passed through a zero filter, and 24.1 ppm of NO standard gas (balance $N_2$, purchased from AGA Gas).

The surface area and pore volume of the silica were determined via nitrogen adsorption/desorption isotherms (see, Huh, S., et al., *Chem. Mater.*, 15, 4247-4256 (2003)) collected with a Beckman Coulter SA3100 Surface Area and Pore Size Analyzer (Fullerton, Calif., United States of America). The surface area and pore volume were calculated using the Brunauer-Emmett-Teller (BET) and Barrett-Joyner-Halenda (BJH) methods. Prior to the measurements, all silica samples were degassed at 200° C. for 3 h.

Example 12

Physical Characteristics of NO-Release Silica Nanoparticles Based on Co-Condensation of NO Donor Precursors The size of silica nanoparticles was tunable by varying the type and concentration of aminoalkoxysilane used. Contact mode atomic force microscope (AFM) images of silica spheres having different silane compositions are shown in FIGS. 20A-20E. The diameter of control (TEOS only) silica particles was 250±20 nm. Altering the TEOS solution to include 10 mol % AHAP3 decreased the diameter of the particles to 20±2 nm. Silica particles prepared from AEAP3 and TEOS were roughly twice as large (d=500±45 nm) than controls. As the mol % of AEAP3 was increased from 10 to 17 mol % (balance TEOS), the diameter of the particle decreased to 92±16 nm, revealing a pseudo-linear relationship between silica size and aminoalkoxysilane concentration (FIG. 20F). Similar trends in size were observed for each aminoalkoxysilane system studied. The size of the particles was not altered after N-diazeniumdiolate synthesis, indicating that the structural integrity of the silica particles was not compromised by the conditions necessary to form the NO donor and introduce NO release capability.

Figure 21A:
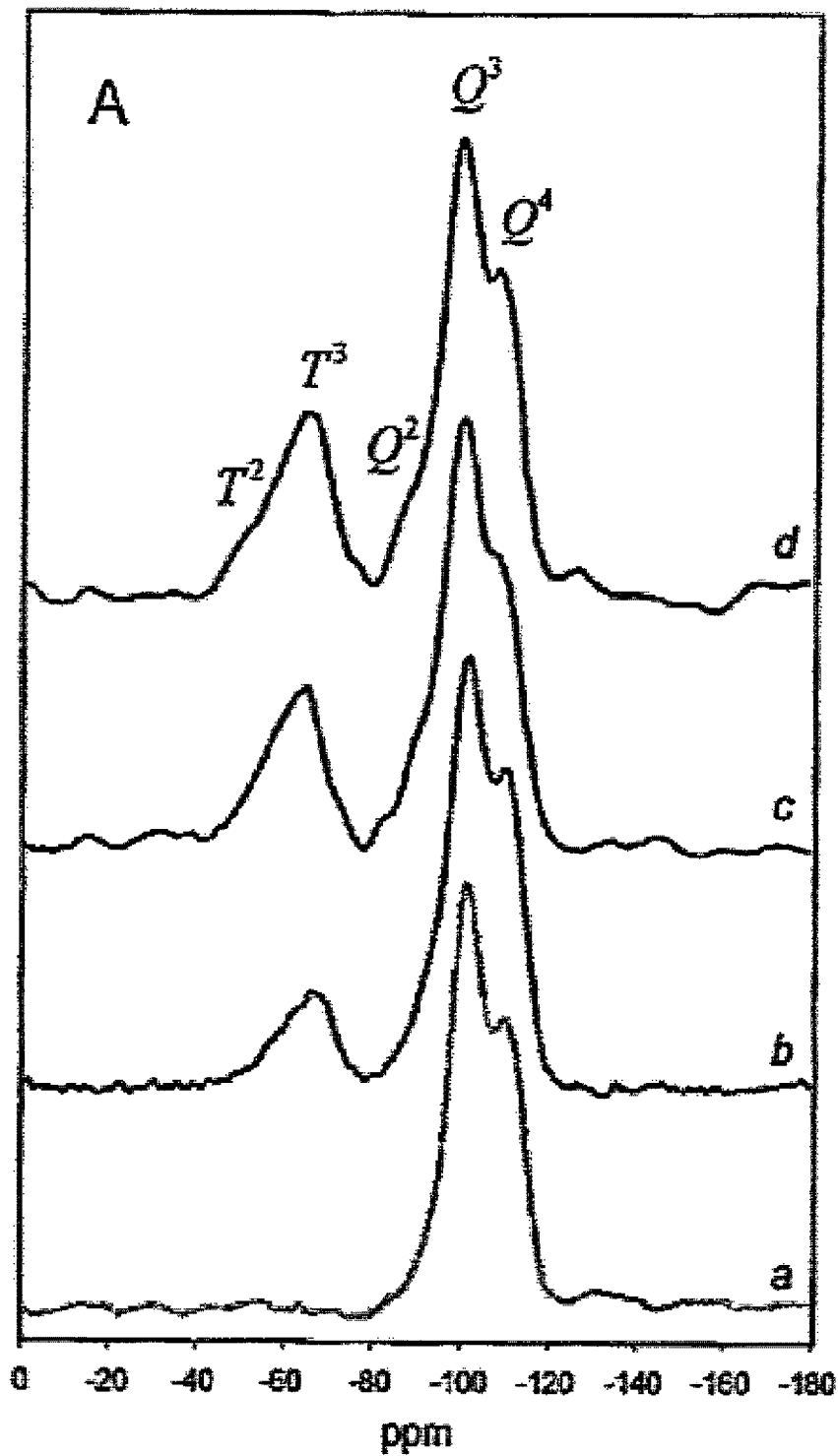
FIG. 21A is a plot showing the solid-state $^{29}$Si cross polarization/magic angle spinning (CP/MAS) NMR spectra of co-condensed silica with various amounts of AEAP3: (a) 0 AEAP3 (control), (b) 10 mol % AEAP3 (balance TEOS), (c) 13 mol % AEAP3 (balance TEOS); and 17 mol % AEAP3 (balance TEOS).

As shown in FIGS. 21A-21C, solid-state $^{29}$Si nuclear magnetic resonance (NMR) was used to confirm the incorporation of aminoalkoxy functionalities within the silica network and to determine the surface coverage (SC) of such ligands. Cross polarization and magic angle spinning (CP/MAS) techniques were employed to increase the signal resolution and sensitivity. Control and amine-functionalized silica particles prepared from 0 to 17 mol % AEAP3 (balance TEOS) were analyzed. For TEOS control silica, three distinct peaks in the $^{29}$Si NMR spectrum were observed at –90, –101, and –109 ppm, respectively, representative of $Q^2$ (geminal silanol; —$O_2Si(OH)_2$), $Q^3$ (single silanol; —$O_3Si(OH)$), and $Q^4$ (siloxane; —$O_4Si$) silicons. See Huh, S., et al., *Chem. Mater.*, 15, 4247-4256 (2003); and Albert, K., and Bayer, E. J., *J. Chromatogr.*, 544, 345-370 (1991). For the aminoalkoxysilane-modified silica particles, five peaks were observed in the spectra, indicating three additional silicon chemical environments (graphs b-d in FIG. 21A). The peaks at chemical shifts of approximately –52 and –65 ppm are representative of silicon connected to $T^2$ (—$O_2Si(OH)R$) and $T^3$ (—$O_3SiR$) structures, respectively (where R is an aminoethylaminopropyl group). See Huh, S., et al., *Chem. Mater.*, 15, 4247-4256 (2003); and Albert, K, and Bayer, E. J., *J. Chromatogr.*, 544, 345-370 (1991). The presence of $T^{11}$ bands suggests the existence of covalent linkages between aminoalkoxy groups and the silica backbone. The resonance lines representing $Q^2$, $Q^3$, and $Q^4$ were also assigned in the expected positions. As the AEAP3 content was increased from 10 to 17 mol %, the surface coverage of aminoalkoxy ligands [SC=$(T^2+T^3)/(T^2+T^3+Q^2+Q^3)$; see See Huh, S., et al., *Chem. Mater.*, 15, 4247-4256 (2003); and Radu, D. R., et al., *J. Am. Chem. Soc.*, 126, 1640-1641 (2004)]. Increased from 21 to 37% correspondingly. See FIG. 21C. Of note, the quantitative analysis of these structures is complicated because the intensity of each peak depends on the efficiency of cross polarization and the proton relaxation time. See Bruch, M. D., and Fatunmbi, H. O., *J. Chromatogr. A*, 1021, 61-70 (2003).

The surface area and pore volume of the silica nanoparticles were evaluated via nitrogen adsorption-desorption isotherms, as described previously. See Huh, S. et al., *Chem. Mater.*, 15, 4247-4256 (2003). As expected, the amine-functionalized silica proved to be nonporous with surface areas ($S_{BET}$) of 10-20 m$^2$·g$^{-1}$ and pore volumes ($V_p$) of 0.02-0.06 mL·g$^{-1}$ (at p/p$_0$=0.98).

Example 13

Results of NO-Release Silica Nanoparticles Based on Co-Condensation of NO Donor Precursors NO release characteristics including the total amount of NO (t[NO]), half-life of NO release ($t_{1/2}$), maximum flux of NO release ([NO]$_m$), and time necessary ($t_m$) to reach [NO]$_m$ were evaluated as a function of aminoalkoxysilane structure and amount. The results are summarized in Table 4, below.

TABLE 4

NO Release Properties of Silica Particles Prepared based on the Co-condensation of NO Donor Precursors[a]

| Ligand Type | Mol % | t[NO] (nmol/mg) | t$^{1/2}$ (h) | [NO]$_m$ (ppb/mg) | t$_m$ (h) |
|---|---|---|---|---|---|
| AEP3 | 10 | 145 ± 10 | 12 ± 4 | 14 ± 3 | 8 ± 1 |
| AEP3 | 13 | 392 ± 15 | 6 ± 1.5 | 92 ± 5 | 4 ± 1 |
| AEP3 | 17 | 600 ± 25 | 3.4 ± 0.4 | 140 ± 10 | 2.1 ± 0.3 |
| AHAP3 | 10 | 380 ± 20 | 0.85 ± 0.05 | 370 ± 10 | 0.35 ± 0.05 |
| AEMP3 | 10 | 53 ± 3 | 6.0 ± 0.2 | 10 ± 2 | 0.12 ± 0.01 |
| AEMP3 | 13 | 81 ± 3 | 6.5 ± 0.3 | 22 ± 2 | 0.10 ± 0.01 |
| AEMP3 | 17 | 118 ± 5 | 5.7 ± 0.5 | 32 ± 2 | 0.11 ± 0.02 |
| AEMP3 | 20 | 170 ± 10 | 5.4 ± 0.3 | 40 ± 3 | 0.11 ± 0.01 |
| DET3 | 10 | 120 ± 5 | 4.0 ± 0.2 | 22 ± 2 | 1.6 ± 0.1 |

[a]n is at least 3.

Figure 22:
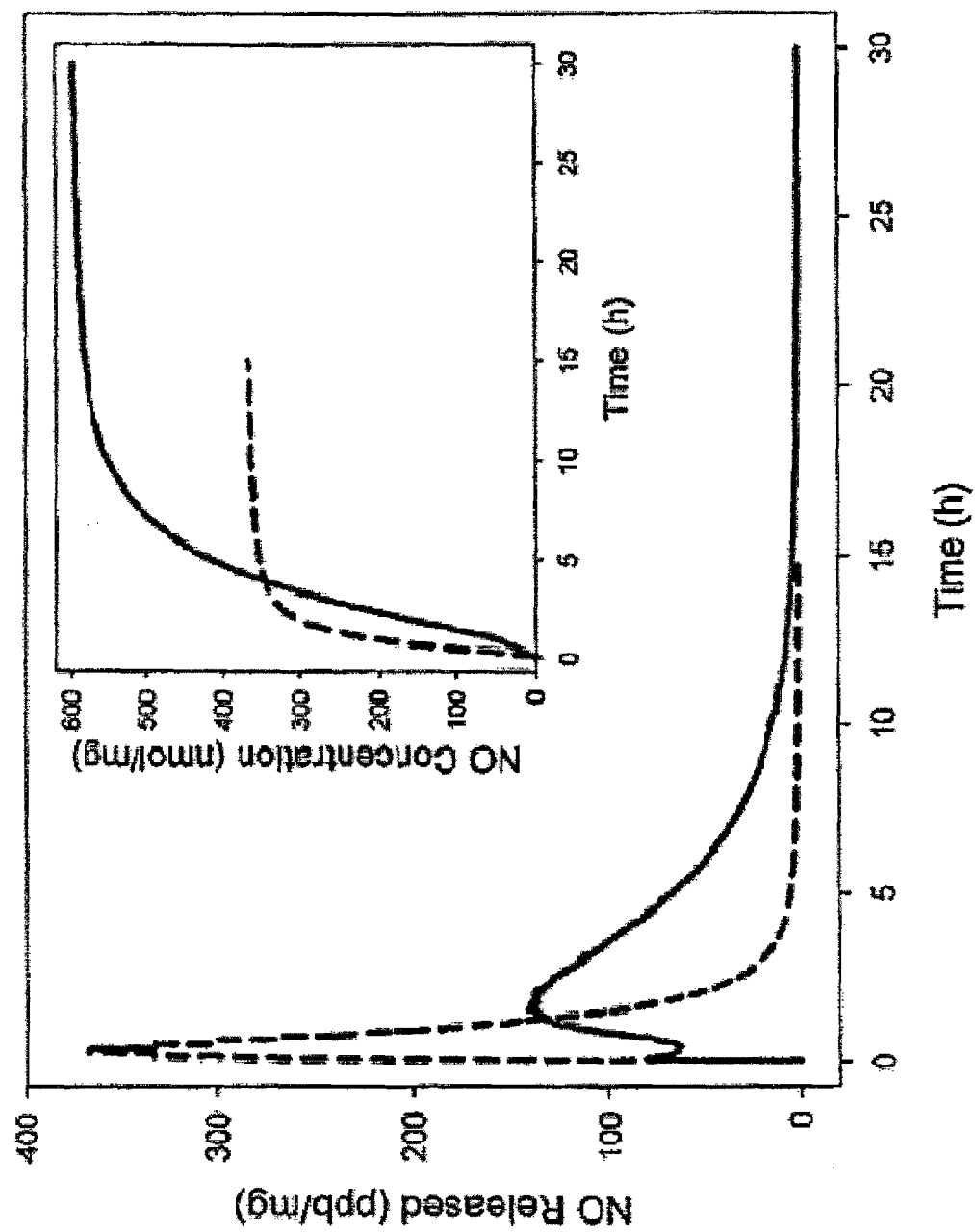
FIG. 22 is a NO-release profile of NO release from co-condensed silica containing 10 mol % AHAP3 (dashed line) and 17 mol % AEAP3 (solid line). The inset shows a plot of total NO-release over time of the same two silica types.

The NO release was measured in phosphate buffered saline (PBS) solution at physiological temperature (37° C.) and pH (7.4) using a chemiluminescence nitric oxide analyzer. See Beckman, J. S., and Conger, K. A., *Methods Companion Methods Enzymol.*, 7, 35-39 (1995). The NO release profiles of two representative silica nanoparticles (10 and 17 mol % of AHAP3 and AEAP3, respectively, balance TEOS) are compared in FIG. 22. Notably, the NO "payload" and release rates were significantly affected by both the concentration and chemical structure of the amine ligands used to prepare the silica nanoparticles. Of the four aminoalkoxysilane systems studied (e.g., AEAP3, AHAP3, AEMP3, and DET3), AEAP3 silica released the largest overall amount of NO. Increasing the mol % of AEAP3 from 10 to 17 mol % led to a corresponding increase in both t[NO] and [NO]$_m$ (145 to 600 nmol/mg and 14 to 140 ppb/mg, respectively). However, both the $t_{1/2}$ and $t_m$ decreased with increasing aminoalkoxysilane concentration (12 to 3.4 h and 8.0 to 2.1 h for 10 to 17 mol % AEAP3, respectively). Significant levels of NO continued to be released for up to 30 h, albeit at a lesser rate for both 10 and 17 mol % AEAP3.

One possibility is that such NO release behavior can be attributed to the size of the particle. The diameter and surface areas of calculated for some of the presently described particles are shown below in Table 5. As the diameter of the particle decreases for a given aminoalkoxysilane (by increasing the aminoalkoxysilane concentration), a smaller water diffusion distance to interior NO donor ligands is expected. As such, the NO release becomes more rapid since N-diazeniumdiolate decomposition to NO is a function of water uptake. Notably, the NO release properties of these silica particles deviates from those of small molecule N-diazeniumdiolates and NO-releasing silica prepared by surface grafting. Indeed, $t_{1/2}$ of the AHAP3 silica was found to be 0.85 h, longer than $t_{1/2}$ of 0.05 and 0.72 h for analogues small molecule DMHD/NO and the surface-grafted silica NO donors prepared with N-(6-aminohexyl)-3-aminopropyltrimethoxysilane (see Zhang, H., et al., *J. Am. Chem. Soc.*, 125, 5015-5024 (2003)), respectively, prepared using similar amine precursors (i.e., aminohexylamino ligands). Likewise, $t_{1/2}$ of the AEAP3-based silica particles prepared via a "one-pot" synthesis was 3.4-12 h, while $t_{1/2}$ of the surface grafted AEAP3 silica (designated 2N[2] in Zhanq, H., et al.) was reported as 2.4 h. See Zhang, H., et al., *J. Am. Chem. Soc.*, 125, 5015-5024 (2003).

TABLE 5

Diameters and Surface Areas of of Silica Particles Prepared based on the Co-condensation of NO Donor Precursors.

| Ligand Type | Mol %$^c$ | $d_{AFM}$ (nm) | $A_{BET}$ (m2/g) |
|---|---|---|---|
| AEP3 | 10 | 500 | 9 |
| AEP3 | 13 | 210 | 10 |
| AEP3 | 17 | 92 | 14 |
| AHAP3 | 10 | 20 | 17 |
| None (control) | 0 | 250 | 500 |

Figure 23:
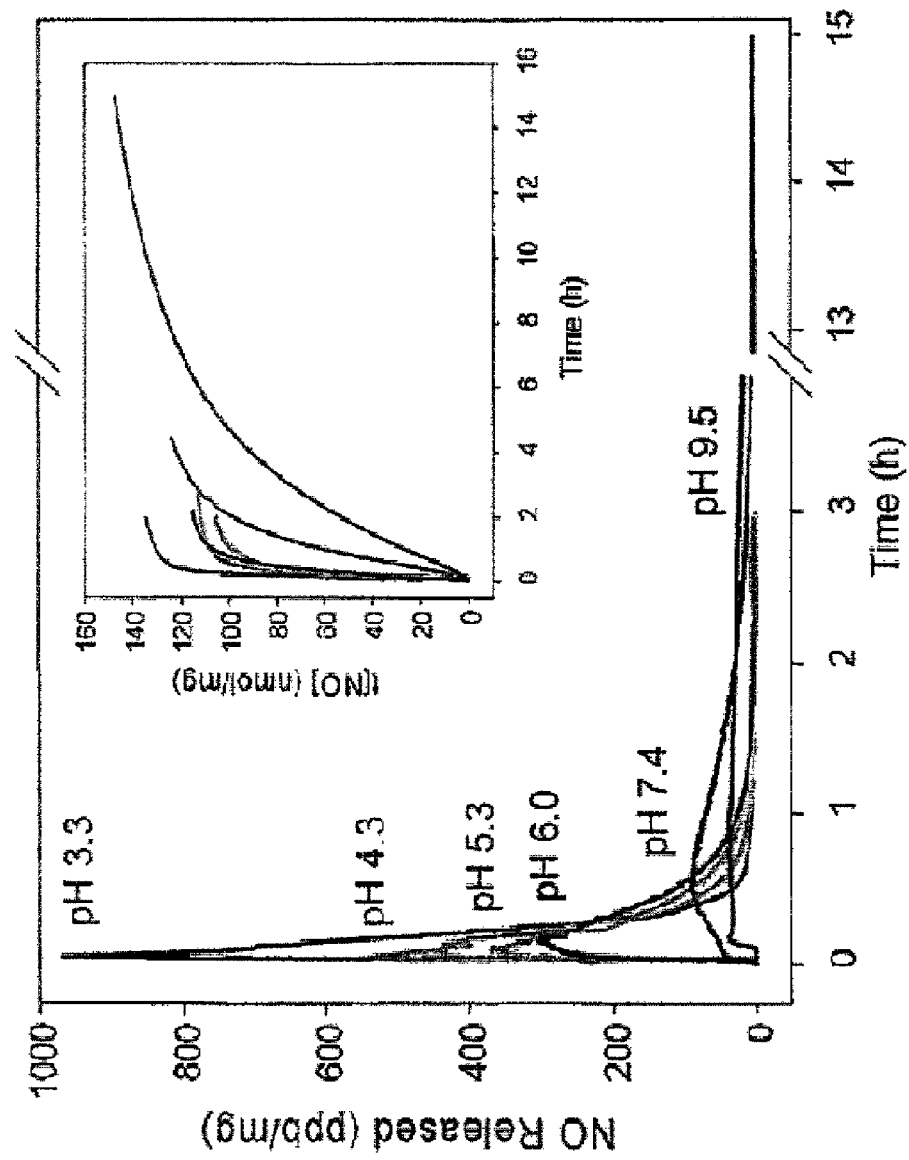
FIG. 23 is a plot of NO release of co-condensed silica nanoparticles containing AEAP3 as a function of pH at 37° C. The inset is a plot of total NO release.

The effect of pH on the, NO release kinetics from the silica scaffolds was also evaluated, as shown in FIG. 23. Consistent with the behavior of small molecule N-diazeniumdiolates (see Davies K. M., et al., *J. Am. Chem. Soc.*, 123, 5473-5481 (2001)), NO release was accelerated under acidic conditions (pH 3.3). Conversely, NO release was slowed considerably at elevated pH (9.5), consequently demonstrating a simple method for storing and transporting NO donor nanoparticles without significant deterioration of the N-diazeniumdiolate. The t[NO] was similar at all pH values, but the NO release kinetics were dramatically increased at lower pH. A nine-fold increase in the maximum flux of NO released ([NOim) was observed at pH 3.3 compared to that at pH 7.4. Such behavior, combined with the pH dependent dissociation of N-diazeniumdiolates seems to confirm that the dominant mechanism of NO release for the silica scaffolds is proton initiated.

Example 14

Figure 24A:
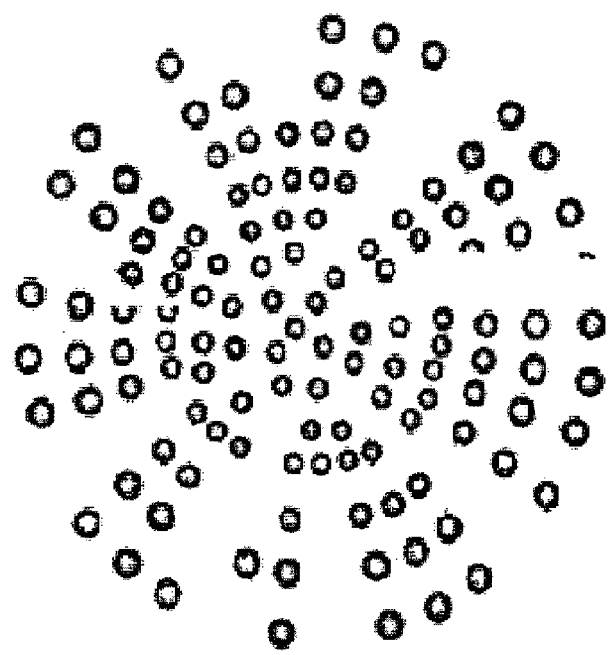
FIG. 24A is a schematic representation showing a cross section of a mesoporous NO-releasing silica particle prepared by a templated synthesis using the surfactant cetyltrimethyl ammonium bromide (CTAB) as a template. The shaded area represents co-condensed silica network, while the small shaded circles represent NO-donors in the co-condensed silica network. The unshaded area represents pores in the particle formed from the removal of the CTAB template after the silane condensation reaction.

Use of CTAB as a Template in the Synthesis of NO-Releasing Mesoporous AEAP3-Silica Particles Cetyltrimethyl ammonium bromide (CTAB) was used as a template in the synthesis of mesoporous AEAP3-silica. The mesoporous silica was prepared as described above in Example 10, using 10 mol % AEAP3, Additionally, the AEAP3/TEOS silane solution contained 0.01 M of CTAB. Following condensation of the silane mixture, the particles were treated with 1M HCl in EtOH at 75° C. for 24 h to remove the CTAB. A schematic representation showing a proposed cross-sectional view of a mesoporous NO-releasing silica particle Is shown in FIG. 24A.

Figure 24B:
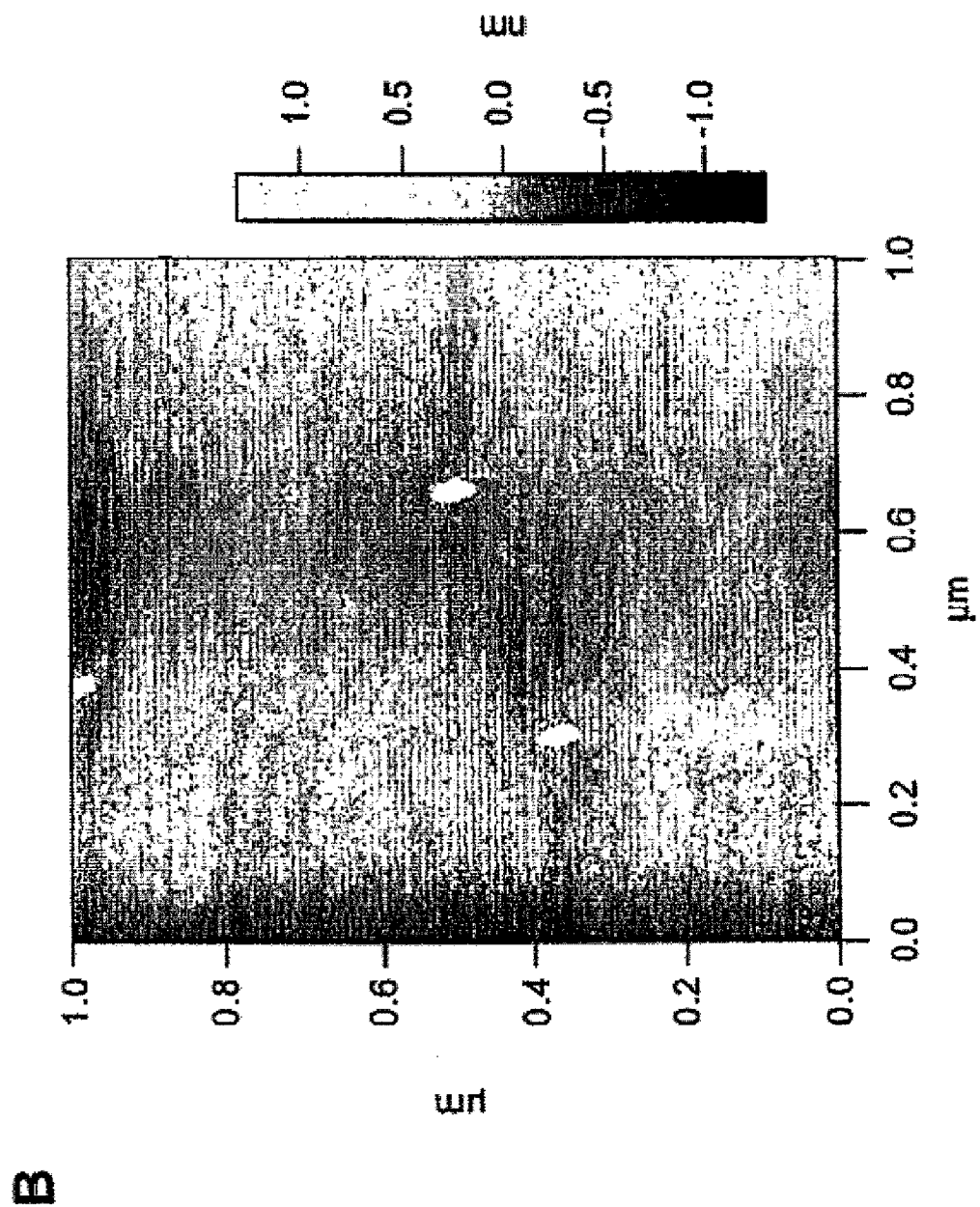
FIG. 24B is a contact mode atomic force microscope (AFM) image of a mesoporous N-(6-aminoethyl)aminopropyltrimethoxysilane (AEAP3)-silica particle prepared using cetyltrimethyl ammonium bromide (CTAB) as a template.
Figure 25:
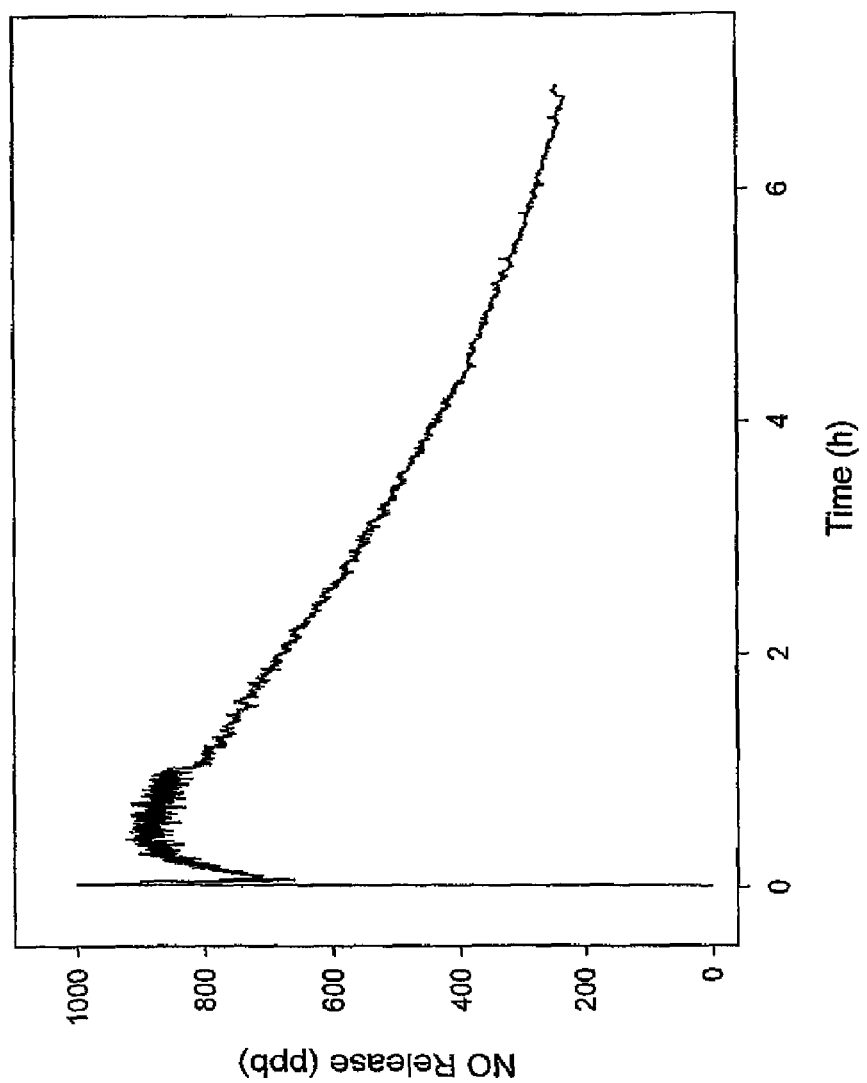
FIG. 25 is a plot showing the nitric oxide release profile of mesoporous N-(6-aminoethyl)aminopropyltrimethoxysilane (AEAP3)-silica (3 mg of particles in phosphate buffer solution (PBS) at 37° C.).

The particles were analyzed using atomic force microscopy as described in Example 11. See FIG. 24B. Nitric oxide release was also measured as described in Example 11. The nitric oxide release (ppb) versus time (hr) for 3 mg of the mesoporous particles in PBS at 37° C. is shown in FIG. 25.

Example 15

Synthesis of Silica Particles Based on Co-Condensation of Pre-Charged NO Donors

Although the NO release levels of the silica nanoparticles prepared from the co-condensation of NO donor precursors (which can also be referred to as a "post-synthesis charging" or simply "post-charging") were significantly greater than small molecule diazeniumdiolates, the aminoalkoxysilane content used to prepare the nanoparticles was limited to <20 mol % due to particle aggregation at higher aminosilane concentrations. Without being bound to any particular theory, it is believed that the aggregation can be attributed to interactions between the amines and adjacent silanols and/or other amines via hydrogen bonding.

To increase the concentration of aminoalkoxysilanes, and thus the NO donor content of the particles, an additional strategy for synthesizing the silica nanoparticles of the presently disclosed subject matter involves the co-condensation of silanes containing diazeniumdiolates. Thus, in contrast to the method described in the Example 10, where the silica nanoparticles were first synthesized and then pressurized ("charged") with the NO gas necessary to form diazeniumdiolate NO donors (which can also be referred to as a "post-synthesis charging" or simply "post-charging"), the diazeniumdiolates can also be formed prior to co-condensation of the silica nanocomposites (i.e., "pre-charging"). See FIG. 5B.

Briefly, an aminoalkoxysilane solution was prepared by dissolving an appropriate amount of aminoalkoxysilane in a mixture of EtOH, MeOH, and NaOMe. The stirring solution was charged with NO (5 atm, 3 d) to form diazeniumdiolate-modified aminoalkoxysilanes. Silane solutions were then prepared by mixing TEOS with different ratios (10-75 mol %, balance TEOS) of diazeniumdiolate-modified aminoalkoxysilane. The silane solution was added into an EtOH solvent in the presence of an ammonia catalyst. The resulting white precipitate was collected by centrifugation, washed with EtOH, dried under ambient conditions, and stored in a sealed container at −20° C. until use. The results suggest that the pre-charging strategy reduces aggregation because the aminoalkoxysilanes are first converted to diazeniumdiolates, thereby avoiding interaction of amine sites during particle formation. As such, the approach can be used to facilitate greater access of NaOMe and NO to the amine precursors resulting in high yields of NO per mol of aminoalkoxysilane precursor.

Example 16

Figure 5:
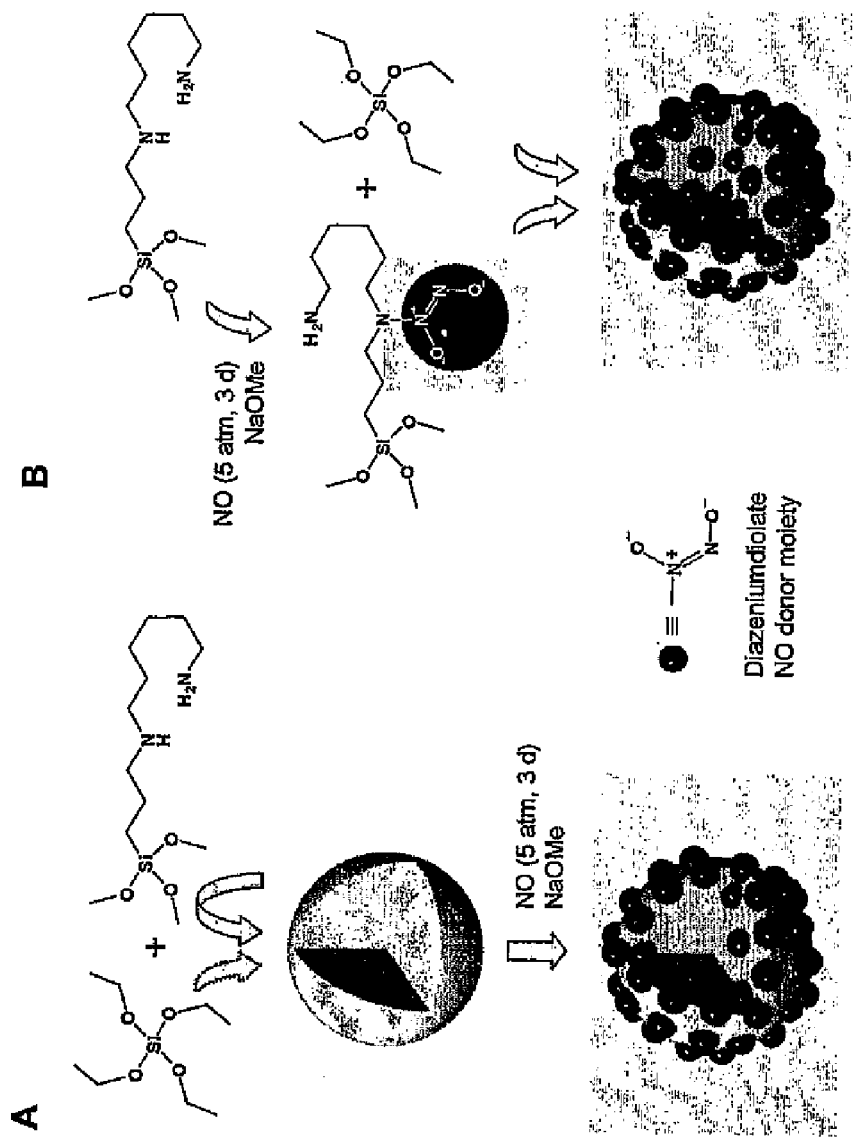
FIG. 5A is a schematic representation of the synthesis of NO-releasing co-condensed silica particles using a "post-charging" method, wherein amino groups from aminoalkoxysilanes are reacted with NO gas after co-condensation in a silica network.
FIG. 5B is a schematic representation of the synthesis of NO-releasing co-condensed silica particles using a "pre-charging" method, wherein aminoalkoxysilanes are reacted with NO gas prior to co-condensation to form a silica network.

NO-Release Properties of Particles Prepared from Co-Condensation of Pre-Charged NO-Donors The NO release properties of diazeniumdiolate-modified silica nanoparticles prepared via the pre-charging approach described in Example 15 are summarized below in Table 6. Notably, both the total NO released (t[NO]) and the maximum amount of NO released ([NO]$_m$) were increased considerably compared to NO releasing-silica prepared by the post-charging method at identical aminoalkoxysilane concentrations (See Table 4). For example, t[NO] and [NO]$_m$ for 17 mol % AEAP3 were increased from 600 to 800 nmol/mg and 140 to 1200 ppb/mg, respectively. Without being bound to any particular theory, the elevated quantities of NO release could be the result of a more homogeneous distribution of the diazeniumdiolate NO donors throughout the silica particle, as shown in FIG. 5B. More importantly, the pre-charging approach allows for an increase in the aminoalkoxysilane content up to 45 mol % without aggregation, resulting in concomitant increases in t[NO] and [NO]$_m$.

Methylaminopropyl-trimethoxysilane (MAP3), an aminoalkoxysilane containing a methyl-terminated secondary amine, was also used to prepare NO-releasing silica particles. By removing primary amines and the potential for hydrogen bonding interactions, particles with MAP3 aminoalkoxysilane concentrations up to 75 mol % and sizes ranging from 80-400 nm can be synthesized depending on the solvent employed during synthesis. Additionally, increasing the mol % of MAP3 from 10 to 75 mol % led to a corresponding increase in the NO release characteristics (e.g., t[NO] increased from 1600 to 10200 nmol/mg). In addition, the NO release of MAP3-based silica particles was characterized by a greater initial NO release burst and shorter overall NO release half-life (33000-177000 ppb/mg and ~5 min, respectively).

TABLE 6

NO Release Properties of Particles Prepared from Pre-Charged NO Donors

| Ligand Type | Mol % | t[NO] (nmol/mg) | t½ (h) | [NO]$_m$ (ppb/mg) | t$_m$ (h) |
|---|---|---|---|---|---|
| AEP3 | 17 | 800 | 1.13 | 1200 | 0.12 |
| AEP3 | 25 | 1200 | 1.45 | 1600 | 0.13 |
| AEP3 | 35 | 1500 | 1.83 | 1400 | 0.13 |
| AEP3 | 45 | 1700 | 2.17 | 1300 | 0.13 |
| AHAP3 | 10 | 600 | 0.25 | 3400 | 0.05 |
| AHAP3 | 25 | 1600 | 0.30 | 9500 | 0.05 |
| AHAP3. | 35 | 2600 | 0.35 | 14500 | 0.08 |
| AHAP3 | 45 | 3800 | 0.27 | 21700 | 0.13 |
| MAP3 | 45 | 1600 | 0.08 | 33000 | 0.05 |
| MAP3 | 55 | 2900 | 0.08 | 60000 | 0.05 |
| MAP3 | 65 | 5800 | 0.08 | 134000 | 0.05 |
| MAP3 | 75 | 10200 | 0.07 | 177000 | 0.05 |

Example 17

Ovarian Cancer Cell Studies

To evaluate the tumoricidal potential of NO donor silica nanoparticles, the cytotoxicity of control and NO-releasing silica particles on immortalized normal (T29) and cancer (A2780 and OVCAR-3) human ovarian epithelial cells was tested. MTT cell viability assays were performed as described below. The 3-(4,5-dimethylthiazol-2-yl-)-2,5-diphenyltetrazoliumbromide (MTT) proliferation assay was employed to determine the relative sensitivities of OVCAR-3 cells to PYRRO/NO. Cells were seeded in 6 replicates at 1–5×10$^3$ cells/well in 96-well microtiter plates, incubated overnight, and exposed to concentrations of NO donor and control pyrrolidine solutions for 48 h. The NO-releasing medium was then removed and replaced by MTT solution, upon which the cells were incubated for an additional 4 h at 37° C. Following removal of the MTT, DMSO was added, and the absorption of the solution was measured at 560 nm using a microplate reader.

Figure 26:
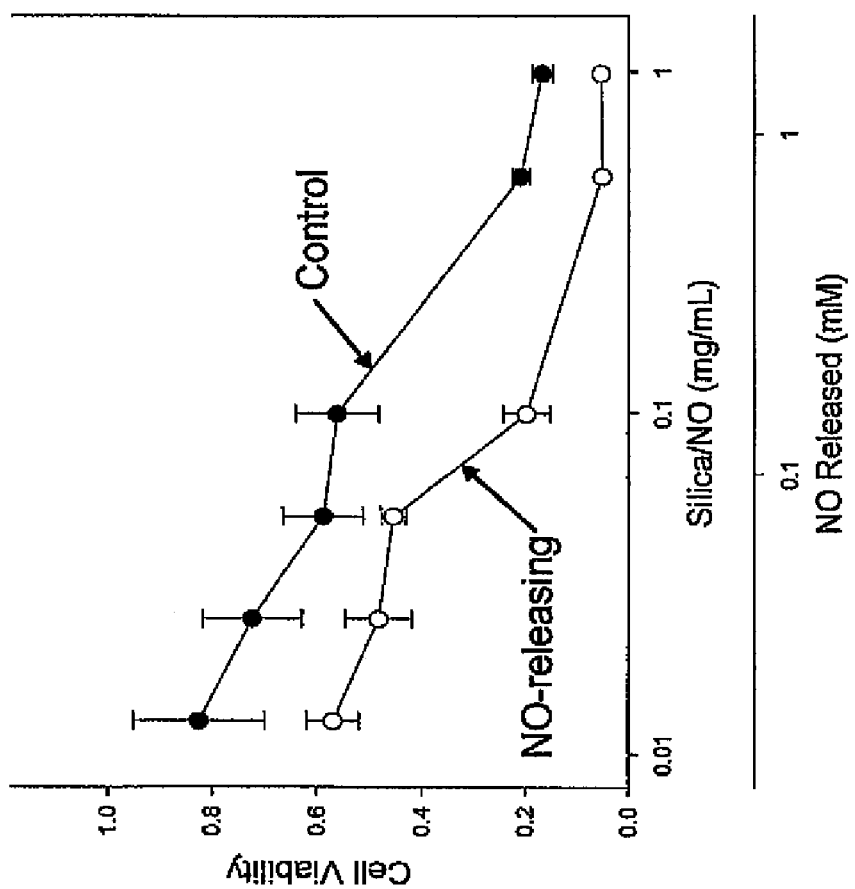
FIG. 26 is a graph of the cytotoxicity of control (dark circles) and NO-releasing silica prepared with 45 mol % AHAP3 (open circles) on ovarian epithelial tumor cells.

As shown in FIG. 26, A2780 ovarian epithelial tumor cells were treated with varying doses of control and NO-releasing AHAP3 silica (0.013-1.0 mg/mL) for 48 h. The viability of the A2780 cells was reduced upon exposure to NO-releasing AHAP3 silica at low doses, and the proliferation of A2780 cells was almost completely inhibited by NO-releasing AHAP3 silica at a dose of 0.50 mg/mL [minimum inhibitory concentration (MIC) at <5% survival; corresponding to 0.75 mM of NO]. In addition, the IC$_{50}$ dose (50% inhibitory concentration) of NO donor AHAP3 silica was 0.02 mg/mL (0.03 mM NO). Notably, the inhibitory concentrations of the NO-releasing silica proved to be significantly lower than those of small molecule NO donors (e.g., MIC and IC$_{50}$ for PYRRO/NO were 4.4 and 2 mM NO, respectively).

Figure 27:
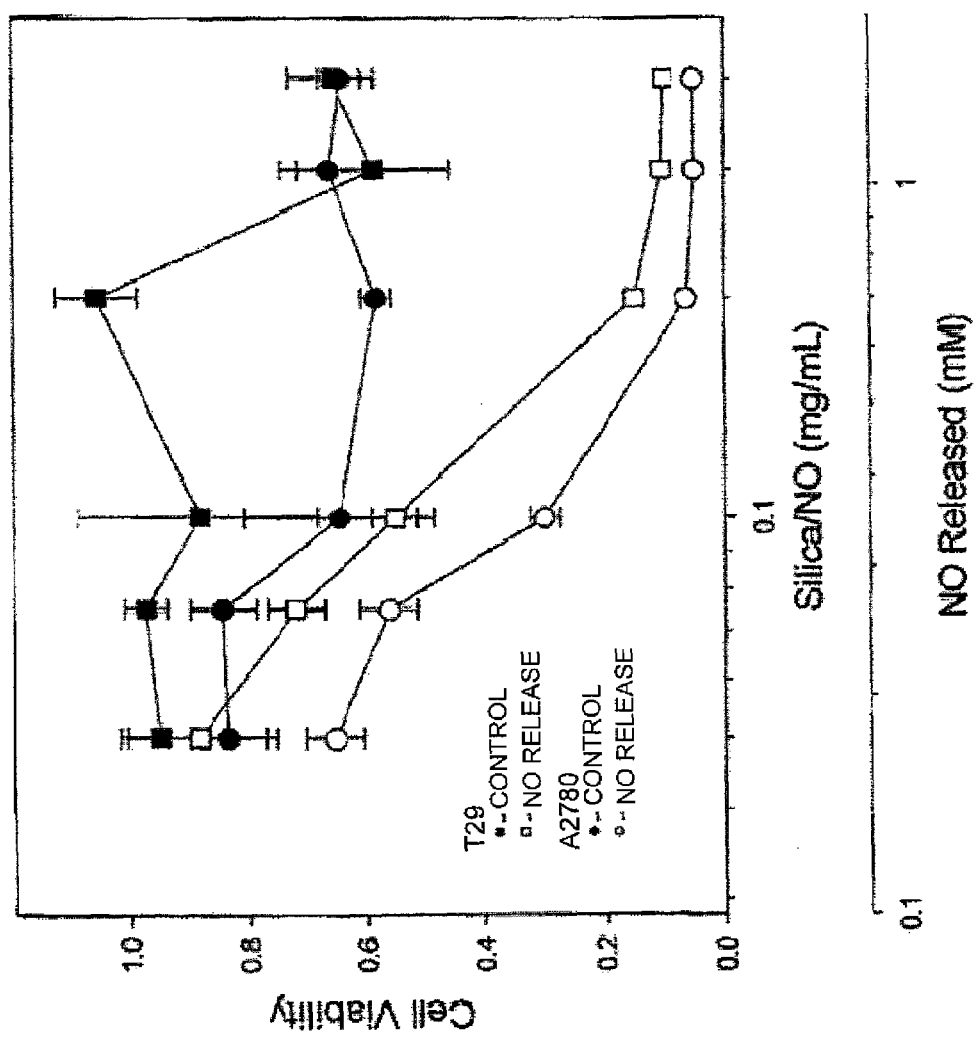
FIG. 27 is a graph showing the cytotoxicity of control (dark squares) and NO-releasing MAP3 co-condensed (open squares) silica nanoparticles on normal (T29, immortalized) cells as well as the cytotoxicity of control (dark circles) and NO-releasing MAP3 co-condensed (open circles) silica nanoparticles on tumor (A2780) cells.

Control silica nanoparticles also exhibited cytotoxic effects against the tumor cells (IC$_{50}$=0.12 mg/mL), albeit less than that of their NO releasing counterparts. Without being bound to any particular theory, the undesirable cytotoxicity of control vehicles could be the result of free primary amines on the surface of the silica structures, as such groups have known cytotoxic properties. See Shi, X., et al., *Colloids Surf. A*, 272, 139-150 (2006). To reduce the cytotoxicity of control and NO-releasing nanoparticles with primary amines, the MAP3 aminosilane (containing only secondary amines) was employed to create more biocompatible vehicles. As expected, the cytotoxicity of MAP3 controls against the immortalized (T29) and tumor (A2780) cells was low, whereas NO-releasing MAP3 silica exhibited cytotoxicity against both T29 and A2780 cells. See FIG. 27. OVCAR-3 ovarian adenocarcinoma cells also showed similar cytotoxic trends with increasing concentrations of NO-releasing silica nanoparticles.

Figure 28:
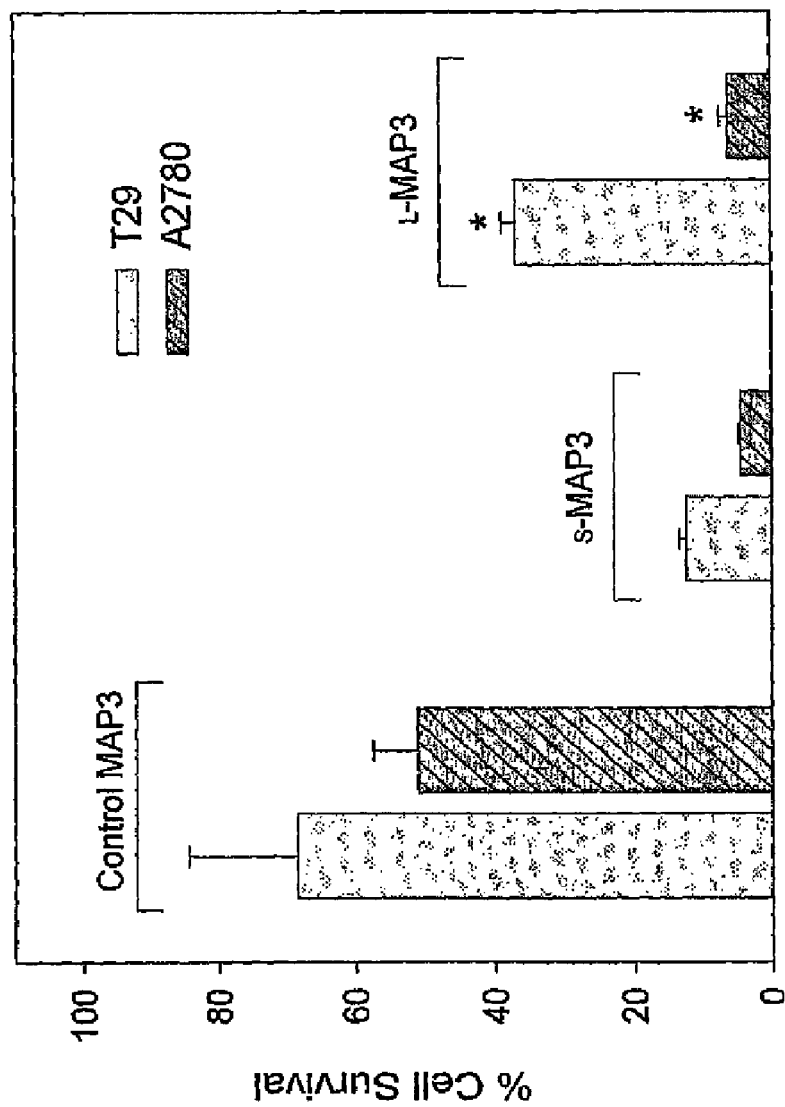
FIG. 28 is a bar graph showing the effect of silica particle size (75 mol % MAP3, balance TEOS) on cytotoxicity against normal T29 (shaded bars) and tumor A2780 (striped bars) cell lines. P<0.001 compared with control MAP3-treated group. Control MAP3 silica (indicated by the brackets) are non NO-releasing and have a diameter of 80 nm, S-MP3 silica has a diameter of 80 nm, L-MAP3 silica has a diameter of 350 nm.

To investigate whether nanoparticle size affects cytotoxicity, two silica nanoparticles (75 mol % MAP3, balance TEOS) of different particle size (80 and 350 nm in diameter, hereafter referred to as s-MAP3 and L-MAP3, respectively) were synthesized. Silica diameter is easily tunable by varying the solvent system (e.g., alcohol) during the sol-gel process. See Harris, M. T. et al., *J. Non-Cryst. Solids*, 121, 397-403 (1990). Increasing the molecular weight (MW) of the alcohol used during synthesis led to a corresponding increase in the particle size (e.g., 100% (v/v) ethanol and 50/50% (v/v) ethanol/butanol mixture were used to prepare s-MAP3 and L-MAP3, respectively). Cell viability was determined by incubating T29 and A2780 with non NO-releasing control MAP3 particle (80 nm), s-MAP3, or L-MAP3 (0.4 mg/mL) for 48 h. See FIG. 28. Notably, the small diameter NO-releasing silica (s-MAP3) proved cytotoxic against both immortalized (T29) and cancer (A2780) cells (12±1.1 and 5±0.2% survival, respectively). In contrast, the larger NO-releasing silica (L-MAP3) was significantly more cytotoxic towards the tumor cells than healthy cells (37±2.0 versus 6±1.2% survival for T29 and A2780, respectively). The reduced toxicity of the larger NO delivery vehicles against T29 cells represents a major step toward the development of nanodevices capable of releasing tumoricidal concentrations of NO with minimal effect on healthy cells.

Example 18

Cellular Uptake

The cellular uptake of NO-releasing silica particles was studied using confocal fluorescence microscopy. Briefly, A2780 ovarian cancer cells were plated to ~20% confluency on MET-TEC® glass bottom microscopy plates and incubated overnight. Prior to imaging, the Incubation buffer was discarded and replaced with Krebs-Henseleit imaging buffer [10 mM N2-hydroxyethylpiperazine-$N^1$-2-ethanesulfonic acid (HEPES), pH 7.4] containing 100 nM tetramethylrhodamine dye (TMRM) to selectively stain the mitochondria of the A2780 cancer cells (30 min incubation). The NO-releasing silica nanoparticles were fluorescently labeled via the co-condensation of three silane precursors: fluorescein isothiocyanate (FITC)-modified aminopropyl-trimethoxysilane (APTMS), diazeniumdiolated MAP3, and TEOS.

Figure 29:
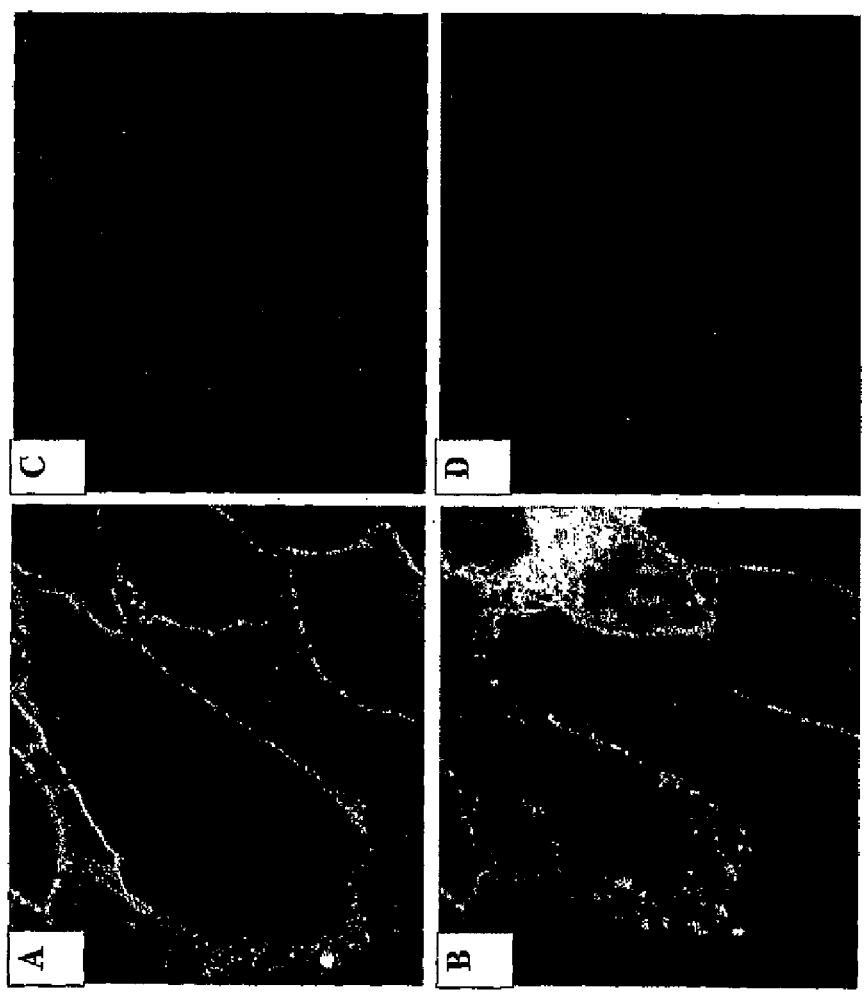
FIG. 29A is a laser spanning microscope image of A2780 ovarian cancer cells taken at 5 min after incubation with FITC-labeled MAP3 silica nanoparticles.
FIG. 29B is a laser scanning microscope image of A2780 ovarian cancer cells taken at 60 min after incubation with FITC-labeled MAP3 silica nanoparticies.
FIG. 29C is a laser scanning microscope image of A2780 ovarian cancer cells taken at 5 min after incubation with 100 nm tetramethylrhodamine (TMRM) mitochondrial stain.
FIG. 29D is a laser scanning microscope image of A2780 ovarian cancer cells taken at 60 min after incubation with 100 nm tetramethylrhodamine (TMRM) mitochondrial stain.

A Zeiss Laser Scanning Microscope (LSM 510; Carl Zeiss, Inc., Oberkochen, Germany) was used to perform the fluorescence measurements. The red fluorescence of TMRM (helium-neon laser excitation at 543 nm) was monitored at 5 min and at 60 min to provide a map of the intracellular location of mitochondria and an outline of A2780 nuclei. See FIGS. 29C and 29D. A 100-μL aliquot of FITC-labeled NO-releasing MAP3 silica nanoparticles dissolved in the imaging buffer was added directly to the cells on the stage of the microscope, yielding a nanoparticle concentration of 0.1 mg/mL. Immediately, the green fluorescence of the FITC-labeled silica nanoparticles (argon laser excitation at 488 nm) was observed at 520 nm, resulting in the outline of the A2780 cancer cells. Confocal images were collected at 5 min intervals to monitor the cellular uptake of the green fluorescent nanoparticles, FIG. 29A shows the cells after 5 min incubation with the FITC labeled MAPS silica particles. After 1 h, substantial intracellular accumulation of nanoparticles was observed. See FIG. 29B. Additionally, the red fluorescence characteristic of mitochondria! viability was absent in a number of cells after 60 min (see FIG. 29D), and the cells appeared to be shrinking in size, indicating cell death.

Example 19

Antimicrobial Activity Studies

Figure 30:
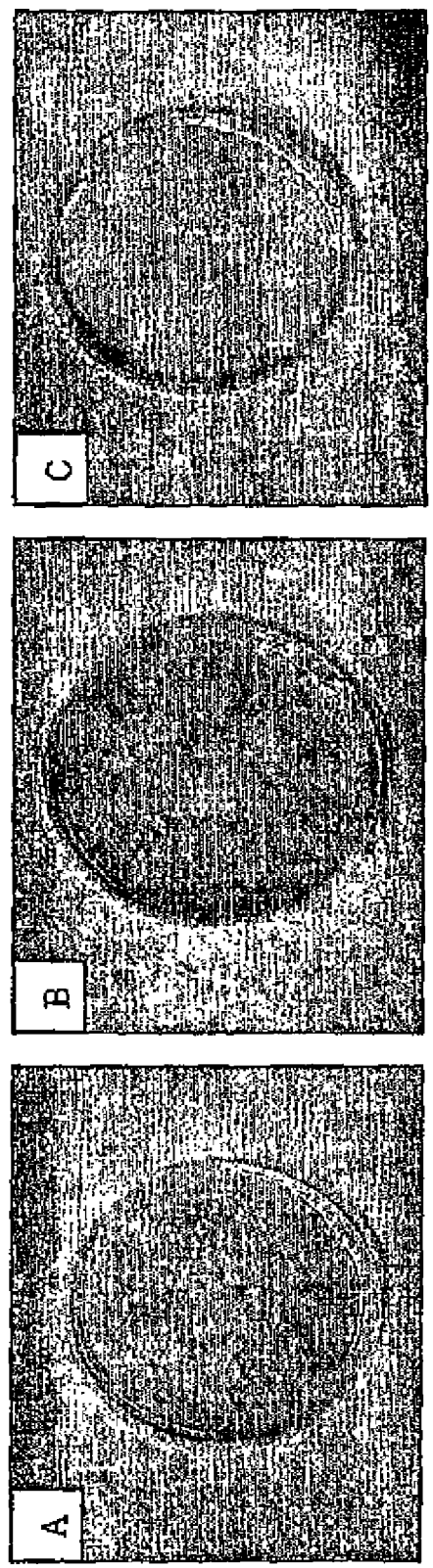
FIG. 30A is a photograph showing colonies of *P. aeruginosa* that formed on nutrient agar plates after incubation with sterile phosphate buffered solution (PBS) at 37° C.
FIG. 30B is a photograph showing colonies of *P. aeruginosa* that formed on nutrient agar plates after incubation with control (non NO-releasing) AEAP3 silica nanoparticles at 37° C.
FIG. 30C is a photograph showing colonies of *P. aeruginosa* that formed on nutrient agar plates after incubation with NO-releasing 45 mol % AEAP3 silica nanoparticles at 37° C.

*Pseudomonas aeruginosa* (ATCC #19143, from American Type Culture Collection Company, Manassas, Va., United States of America), a gram-negative opportunistic pathogen was cultured in tryptic soy broth (TSB) to an optical density ($OD_{\lambda=600\ nm}$) of approximately 0.2 (corresponding to ~1.0× $10^8$ colony forming units [CFU]/mL, confirmed by serial dilutions). After pelleting the bacteria by centrifugation, the TSB culture media was discarded and the bacteria were resuspended in sterile phosphate buffered saline (PBS, pH 7.4). The concentration of bacteria was adjusted to $10^3$ CFU/mL by serial 10-fold dilutions in PBS. Portions of this bacterial suspension (200 μL) were dispensed into sterile micropipette vials, and 200 μL of either NO-releasing 45 mol % AEAP3 silica nanoparticles (1 mg/mL), control (non NO-releasing) AEAP3 silica nanoparticles (1 mg/mL) or sterile PBS (blank) were added to each vial. After incubation at 37° C. for 1 h, 100 μL of each suspension was plated onto tryptic soy agar nutrient plates, which were incubated at 37° C. overnight. The following day, colonies of bacteria that formed on each plate were counted and photographs of representative nutrient plates were taken. As shown in FIG. 30, nitric oxide release from silica nanoparticles resulted in a drastic reduction in the number of viable bacteria cells (FIG. 30C), as compared to blank (FIG. 30A) and control (non NO-releasing) silica nanoparticles (FIG. 30B). Quantitatively, approximately the same number (~360) of colonies formed on the plates representing blank and control suspensions. Only 9 colonies formed from the suspension to which NO-releasing silica nanoparticles were added. This represents a 98% decrease in the number of viable bacteria cells between suspensions to which NO-releasing nanoparticles were added compared to blank and control suspensions.

Figure 31:
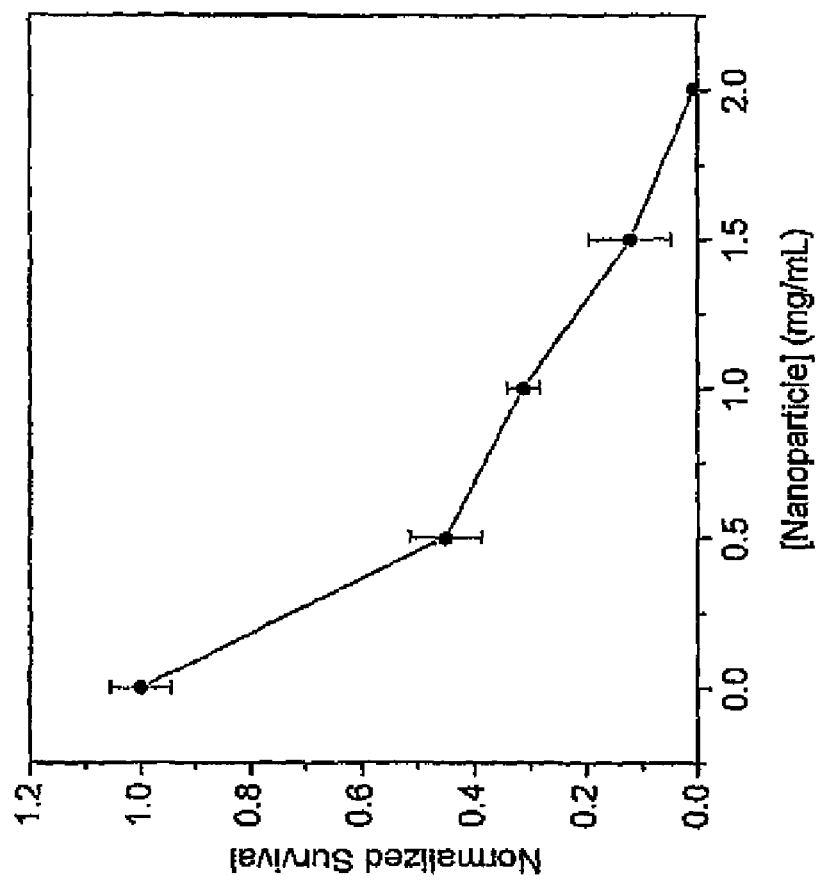
FIG. 31 is a plot showing the in vitro bactericidal activity of NO-releasing silica nanoparticles (45 mol % AEAP3, balance TEOS) against *P. aeruginosa* as a function of nanoparticle concentration.

To more quantitatively evaluate antimicrobial activity of NO-releasing silica nanoparticles, the concentration of bacteria was adjusted to 103 CPU/mL by serial dilutions in PBS and cultures were exposed either to control (non NO-releasing) silica nanoparticles, NO-releasing silica nanoparticles, or sterile PBS (blank). After incubation for 1 h at 37° C., 100 pL of each suspension was plated onto tryptic soy agar nutrient plates and were incubated overnight. As shown in FIG. 31, NO release from silica nanoparticles resulted in a drastic reduction in the number of viable bacteria cells. At a concentration of 2 mg/mL, NO-releasing nanoparticles had a significant increase in bactericidal activity over controls ($p=9.5\times 10^{-4}$). The quantity of NO released during the 1 h incubation period was approximately 1 μmol of NO as determined via chemiluminescence. The silica nanoparticles presented herein thus exhibit in vitro bactericidal activity and represent a vehicle for delivering concentrations of NO for killing microorganisms relevant to infected wounds.

Example 20

Synthesis of NO-Releasing Magnetic Silica Nanoparticles

Figure 32:
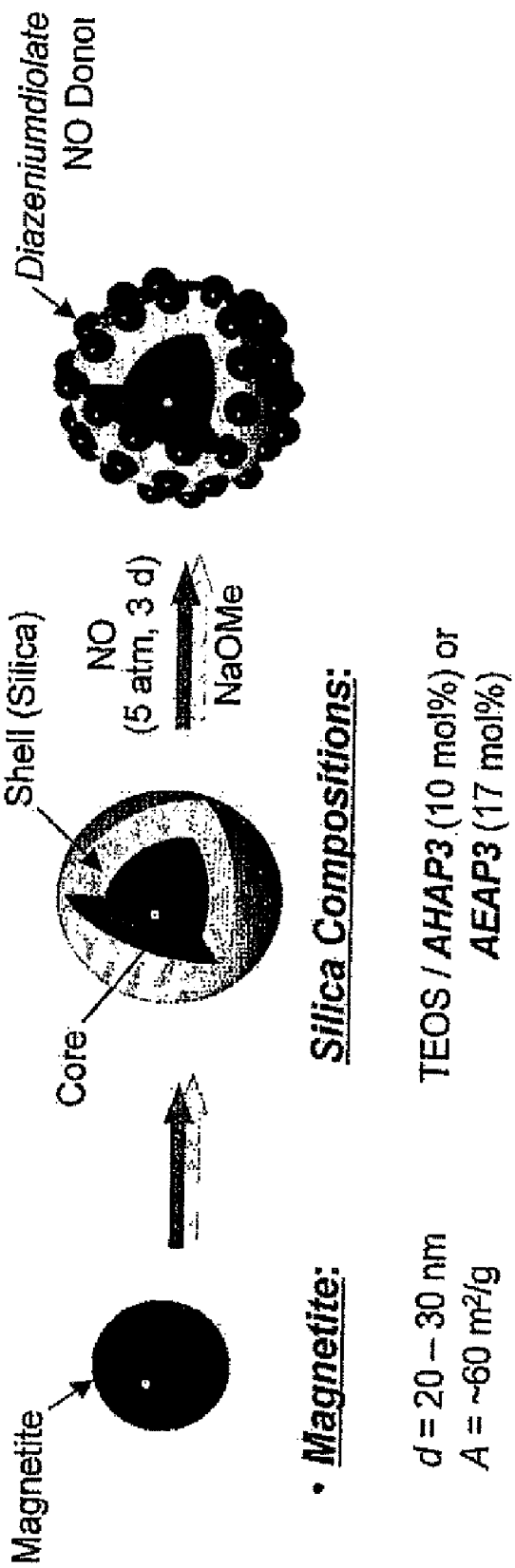
FIG. 32 is a schematic representation of the synthesis of a NO-releasing nanoparticle having a magnetite core covered by a layer of co-condensed silica containing amine groups that can form NO-donors.

Magnetic NO-releasing silica nanoparticles were prepared according to the synthesis shown in FIG. 32. In short, the method of Example 10 was adapted by the inclusion of magnetite ($Fe_3O_4$) particles having diameters of between about 20 nm and 30 nm in a solution containing TEOS and either 10 mol % AHAP3 or 17 mol % AEAP3. Upon co-condensation of the silanes, the magnetite particles were covered with a shell of silica. The particles were then subjected to NO to form diazeniumdiolates.

Figure 33:
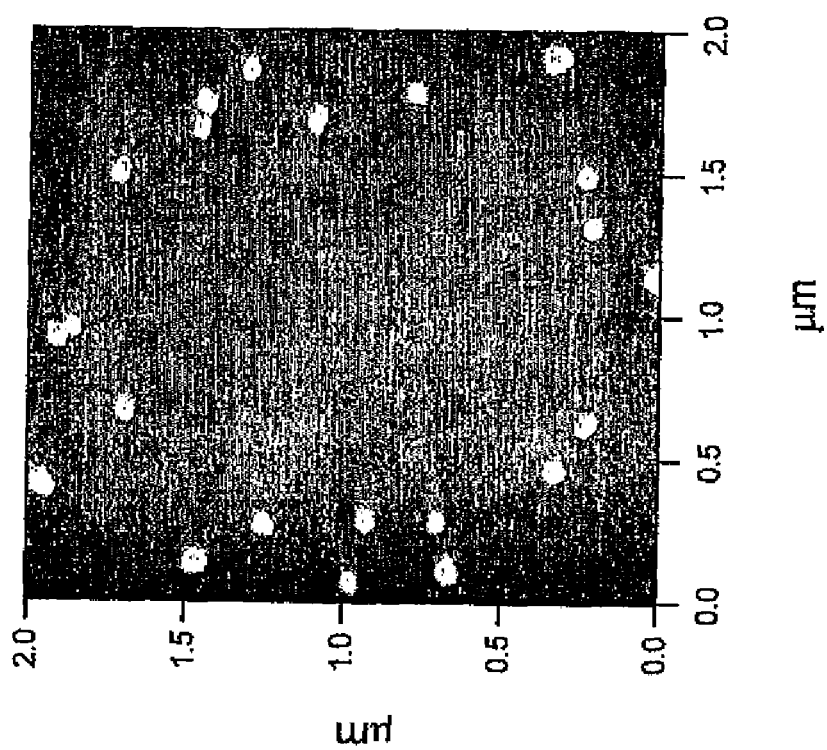
FIG. 33 is an atomic force microscope (AFM) image of magnetite/N-(6-aminohexypaminopropyltrimethoxysilane (AHAP3, 10 mol %)-functionalized silica particles.
Figure 34:
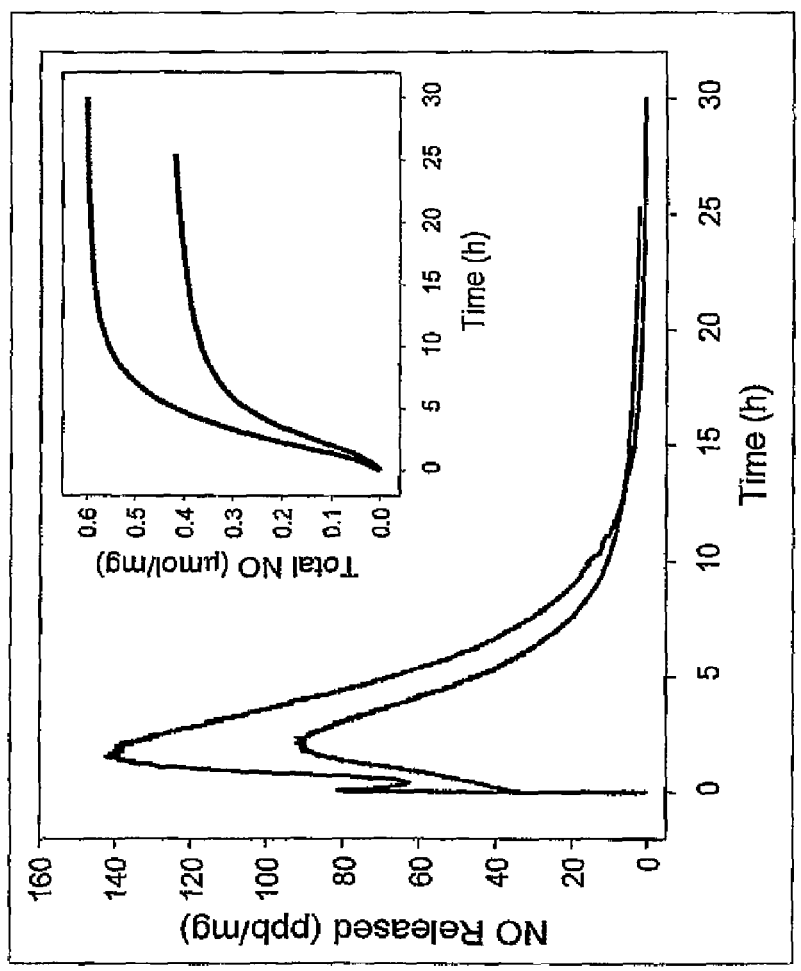
FIG. 34 is a graph showing the NO release profile of magnetite/silica core particles (lower line) compared to the NO-release profile of particles having cores of the same silica composition without magnetite (upper line). The inset is a graph of total NO release.

Atomic force microscopy (AFM) images of the magnetite/silica-AHAP3 particles are shown in FIG. 33. The diameter of the particles was measured as 85±11 nm. The NO-release profiles of the particles are shown in FIG. 34. Experiments with PBS solutions containing the magnetite/silica particles indicate that the application of a magnet can control particle movement.

Example 21

Polyurethane Films Containing NO-Releasing Silica Nanoparticles

NO-releasing silica nanoparticles were incorporated into polyurethane films prepared by adding between about 3 mg to about 18 mg of NO-releasing particle to polymer precursor solutions containing 10 mg of 1:1 (w/w) TECOFLEX® polyurethane (TPU)/hydrophilic polyurethane (HPU) in 500 1.1 .L of THE and ethanol prior to polymerization.

The film prepared by adding 6 mg of nanoparticle to the polymer precursor solution was tested to determine its ability to resist bacterial adhesion as previously described. See Marxer, S. M., et al., *Chem. Mater.*, 15, 4193-4199 (2003). The films were pre-treated to initiate steady NO release and subsequently immersed in a cell suspension containing *Pseudamonas aeruginosa* (ATCC #19143, from American Type Culture Collection Company, Manassas, Va., United States of America), at 37° C. for 30 min. The film surface was then rinsed with water and fixed in a 2% glutaraldehyde solution for 15 min. images of the surfaces were obtained using phase contrast microscopy using a Zeiss Axiovert 200 inverted microscope (Carl Ziess Optical, Chester, Va., United States of America). Phase contrast optical micrographs of control films and the NO-releasing particle-containing film are shown in FIGS. 35A and 35B.

Example 22

Glucose Sensor With An NO-Releasing Layer

Glucose oxidase-based glucose biosensors can detect blood glucose through the electrooxidation of hydrogen peroxide generated by the glucose oxidase (GOx)-catalyzed reaction of glucose and oxygen. As shown schematically in FIG. 36, a glucose sensor was prepared having a NO-releasing layer, Sensor 3600 provides four layers stacked upon a Pt electrode 3602 inner-most layer 3604 was formed from the condensation of a solution containing 25 µL MTMOS, 6 mg of glucose oxidase (GOx), 100 µL EtOH, and 50 µL $H_2O$. Covering GOx layer 3604 is a protective layer 3606 prepared from the polymerization of a 1:1 (w/w) mixture of hydrophobic TECOFLEX® polyurethane (TPU) and hydrophilic polyurethane (HPU) precursors (i.e., a TPU/HPU blend). NO-releasing layer 3608 was prepared from the polymerization of a solution containing 10 mg TPU/HPU and 6 mg of diazeniumdiolate modified silica nanoparticles in 500 µL of THF/EtOH. NO-releasing layer 3608 is further surmounted with a TPU/HPU barrier layer 3610 prepared from a mixture of 10 mg TPU/HPU in 500 µL THF/EtOH.

Figure 36:
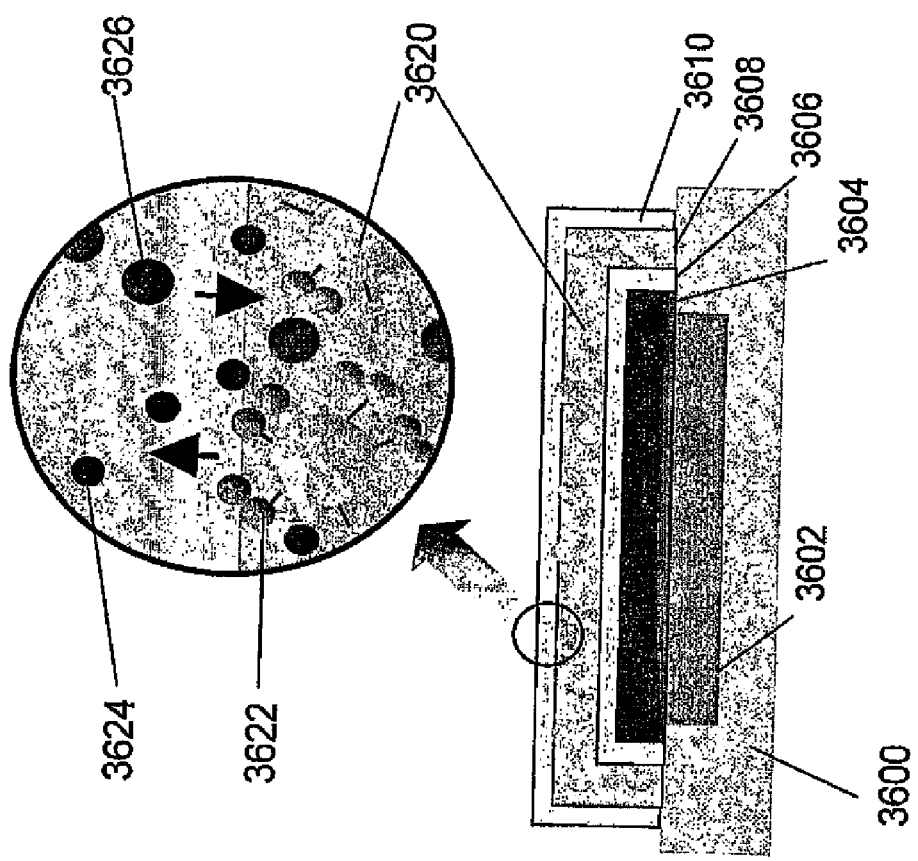
FIG. 36 is a schematic representation of the structure for a Pt electrode of a glucose sensor having a NO-releasing layer formed from a polymeric film comprising NO-releasing co-condensed silica nanoparticles.

Continuing with FIG. 36, the inset shows the interactions at the interface of NO-releasing layer 3608 and outer protecting layer 3610, wherein NO-releasing silica particles 3620 having diazeniumdiolate groups 3622 release nitric oxide 3624 while glucose molecules 3626 are absorbed into NO-releasing layer 3608 on their way to GOx-containing layer 3604.

To evaluate the response of glucose sensor having NO-releasing layers, two control electrodes were also prepared: a control sensor having only a protecting layer and a GOx layer, and a sensor containing all four layers only prepared with silica nanoparticles that did not contain NO-donors. The sensitivity of the various sensors was evaluated in PBS (0.05 M, pH 7.4) using an' applied potential of +7 V vs. Ag/AgCl. The sensitivity of the control, two-layer sensor was determined as 54.5 nA/mM (r=0.9980), that of the four-layer sensor with non NO-releasing silica nanoparticles was 61.3 nA/mM (r=0.9938) and that of the sensor with the NO-releasing layer was 57.9 nA/mM (r=0.9989). These results indicate that the NO-release does not interfere with GOx-based glucose sensing.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

Albert, K., and Bayer, E. J., *J. Chromatogr.*, 544, 345-370 (1991).
Albina, J. E., and Reichner, J. S., *Canc. Metas. Rev.*, 17, 19-53 (1998).
Anwander, R., et al., *Stud. Surf. Sci. Catal.*, 117, 135-142 (1998).
Baker, J. R., Jr., *Biomacromolecules*, 5, 2269-2274 (2004).
Beckman, J. S., and Conger, K. A., *Methods Companion Methods Enzymol.*, 7, 35-39 (1995).
Brannon-Peppas, L. and Blanchette, J. O., *Advanced Drug Delivery Reviews*, 56, 1649-1659 (2004).
Bruch, M. D., and Fatunmbi, H O., *J. Chromatogr, A.*, 1021, 61-71 (2003).
Brust, M., *J. of the Chem. Soc., Chem. Comm.*, 801-802 (1994).
Capala, J., et al., *Bioconjugate Chem.*, 7(1), 7-15 (1996).
Cobbs, C. S., et al., *Cancer Res.*, 55, 727-730 (1995).
Davies, K. M., et al., *J. Am. Chem. Soc.*, 123, 5473-5481 (2001).
Diodati, J. G., et al., *Thrombosis and Haemostasis*, 70, 654-658 (1993).
Feldheim, D. L. and Foss, C. A., eds, *Metal Nanoparticles—Synthesis Characterization, and Applications.* Marcel Dekker, Inc: New York, p. 360 (2000).
Freireich et al., *Cancer Chemother Rep.* 50, 219-244 (1966).
Frost, M. C., et al., *Biomaterials*, 26, 1685-1693 (2005).
Harris, M. T., et al., *J. Non-Cryst. Solids*, 121, 397-403 (1990).
Hatton, B., et al., *Acc. Chem. Res.*, 38, 305-312 (2005).
Hostetler, M. I., et al., *Langmuir*, 15, 3782-3789 (1999).
Hostetler, M. I., et al., *Langmuir*, 14, 17-30 (1998).
Hrabie, J. A., et al., *J. Org. Chem.*, 58, 1472-1476 (1993).
Hrabie, J. A. and Keefer, L. K., *Chem. Rev.*, 102, 1135-1154 (2002).
Huh, S., et al., *Chem. Mater.*, 15, 4247-4256 (2003).
Ignarro, L J., *Nitric Oxide: Biology and Pathobiology*; Academic Press: San Diego (2000).
Ignarro, L. J. et al., *Proc. Natl. Acad. Sci., USA.*, 84, 9265-9269 (1987).
Jenkins, D. C., et al., *Proc. Natl. Acad. Sci., USA.*, 92, 4392-4396 (1995).
Keefer, L. K., *Annu. Rev. Pharmacol. Toxicol.*, 43, 585-607 (2003).
Keefer, L. K., *Chemtech*, 28, 30-35 (1998).
Lai, C.-Y., et al., *J. Am. Chem. Soc.*, 125, 4451-4459 (2003).
Lim, M. H., and Stein, A., *Chem. Mater.*, 11, 3285-3295 (1999).
Lin, H.-P., and Mou, C-Y., *Acc. Chem. Res.*, 35, 927-935 (2002).
Marietta, M. A., et al., *BioFactors*, 2, 219-225 (1990).
Marxer, S. M., et al., *Chem. Mater.*, 15, 4193-4199 (2003).
Munoz, B., at al., *Chem. Mater.*, 15, 500-503 (2003).
Nablo, B. J., et al., *J. Am, Chem. Soc.*, 123, 9712-9713 (2001).
Napoli, C. and Ignarro, L. J., *Annu. Rev. Pharmacol. Toxicol.*, 43, 97-123 (2003).
Penault-Llorca, F., et al., *Int. J. Cancer*, 61(2), 170-176 (1995).
Press, M. F., et al., *Oncogene* 5(7), 953-962 (1990).
Radomski, M. W., et al., *Br. J. of Pharmacology*, 101, 145-749 (1992).

Radu, D. R., et al., *J. Am. Chem. Soc.*, 126, 1640-1641 (2004).

Roy, I., et al., *Proc. Natl. Acad Sci, USA.*, 102, 279-284 (2005).

Sayari, A., and Hamoudi, S., *Chem. Mater.*, 13, 3151-3168 (2001).

Shi, X., et al., *Colloids Surf. A.*, 272, 139-150 (2006).

Stein, A., et al., *Adv. Mater.*, 12, 1403-1419 (2000).

Thomsen, L. L., et al., *Br, J. Cancer.*, 72, 41-44 (1995).

Trewyn, B. G., et al., *Nano. Lett.*, 4, 2139-2143 (2004).

Troughton, B. B., et al., *Langmuir,* 4, 365-385 (1988).

Wang, P. G., et al., *Nitric Oxide Donors: For Pharmaceutical and Biological Applications*; Wiley-VCH: Weinheim, Germany (2005).

Wang, P. G., et al., *Chem. Rev.,* 102, 1091-1134 (2002).

Wiener, E. C. et al., *Invest. Radiol.,* 32 (12), 748-754 (1997).

Wiener, E. C., et al., *Magn. Reson. Med.* 31(1), 1-8 (1994).

Yoshitake, H., *New. J. Chem.*, 29, 1107-1117 (2005).

Zhang, H., et al., *J. Am. Chem. Soc.,* 125, 5015-5024 (2003).

Zhou, Z., and Meyerhoff, M E., *Biomacromolecules,* 6, 780-789 (2005).

It will be understood that various details of the presently disclosed subject matter can be changed without departing from the scope of the presently disclosed subject matter. Furthermore, the foregoing description is for the purpose of illustration only, and not for the purpose of limitation.

That which is claimed:

1. A nitric oxide-releasing particle, the nitric oxide-releasing particle comprising:
   a co-condensed silica network comprising a nitric oxide donor, wherein the nitric oxide donor is formed prior to condensation of the co-condensed silica network, wherein the co-condensed silica network is synthesized from the condensation of a silane mixture comprising an alkoxysilane and at least one aminoalkoxysilane having an amine substituted by a diazeniumdiolate.

2. The nitric oxide-releasing particle of claim 1, wherein the alkoxysilane comprises a tetraalkoxysilane of the formula $Si(OR)_4$, wherein R is alkyl; and the aminoalkoxysilane has the formula $R''—N(NONO^-X^+)—R'—Si(OR)_3$, wherein R is alkyl, R' is alkylene or aralkylene, R" is alkyl or alkylamine, and $X^+$ is a cation selected from the group consisting of $Na^+$ and $K^+$.

3. The nitric oxide-releasing particle of claim 2, wherein the silane mixture comprises between about 10 mol % to about 99 mol % of the tetraalkoxysilane and about 1 mol % to about 90 mol % of the aminoalkoxysilane having an amine substituted by a diazeniumdiolate.

4. The nitric oxide-releasing particle of claim 3, wherein the silane mixture further comprises about 0 mol % to about 20 mol % of a fluorinated silane; about 0 mol % to about 20 mol % of a cationic or anionic silane; and about 0 mol % to about 20 mol % of an alkylsilane.

5. The nitric oxide-releasing particle of claim 2, wherein the tetraalkoxysilane is selected from the group consisting of tetraniethyl orthosilicate and tetraethyl orthosilicate.

6. The nitric oxide-releasing particle of claim 4, wherein the fluorinated silane is selected from the group consisting of: (heptadecafluoro-1,1,2,2-tetrahydrodecyl)triethoxysilane; (3,3,3-trifluoropropyl)trimethoxysilane; and (perfluoroalkyl)ethyltriethoxysilane.

7. The nitric oxide-releasing particle of claim 4, wherein the cationic or anionic silane is selected from the group consisting of: N—N-didecyl-N-methyl-N-(3-trimethoxysilyl-propyparrimoniurn chloride; octadecyldimethyl(3-trimethoxysilylpropyl)ammonium chloride; 3-trihydroxysilylpropylmethyl phosphonate, sodium salt; and carboxylethylsilanetriol, sodium salt.

8. The nitric oxide-releasing particle of claim 4, wherein the alkylsilane is selected from the group consisting of methyltrimethoxysilane, butyltrimethoxysilarie, butyltriethoxysilane, propyltrimethoxysilane, and octadecyltrimethoxysilane.

9. The nitric oxide-releasing particle of claim 1, wherein the particle has a diameter of from about 1 nm to about 1000 nm.

10. The nitric oxide-releasing particle of claim 1, wherein the particle has a diameter of from about 1 nm to about 5 nm.

11. The nitric oxide-releasing particle of claim 1, wherein the particle has a diameter of from about 2 nm to about 10 μm.

* * * * *

UNITED STATES PATENT AND TRADEMARK OFFICE
CERTIFICATE OF CORRECTION

PATENT NO. : 8,282,967 B2
APPLICATION NO. : 13/168597
DATED : October 9, 2012
INVENTOR(S) : Schoenfisch et al.

It is certified that error appears in the above-identified patent and that said Letters Patent is hereby corrected as shown below:

Column 52, Claim 5, line 16, change "tetraniethyl" to -- tetramethyl --;

Column 52, Claim 7, line 25, change "propyparrimoniurn" to -- propyl)ammonium --;

Column 52, Claim 8, line 31, change "butyltrimethoxysilarie" to -- butyltrimethoxysilane --.

Signed and Sealed this
First Day of January, 2013

David J. Kappos
*Director of the United States Patent and Trademark Office*